US009340618B2

(12) United States Patent
Edwards et al.

(10) Patent No.: US 9,340,618 B2
(45) Date of Patent: May 17, 2016

(54) IL-11R BINDING PROTEINS

(71) Applicant: CSL Limited, Parkville, Victoria (AU)

(72) Inventors: Kirsten Edwards, Parkville (AU);
Matthew Hardy, Parkville (AU);
Veronika Rayzman, Parkville (AU);
Michael Wilson, Parkville (AU)

(73) Assignee: CSL LIMITED, Parkville, Victoria (AU)

( * ) Notice: Subject to any disclaimer, the term of this patent is extended or adjusted under 35 U.S.C. 154(b) by 67 days.

(21) Appl. No.: 14/174,009

(22) Filed: Feb. 6, 2014

(65) Prior Publication Data

US 2014/0219919 A1 Aug. 7, 2014

Related U.S. Application Data

(60) Provisional application No. 61/764,756, filed on Feb. 14, 2013.

(30) Foreign Application Priority Data

Feb. 7, 2013 (AU) ................. 2013900389

(51) Int. Cl.
*A61K 39/00* (2006.01)
*C07K 16/28* (2006.01)
*G01N 33/569* (2006.01)

(52) U.S. Cl.
CPC ...... *C07K 16/2866* (2013.01); *G01N 33/56966* (2013.01); *C07K 2317/34* (2013.01); *C07K 2317/55* (2013.01); *C07K 2317/76* (2013.01); *C07K 2317/92* (2013.01); *G01N 2333/7155* (2013.01)

(58) Field of Classification Search
None
See application file for complete search history.

(56) References Cited

U.S. PATENT DOCUMENTS 7,094,402 B2 * 8/2006 Tobin ........................ 424/139.1
2009/0202533 A1 8/2009 Baca et al.

OTHER PUBLICATIONS

Data Sheet from R&D Systems, accessed Mar. 16, 2015.*
Citation data from R&D Systems, accessed Mar. 16, 2014.*
Arte et al., Am. J. Human. Genet. 89, 67-81, 2011.*
Sottnik et al., Interleukin-11 receptor alpha is expressed on canine osteosarcoma, Vet. Comp. Oncol., 8, 96-102, 2010.*
Armour, K. L., et al. "Recombinant human IgG molecules lacking Fcγ receptor I binding and monocyte triggering activities" Eur. J. Immunol. 29:2613-2624 (1999).
Bendele, A,M., "Animal models of rheumatoid arthritis" J Musculoskel Neuron Interact 1(4):377-385 (2001).
Blanc, C., et al., "Monoclonal antibodies against the human interleukin-11 receptor alpha-chain (IL-11Rα) and their use in studies of human mononuclear cells" Journal of Immunological Methods 241:43-59 (2000).
Bork, P., et al., "The Immunoglobulin Fold Structural Classification, Sequence Patterns and Common Core" J. Mol. Biol. 242:309-320 (1994).
Brüggemann, M., et al., "Comparison of the Effector Functions of Human Immunoglobulins Using a Matched Set of Chimeric Antibodies" J. Exp. Med. 155:1351-1361 (1987).
Chothia, C., et al., "Canonical Structures for the Hypervariable Regions of Immunoglobulins" J. Mol. Biol. 196:907-917 (1987).
Dall'Acqua, W. F., et al., "Modulation of the Effector Functions of a Human IgG1 through Engineering of Its Hinge Region" J Immunol 177:1129-1138 (2006).
Dams-Kozlowska, H., et al., "A designer hyper interleukin 11 (H11) is a biologically active cytokine" BMC Biotechnology 12(8):1-11 (2012).
Edelman, G. M., et al., "The Covalent Structure of an Entire γG Immunoglobulin Molecule" Biochemistry 63:78-85 (1969).
Fattouh, R., et al., "House Dust Mite Facilitates Ovalbumin-specific Allergic Sensitization and Airway Inflammation" Am J Respir Crit Care Med 172:314-321 (2005).
Gazzano-Santoro, H., et al., "A non-radioactive complement-dependent cytotoxicity assay for anti-CD20 monoclonal antibody" Journal of Immunological Methods 202:163-171 (1997).
Giudicelli, V., et al., "IMGT, the international ImMunoGeneTics database" Nucleic Acids Research 25(1):206-211 (1997).
Greten, F. R., et al."IKKβ Links Inflammation and Tumorigenesis in a Mouse Model of Colitis-Associated Cancer" Cell 118:285-296 (2004).
Hellström, I., et al., "Antitumor effects of 6, an IgG2a antibody that reacts with most human carcinomas" Proc. Natl. Acad. Sci. 83:7059-7063 (1986).
Homma, T., et al., "Airway hyperresponsiveness induced by cationic proteins in vivo: site of action" Am J Physiol Lung Cell Mol Physiol 289:L413-L418 (2005).
Honegger, A., et al., "Yet Another Numbering Scheme for Immunoglobulin Variable Domains: An Automatic Modeling and Analysis Tool" J. Mol. Biol. 309:657-670 (2001).
Jenkins, B. J., et al., "Pathologic consequences of STAT3 hyperactivation by IL-6 and IL-11 during hematopoiesis and lymphopoiesis" 109:2380-2388 (2007).
Kanda, Y., et al., "Establishment of a GDP-mannose 4,6-dehydratase (GMD) knockout host cell line: A new strategy for generating completely non-fucosylated recombinant therapeutics" Journal of Biotechnology 130:300-310 (2007).
Kim, J. et al., "Identifying amino acid residues that influence plasma clearance of murine IgG1 fragments by site-directed mutagenesis" Eur. J. Immunol. 24:542-548 (1994).
Kimura, T., et al., "Interleukin-11 (IL-11) enhances clonal proliferation of acute myelogenous leukemia cells with strong expression of the IL-11 receptor α chain and signal transducing gp130" Leukemia 13:1018-1027 (1999).
Kogan, M., et al., "Peptides and metallic nanoparticles for biomedical applications" Nanomedicine 2(3):287-306 (2007).

(Continued)

*Primary Examiner* — Elly-Gerald Stoica
(74) *Attorney, Agent, or Firm* — Scully, Scott, Murphy & Presser, P.C.

(57) ABSTRACT

The present disclosure provides proteins comprising antigen binding sites of antibodies that bind to interleukin-11 (IL-11) receptor alpha (IL-11Rα) and uses thereof, e.g., in therapy.

15 Claims, 8 Drawing Sheets

(56) References Cited

OTHER PUBLICATIONS

Kopsidas, G., et al., "In vitro improvement of a shark IgNAR antibody by Qβ replicase mutation and ribosome display mimics in vivo affinity maturation" Immunology Letters 107:163-168 (2006).

Kunkel, T. A., et al., "Rapid and Efficient Site-Specific Mutagenesis without Phenotypic Selection" Methods in Enzymology 154:367-382 (1987).

Kyte, J., et al., "A Simple Method for Displaying the Hydropathic Character of a Protein" J. Mol. Biol. 157:105-132 (1982).

Largaespada, D. A., et al., "The ABL-MYC retrovirus generates antigen-specific plasmacytomas by in vitro infection of activated B lymphocytes from spleen and other murine lymphoid organs" Journal of Immunological Methods 197:85-95 (1996).

Li, M., et al., "A novel animal model for bone metastasis in human lung cancer" Oncology Letters 3:802-806 (2012).

Mori, K. et al., "Engineering Chinese Hamster Ovary Cells to Maximize Effector Function of Produced Antibodies Using FUT8 siRNA" Biotechnology and Bioengineering 88(7):901-908 (2004).

Natsume, A., et al., "Engineered Antibodies of IgG1/IgG3 Mixed Isotype with Enhanced Cytotoxic Activities" Cancer Res 68(10):3863-3872 (2008).

Needleman, S. B., et al., "A General Method Applicable to the Search for Similarities in the Amino Acid Sequence of Two Proteins" J. Mol. Biol. 48:443-453 (1970).

Padlan, E. A., et al., "Identification of specificity-determining residues in antibodies" FASEB J. 9:133-139 (1995).

Sakaguchi, N., et al., "Altered thymic T-cell selection due to a mutation of the ZAP-70 gene causes autoimmune arthritis in mice" Nature 426:454-460 (2003).

Shields, R. L., et al., "High Resolution Mapping of the Binding Site on Human IgG1 for FcγRI, FcγRII, FcγIII, and FcRn and Design of IgG1 Variants with Improved Binding to the FcγR" The Journal of Biological Chemistry 276(9):6591-6604 (2001).

Sidhu, S. S., et al., "Phage Display for Selection of Novel Binding Peptides" Methods in Enzymology 328:333-363 (2000).

Stemmer, W. P. C., et al. "Rapid evolution of a protein in vitro by DNA shuffling" Nature 370:389-391 (1994).

Thie, H., et al., "Affinity Maturation by Phage Display" Therapeutic Antibodies: Method and Protocols 525:309-322 (2009).

Umaña, P., et al., "Engineered glycoforms of an antineuro-blastoma IgG1 with optimized antibody-dependent cellular cytotoxic activity" Nature Biotechnology 17:176-180 (1999).

Wang, J., et al., "IL-11 Selectively Inhibits Aeroallergen-Induced Pulmonary Eosinophilia and Th2 Cytokine Production" The Journal of Immunology 165:2222-2231 (2000).

Yamana-Ohnuki, N., et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity" Biotechnology and Bioengineering 87(5):614-622 (2004).

Yokota, H., et al., "Quantitative In Vitro Bioassay for Recombinant Human Interleukin-11" Journal of AOAC International 83(5):1053-1058 (2000).

Zhang, Z., et al., "Interleukin-11 Promotes the Progress of Gastric Carcinoma via Abnormally Expressed Versican" Int. J. Biol. Sci. 8:383-393 (2012).

\* cited by examiner

| 8E2 L1 | INNYLN | 8E2 L3.1 | QQYDNL | 8E2 L3.2 | DNLSPT |
|---|---|---|---|---|---|
| TS-303 | VDYWVE | TS-2 | QQAEDQ | TS-49 | ESQAPE |
| TS-305 | VGIYVE | TS-4 | QQHEFQ | TS-51 | ESQWPF |
| TS-306 | VDKYVE | TS-6 | EQFESQ | TS-55 | ETQTPA |
| TS-307 | VSMYVE | TS-7 | QQHENQ | TS-57 | ETQMPL |
| TS-310 | VAMYIE | TS-9 | QQAEEQ | TS-58 | ETQQPF |
| TS-311 | VSQYIE | TS-13 | QQNETQ | TS-63 | DTQQPN |
| TS-312 | IGQYVE | TS-14 | QQHDNQ | TS-64 | ESQWPQ |
| TS-313 | VSGYVE | TS-17 | SQFESQ | Consensus | ETQXPF |
| TS-322 | VHHYME | TS-20 | QQNESQ | | |
| Consensus | VSXYVE | TS-21 | QQSESQ | | |
| | | TS-22 | QQFETQ | | |
| | | TS-29 | QQSEEQ | | |
| | | TS-32 | TQWETQ | | |
| | | Consensus | QQXESQ | | |

Figure 1

| 8E2 H1 | SWYSMT | 8E2 H2 | VPSGGH | 8E2 H3.1 | GPGWGS | 8E2 H3.2 | WGSFDL |
|---|---|---|---|---|---|---|---|
| TS-66 | AWWSIA | TS-97 | VPWADY | TS-129 | PEDWGM | TS-213 | WGQFAV |
| TS-69 | GWWSVT | TS-101 | VPWGDL | TS-133 | PVDWGR | TS-214 | WGSFWF |
| TS-71 | WRWSTT | TS-103 | VPYGDL | TS-134 | PEDWGL | TS-215 | WGSFWQ |
| TS-76 | WRWSIT | TS-104 | VPWGTI | TS-135 | PLDWGL | TS-218 | WGSFWE |
| TS-79 | AWFSVT | TS-107 | VPWGDF | TS-136 | PLDWGR | TS-221 | WGSFWY |
| TS-82 | WRWSVT | TS-108 | VPWGTL | TS-140 | PNDWGL | TS-222 | WGTFAY |
| TS-88 | WRWSTT | TS-115 | VPHGDL | TS-143 | PHDWGL | TS-224 | WGSFWT |
| TS-89 | WRWSIT | Consensus | VPWGDL | TS-151 | PHDWGR | Consensus | WGSFWY |
| TS-90 | EWYSIT | | | TS-156 | PEDWGR | | |
| TS-91 | GWWSLT | | | Consensus | PEDWGX | | |
| TS-92 | SWWSIT | | | | | | |
| Consensus | WWWSIT | | | | | | |

Figure 2

|  |  | CDR1 |  | CDR2 |
|---|---|---|---|---|
| 8E2 | DIQMTQSPSSLSASVGDRVTITC | QASQD INNYLN | WYQQKPGKAPKLLIY | DASNLQT |
| TS-303 | DIQMTQSPSSLSASVGDRVTITC | QASQD VDYWVE | WYQQKPGKAPKLLIY | DASNLQT |
| TS-305 | DIQMTQSPSSLSASVGDRVTITC | QASQD VGIYVE | WYQQKPGKAPKLLIY | DASNLQT |
| TS-306 | DIQMTQSPSSLSASVGDRVTITC | QASQD VDKYVE | WYQQKPGKAPKLLIY | DASNLQT |
| TS-307 | DIQMTQSPSSLSASVGDRVTITC | QASQD VSMYIE | WYQQKPGKAPKLLIY | DASNLQT |
| TS-310 | DIQMTQSPSSLSASVGDRVTITC | QASQD VAMYIE | WYQQKPGKAPKLLIY | DASNLQT |
| TS-311 | DIQMTQSPSSLSASVGDRVTITC | QASQD VSQYIE | WYQQKPGKAPKLLIY | DASNLQT |
| TS-312 | DIQMTQSPSSLSASVGDRVTITC | QASQD IGQYVE | WYQQKPGKAPKLLIY | DASNLQT |
| TS-313 | DIQMTQSPSSLSASVGDRVTITC | QASQD VSGYVE | WYQQKPGKAPKLLIY | DASNLQT |
| TS-322 | DIQMTQSPSSLSASVGDRVTITC | QASQD VHHYME | WYQQKPGKAPKLLIY | DASNLQT |
| TS-2 | DIQMTQSPSSLSASVGDRVTITC | QASQD INNYLN | WYQQKPGKAPKLLIY | DASNLQT |
| TS-4 | DIQMTQSPSSLSASVGDRVTITC | QASQD INNYLN | WYQQKPGKAPKLLIY | DASNLQT |
| TS-6 | DIQMTQSPSSLSASVGDRVTITC | QASQD INNYLN | WYQQKPGKAPKLLIY | DASNLQT |
| TS-7 | DIQMTQSPSSLSASVGDRVTITC | QASQD INNYLN | WYQQKPGKAPKLLIY | DASNLQT |
| TS-9 | DIQMTQSPSSLSASVGDRVTITC | QASQD INNYLN | WYQQKPGKAPKLLIY | DASNLQT |
| TS-13 | DIQMTQSPSSLSASVGDRVTITC | QASQD INNYLN | WYQQKPGKAPKLLIY | DASNLQT |
| TS-14 | DIQMTQSPSSLSASVGDRVTITC | QASQD INNYLN | WYQQKPGKAPKLLIY | DASNLQT |
| TS-17 | DIQMTQSPSSLSASVGDRVTITC | QASQD INNYLN | WYQQKPGKAPKLLIY | DASNLQT |
| TS-20 | DIQMTQSPSSLSASVGDRVTITC | QASQD INNYLN | WYQQKPGKAPKLLIY | DASNLQT |
| TS-21 | DIQMTQSPSSLSASVGDRVTITC | QASQD INNYLN | WYQQKPGKAPKLLIY | DASNLQT |
| TS-22 | DIQMTQSPSSLSASVGDRVTITC | QASQD INNYLN | WYQQKPGKAPKLLIY | DASNLQT |
| TS-29 | DIQMTQSPSSLSASVGDRVTITC | QASQD INNYLN | WYQQKPGKAPKLLIY | DASNLQT |
| TS-32 | DIQMTQSPSSLSASVGDRVTITC | QASQD INNYLN | WYQQKPGKAPKLLIY | DASNLQT |
| TS-49 | DIQMTQSPSSLSASVGDRVTITC | QASQD INNYLN | WYQQKPGKAPKLLIY | DASNLQT |
| TS-51 | DIQMTQSPSSLSASVGDRVTITC | QASQD INNYLN | WYQQKPGKAPKLLIY | DASNLQT |
| TS-55 | DIQMTQSPSSLSASVGDRVTITC | QASQD INNYLN | WYQQKPGKAPKLLIY | DASNLQT |
| TS-57 | DIQMTQSPSSLSASVGDRVTITC | QASQD INNYLN | WYQQKPGKAPKLLIY | DASNLQT |
| TS-58 | DIQMTQSPSSLSASVGDRVTITC | QASQD INNYLN | WYQQKPGKAPKLLIY | DASNLQT |
| TS-63 | DIQMTQSPSSLSASVGDRVTITC | QASQD INNYLN | WYQQKPGKAPKLLIY | DASNLQT |
| TS-64 | DIQMTQSPSSLSASVGDRVTITC | QASQD INNYLN | WYQQKPGKAPKLLIY | DASNLQT |
| Consensus | DIQMTQSPSSLSASVGDRVTITC | QASQD XXXXXX | WYQQKPGKAPKLLIY | DASNLQT |

```
                                        INNYLN
                                        VDYWVE
                                        GI  I
                                        SK  M
                                        AM
                                        HQ
                                         G
                                         H
```

Figure 3A

|  |  | CDR3 |  |  |
|---|---|---|---|---|
| 8E2 | GVPSRFSGSGSGTDFTFTISSLQPEDIATYYC | QQYDNL SPT | FGPGTKVDIK | SEQ ID NO: 5 |
| TS-303 | GVPSRFSGSGSGTDFTFTISSLQPEDIATYYC | QQYDNL SPT | FGPGTKVDIK | SEQ ID NO: 6 |
| TS-305 | GVPSRFSGSGSGTDFTFTISSLQPEDIATYYC | QQYDNL SPT | FGPGTKVDIK | SEQ ID NO: 7 |
| TS-306 | GVPSRFSGSGSGTDFTFTISSLQPEDIATYYC | QQYDNL SPT | FGPGTKVDIK | SEQ ID NO: 8 |
| TS-307 | GVPSRFSGSGSGTDFTFTISSLQPEDIATYYC | QQYDNL SPT | FGPGTKVDIK | SEQ ID NO: 9 |
| TS-310 | GVPSRFSGSGSGTDFTFTISSLQPEDIATYYC | QQYDNL SPT | FGPGTKVDIK | SEQ ID NO: 10 |
| TS-311 | GVPSRFSGSGSGTDFTFTISSLQPEDIATYYC | QQYDNL SPT | FGPGTKVDIK | SEQ ID NO: 11 |
| TS-312 | GVPSRFSGSGSGTDFTFTISSLQPEDIATYYC | QQYDNL SPT | FGPGTKVDIK | SEQ ID NO: 12 |
| TS-313 | GVPSRFSGSGSGTDFTFTISSLQPEDIATYYC | QQYDNL SPT | FGPGTKVDIK | SEQ ID NO: 13 |
| TS-322 | GVPSRFSGSGSGTDFTFTISSLQPEDIATYYC | QQYDNL SPT | FGPGTKVDIK | SEQ ID NO: 14 |
| TS-2 | GVPSRFSGSGSGTDFTFTISSLQPEDIATYYC | QQAEDQ SPT | FGPGTKVDIK | SEQ ID NO: 15 |
| TS-4 | GVPSRFSGSGSGTDFTFTISSLQPEDIATYYC | QQHEFQ SPT | FGPGTKVDIK | SEQ ID NO: 16 |
| TS-6 | GVPSRFSGSGSGTDFTFTISSLQPEDIATYYC | EQFESQ SPT | FGPGTKVDIK | SEQ ID NO: 17 |
| TS-7 | GVPSRFSGSGSGTDFTFTISSLQPEDIATYYC | QQHENQ SPT | FGPGTKVDIK | SEQ ID NO: 18 |
| TS-9 | GVPSRFSGSGSGTDFTFTISSLQPEDIATYYC | QQAEEQ SPT | FGPGTKVDIK | SEQ ID NO: 19 |
| TS-13 | GVPSRFSGSGSGTDFTFTISSLQPEDIATYYC | QQNETQ SPT | FGPGTKVDIK | SEQ ID NO: 20 |
| TS-14 | GVPSRFSGSGSGTDFTFTISSLQPEDIATYYC | QQHDNQ SPT | FGPGTKVDIK | SEQ ID NO: 21 |
| TS-17 | GVPSRFSGSGSGTDFTFTISSLQPEDIATYYC | SQFESQ SPT | FGPGTKVDIK | SEQ ID NO: 22 |
| TS-20 | GVPSRFSGSGSGTDFTFTISSLQPEDIATYYC | QQNESQ SPT | FGPGTKVDIK | SEQ ID NO: 23 |
| TS-21 | GVPSRFSGSGSGTDFTFTISSLQPEDIATYYC | QQSESQ SPT | FGPGTKVDIK | SEQ ID NO: 24 |
| TS-22 | GVPSRFSGSGSGTDFTFTISSLQPEDIATYYC | QQFETQ SPT | FGPGTKVDIK | SEQ ID NO: 25 |
| TS-29 | GVPSRFSGSGSGTDFTFTISSLQPEDIATYYC | QQSEEQ SPT | FGPGTKVDIK | SEQ ID NO: 26 |
| TS-32 | GVPSRFSGSGSGTDFTFTISSLQPEDIATYYC | TQWETQ SPT | FGPGTKVDIK | SEQ ID NO: 27 |
| TS-49 | GVPSRFSGSGSGTDFTFTISSLQPEDIATYYC | QQYESQ APE | FGPGTKVDIK | SEQ ID NO: 28 |
| TS-51 | GVPSRFSGSGSGTDFTFTISSLQPEDIATYYC | QQYESQ WPF | FGPGTKVDIK | SEQ ID NO: 29 |
| TS-55 | GVPSRFSGSGSGTDFTFTISSLQPEDIATYYC | QQYETQ TPA | FGPGTKVDIK | SEQ ID NO: 30 |
| TS-57 | GVPSRFSGSGSGTDFTFTISSLQPEDIATYYC | QQYETQ MPL | FGPGTKVDIK | SEQ ID NO: 31 |
| TS-58 | GVPSRFSGSGSGTDFTFTISSLQPEDIATYYC | QQYETQ QPF | FGPGTKVDIK | SEQ ID NO: 32 |
| TS-63 | GVPSRFSGSGSGTDFTFTISSLQPEDIATYYC | QQYDTQ QPN | FGPGTKVDIK | SEQ ID NO: 33 |
| TS-64 | GVPSRFSGSGSGTDFTFTISSLQPEDIATYYC | QQYESQ WPQ | FGPGTKVDIK | SEQ ID NO: 34 |
| Consensus | GVPSRFSGSGSGTDFTFTISSLQPEDIATYYC | XQXXXX XPX | FGPGTKVDIK | SEQ ID NO: 35 |

```
Consensus CDR3 variants:
  Q YDNL  S T
  E AEDQ  A E
  S H F   W F
  T F S   T A
    N E   M L
    S T   Q N
    W         Q
```

Figure 3A Continued

```
                                    CDR1                         CDR2
8E2        DIQMTQSPSSLSASVGDRVTITC  QASQD INNYLN  WYQQKPGKAPKLLIY  DASNLQT   SEQ ID NO:

TS-306     DIQMTQSPSSLSASVGDRVTITC  QASQD VDKYVE  WYQQKPGKAPKLLIY  DASNLQT
TS-2       DIQMTQSPSSLSASVGDRVTITC  QASQD INNYLN  WYQQKPGKAPKLLIY  DASNLQT
TS-4       DIQMTQSPSSLSASVGDRVTITC  QASQD INNYLN  WYQQKPGKAPKLLIY  DASNLQT
TS-7       DIQMTQSPSSLSASVGDRVTITC  QASQD INNYLN  WYQQKPGKAPKLLIY  DASNLQT
TS-14      DIQMTQSPSSLSASVGDRVTITC  QASQD INNYLN  WYQQKPGKAPKLLIY  DASNLQT
TS-51      DIQMTQSPSSLSASVGDRVTITC  QASQD INNYLN  WYQQKPGKAPKLLIY  DASNLQT

Consensus  DIQMTQSPSSLSASVGDRVTITC  QASQD XXXYXX  WYQQKPGKAPKLLIY  DASNLQT
                                          IDK LN
                                          VNN VE CDR3
8E2        GVPSRFSGSGSGTDFTFTISSLQPEDIATYYC  QQYDNL SPT  FGPGTKVDIK   SEQ ID NO: 5

TS-306     GVPSRFSGSGSGTDFTFTISSLQPEDIATYYC  QQYDNL SPT  FGPGTKVDIK   SEQ ID NO: 8
TS-2       GVPSRFSGSGSGTDFTFTISSLQPEDIATYYC  QQAEDQ SPT  FGPGTKVDIK   SEQ ID NO: 15
TS-4       GVPSRFSGSGSGTDFTFTISSLQPEDIATYYC  QQHEFQ SPT  FGPGTKVDIK   SEQ ID NO: 16
TS-7       GVPSRFSGSGSGTDFTFTISSLQPEDIATYYC  QQHENQ SPT  FGPGTKVDIK   SEQ ID NO: 18
TS-14      GVPSRFSGSGSGTDFTFTISSLQPEDIATYYC  QQHDNQ SPT  FGPGTKVDIK   SEQ ID NO: 21
TS-51      GVPSRFSGSGSGTDFTFTISSLQPEDIATYYC  QQYESQ WPF  FGPGTKVDIK   SEQ ID NO: 29

Consensus  GVPSRFSGSGSGTDFTFTISSLQPEDIATYYC  QQXXXX XPX  FGPGTKVDIK   SEQ ID NO: 36
                                            YDNL  S T
                                            AEDQ  W F
                                            H  F
                                            N
                                            S
```

Figure 3B

```
                                                              CDR1                              CDR2
8E2         EVQLLESGGGLVQPGGSLRLSCAASGFTF S  WYSMT  WVRQAPGKGLEWVS SI VPSGGH TQYADSVKG

T6-66       EVQLLESGGGLVQPGGSLRLSCAASGFTF A  WWSIA  WVRQAPGKGLEWVS SI VPSGGH TQYADSVKG
TS-69       EVQLLESGGGLVQPGGSLRLSCAASGFTF G  WWSVT  WVRQAPGKGLEWVS SI VPSGGH TQYADSVKG
TS-71       EVQLLESGGGLVQPGGSLRLSCAASGFTF W  RWSTT  WVRQAPGKGLEWVS SI VPSGGH TQYADSVKG
TS-76       EVQLLESGGGLVQPGGSLRLSCAASGFTF W  RWSIT  WVRQAPGKGLEWVS SI VPSGGH TQYADSVKG
TS-79       EVQLLESGGGLVQPGGSLRLSCAASGFTF A  WFSVT  WVRQAPGKGLEWVS SI VPSGGH TQYADSVKG
TS-82       EVQLLESGGGLVQPGGSLRLSCAASGFTF W  RWSVT  WVRQAPGKGLEWVS SI VPSGGH TQYADSVKG
TS-88       EVQLLESGGGLVQPGGSLRLSCAASGFTF W  RWSTT  WVRQAPGKGLEWVS SI VPSGGH TQYADSVKG
TS-89       EVQLLESGGGLVQPGGSLRLSCAASGFTF W  RWSIT  WVRQAPGKGLEWVS SI VPSGGH TQYADSVKG
TS-91       EVQLLESGGGLVQPGGSLRLSCAASGFTF G  WWSLT  WVRQAPGKGLEWVS SI VPSGGH TQYADSVKG
TS-92       EVQLLESGGGLVQPGGSLRLSCAASGFTF S  WWSIT  WVRQAPGKGLEWVS SI VPSGGH TQYADSVKG
TS-97       EVQLLESGGGLVQPGGSLRLSCAASGFTF S  WYSMT  WVRQAPGKGLEWVS SI VPWADY TQYADSVKG
TS-101      EVQLLESGGGLVQPGGSLRLSCAASGFTF S  WYSMT  WVRQAPGKGLEWVS SI VPWGDL TQYADSVKG
TS-103      EVQLLESGGGLVQPGGSLRLSCAASGFTF S  WYSMT  WVRQAPGKGLEWVS SI VPYGDL TQYADSVKG
TS-104      EVQLLESGGGLVQPGGSLRLSCAASGFTF S  WYSMT  WVRQAPGKGLEWVS SI VPWGTI TQYADSVKG
TS-107      EVQLLESGGGLVQPGGSLRLSCAASGFTF S  WYSMT  WVRQAPGKGLEWVS SI VPWGDF TQYADSVKG
TS-108      EVQLLESGGGLVQPGGSLRLSCAASGFTF S  WYSMT  WVRQAPGKGLEWVS SI VPWGTL TQYADSVKG
TS-115      EVQLLESGGGLVQPGGSLRLSCAASGFTF S  WYSMT  WVRQAPGKGLEWVS SI VPHGDL TQYADSVKG
TS-129      EVQLLESGGGLVQPGGSLRLSCAASGFTF S  WYSMT  WVRQAPGKGLEWVS SI VPSGGH TQYADSVKG
TS-133      EVQLLESGGGLVQPGGSLRLSCAASGFTF S  WYSMT  WVRQAPGKGLEWVS SI VPSGGH TQYADSVKG
TS-134      EVQLLESGGGLVQPGGSLRLSCAASGFTF S  WYSMT  WVRQAPGKGLEWVS SI VPSGGH TQYADSVKG
TS-135      EVQLLESGGGLVQPGGSLRLSCAASGFTF S  WYSMT  WVRQAPGKGLEWVS SI VPSGGH TQYADSVKG
TS-136      EVQLLESGGGLVQPGGSLRLSCAASGFTF S  WYSMT  WVRQAPGKGLEWVS SI VPSGGH TQYADSVKG
TS-140      EVQLLESGGGLVQPGGSLRLSCAASGFTF S  WYSMT  WVRQAPGKGLEWVS SI VPSGGH TQYADSVKG
TS-143      EVQLLESGGGLVQPGGSLRLSCAASGFTF S  WYSMT  WVRQAPGKGLEWVS SI VPSGGH TQYADSVKG
TS-151      EVQLLESGGGLVQPGGSLRLSCAASGFTF S  WYSMT  WVRQAPGKGLEWVS SI VPSGGH TQYADSVKG
TS-156      EVQLLESGGGLVQPGGSLRLSCAASGFTF S  WYSMT  WVRQAPGKGLEWVS SI VPSGGH TQYADSVKG
TS-213      EVQLLESGGGLVQPGGSLRLSCAASGFTF S  WYSMT  WVRQAPGKGLEWVS SI VPSGGH TQYADSVKG
TS-214      EVQLLESGGGLVQPGGSLRLSCAASGFTF S  WYSMT  WVRQAPGKGLEWVS SI VPSGGH TQYADSVKG
TS-215      EVQLLESGGGLVQPGGSLRLSCAASGFTF S  WYSMT  WVRQAPGKGLEWVS SI VPSGGH TQYADSVKG
TS-218      EVQLLESGGGLVQPGGSLRLSCAASGFTF S  WYSMT  WVRQAPGKGLEWVS SI VPSGGH TQYADSVKG
TS-221      EVQLLESGGGLVQPGGSLRLSCAASGFTF S  WYSMT  WVRQAPGKGLEWVS SI VPSGGH TQYADSVKG
TS-222      EVQLLESGGGLVQPGGSLRLSCAASGFTF S  WYSMT  WVRQAPGKGLEWVS SI VPSGGH TQYADSVKG
TS-224      EVQLLESGGGLVQPGGSLRLSCAASGFTF S  WYSMT  WVRQAPGKGLEWVS SI VPSGGH TQYADSVKG

Consensus   EVQLLESGGGLVQPGGSLRLSCAASGFTF X  XXSXX  WVRQAPGKGLEWVS SI VPXXXX TQYADSVKG
                                         S  WY MT                    SGGH
                                         A  RW IA                    WADY
                                         G  F  V                     Y  TL
                                         W     T                     H   I
                                               L                         F
```

Figure 3C

```
                                                                       CDR3
8E2         RFTISRDNSKNTLYLQMNSLRAEDTAVYYCAK GPG WGSFDL  WGRGTLVTVSS   SEQ ID NO: 37

T6-66       RFTISRDNSKNTLYLQMNSLRAEDTAVYYCAK GPG WGSFDL  WGRGTLVTVSS   SEQ ID NO: 38
TS-69       RFTISRDNSKNTLYLQMNSLRAEDTAVYYCAK GPG WGSFDL  WGRGTLVTVSS   SEQ ID NO: 39
TS-71       RFTISRDNSKNTLYLQMNSLRAEDTAVYYCAK GPG WGSFDL  WGRGTLVTVSS   SEQ ID NO: 40
TS-76       RFTISRDNSKNTLYLQMNSLRAEDTAVYYCAK GPG WGSFDL  WGRGTLVTVSS   SEQ ID NO: 41
TS-79       RFTISRDNSKNTLYLQMNSLRAEDTAVYYCAK GPG WGSFDL  WGRGTLVTVSS   SEQ ID NO: 42
TS-82       RFTISRDNSKNTLYLQMNSLRAEDTAVYYCAK GPG WGSFDL  WGRGTLVTVSS   SEQ ID NO: 43
TS-88       RFTISRDNSKNTLYLQMNSLRAEDTAVYYCAK GPG WGSFDL  WGRGTLVTVSS   SEQ ID NO: 44
TS-89       RFTISRDNSKNTLYLQMNSLRAEDTAVYYCAK GPG WGSFDL  WGRGTLVTVSS   SEQ ID NO: 45
TS-91       RFTISRDNSKNTLYLQMNSLRAEDTAVYYCAK GPG WGSFDL  WGRGTLVTVSS   SEQ ID NO: 46
TS-92       RFTISRDNSKNTLYLQMNSLRAEDTAVYYCAK GPG WGSFDL  WGRGTLVTVSS   SEQ ID NO: 47
TS-97       RFTISRDNSKNTLYLQMNSLRAEDTAVYYCAK GPG WGSFDL  WGRGTLVTVSS   SEQ ID NO: 48
TS-101      RFTISRDNSKNTLYLQMNSLRAEDTAVYYCAK GPG WGSFDL  WGRGTLVTVSS   SEQ ID NO: 49
TS-103      RFTISRDNSKNTLYLQMNSLRAEDTAVYYCAK GPG WGSFDL  WGRGTLVTVSS   SEQ ID NO: 50
TS-104      RFTISRDNSKNTLYLQMNSLRAEDTAVYYCAK GPG WGSFDL  WGRGTLVTVSS   SEQ ID NO: 51
TS-107      RFTISRDNSKNTLYLQMNSLRAEDTAVYYCAK GPG WGSFDL  WGRGTLVTVSS   SEQ ID NO: 52
TS-108      RFTISRDNSKNTLYLQMNSLRAEDTAVYYCAK GPG WGSFDL  WGRGTLVTVSS   SEQ ID NO: 53
TS-115      RFTISRDNSKNTLYLQMNSLRAEDTAVYYCAK GPG WGSFDL  WGRGTLVTVSS   SEQ ID NO: 54
TS-129      RFTISRDNSKNTLYLQMNSLRAEDTAVYYCAK PED WGMFDL  WGRGTLVTVSS   SEQ ID NO: 55
TS-133      RFTISRDNSKNTLYLQMNSLRAEDTAVYYCAK PVD WGRFDL  WGRGTLVTVSS   SEQ ID NO: 56
TS-134      RFTISRDNSKNTLYLQMNSLRAEDTAVYYCAK PED WGLFDL  WGRGTLVTVSS   SEQ ID NO: 57
TS-135      RFTISRDNSKNTLYLQMNSLRAEDTAVYYCAK PLD WGLFDL  WGRGTLVTVSS   SEQ ID NO: 58
TS-136      RFTISRDNSKNTLYLQMNSLRAEDTAVYYCAK PLD WGRFDL  WGRGTLVTVSS   SEQ ID NO: 59
TS-140      RFTISRDNSKNTLYLQMNSLRAEDTAVYYCAK PND WGLFDL  WGRGTLVTVSS   SEQ ID NO: 60
TS-143      RFTISRDNSKNTLYLQMNSLRAEDTAVYYCAK PHD WGLFDL  WGRGTLVTVSS   SEQ ID NO: 61
TS-151      RFTISRDNSKNTLYLQMNSLRAEDTAVYYCAK PHD WGRFDL  WGRGTLVTVSS   SEQ ID NO: 62
TS-156      RFTISRDNSKNTLYLQMNSLRAEDTAVYYCAK PED WGRFDL  WGRGTLVTVSS   SEQ ID NO: 63
TS-213      RFTISRDNSKNTLYLQMNSLRAEDTAVYYCAK GPG WGQFAV  WGRGTLVTVSS   SEQ ID NO: 64
TS-214      RFTISRDNSKNTLYLQMNSLRAEDTAVYYCAK GPG WGSFWF  WGRGTLVTVSS   SEQ ID NO: 65
TS-215      RFTISRDNSKNTLYLQMNSLRAEDTAVYYCAK GPG WGSFWQ  WGRGTLVTVSS   SEQ ID NO: 66
TS-218      RFTISRDNSKNTLYLQMNSLRAEDTAVYYCAK GPG WGSFWE  WGRGTLVTVSS   SEQ ID NO: 67
TS-221      RFTISRDNSKNTLYLQMNSLRAEDTAVYYCAK GPG WGSFWY  WGRGTLVTVSS   SEQ ID NO: 68
TS-222      RFTISRDNSKNTLYLQMNSLRAEDTAVYYCAK GPG WGTFAY  WGRGTLVTVSS   SEQ ID NO: 69
TS-224      RFTISRDNSKNTLYLQMNSLRAEDTAVYYCAK GPG WGSFWI  WGRGTLVTVSS   SEQ ID NO: 70

Consensus   RFTISRDNSKNTLYLQMNSLRAEDTAVYYCAK XXX WGXFXX  WGRGTLVTVSS   SEQ ID NO: 71
                                             GPG     S  DL
                                             PED     M  AV
                                             V       R  WF
                                             L       L  Q
                                             N       Q  E
                                             H       T  Y
                                             E          T
```

Figure 3C Continued

```
                                             CDR1                           CDR2
8E2        EVQLLESGGGLVQPGGSLRLSCAASGFTF  S  WYSMT  WVRQAPGKGLEWVS  SI VPSGGH  TQYADSVKG

TS-101     EVQLLESGGGLVQPGGSLRLSCAASGFTF  S  WYSMT  WVRQAPGKGLEWVS  SI VPWGDL  TQYADSVKG
TS-108     EVQLLESGGGLVQPGGSLRLSCAASGFTF  S  WYSMT  WVRQAPGKGLEWVS  SI VPWGTL  TQYADSVKG
TS-134     EVQLLESGGGLVQPGGSLRLSCAASGFTF  S  WYSMT  WVRQAPGKGLEWVS  SI VPSGGH  TQYADSVKG
TS-136     EVQLLESGGGLVQPGGSLRLSCAASGFTF  S  WYSMT  WVRQAPGKGLEWVS  SI VPSGGH  TQYADSVKG

Consensus  EVQLLESGGGLVQPGGSLRLSCAASGFTF  S  WYSMT  WVRQAPGKGLEWVS  SI VPXGXX  TQYADSVKG
                                                                         S  GH
                                                                         W  DL
                                                                            T CDR3
8E2        RFTISRDNSKNTLYLQMNSLRAEDTAVYYCAK  GPG WGSFDL  WGRGTLVTVSS    SEQ ID NO: 37

TS-101     RFTISRDNSKNTLYLQMNSLRAEDTAVYYCAK  GPG WGSFDL  WGRGTLVTVSS    SEQ ID NO: 49
TS-108     RFTISRDNSKNTLYLQMNSLRAEDTAVYYCAK  GPG WGSFDL  WGRGTLVTVSS    SEQ ID NO: 53
TS-134     RFTISRDNSKNTLYLQMNSLRAEDTAVYYCAK  PED WGLFDL  WGRGTLVTVSS    SEQ ID NO: 57
TS-136     RFTISRDNSKNTLYLQMNSLRAEDTAVYYCAK  PLD WGRFDL  WGRGTLVTVSS    SEQ ID NO: 59

Consensus  RFTISRDNSKNTLYLQMNSLRAEDTAVYYCAK  XXX WGXFDL  WGRGTLVTVSS    SEQ ID NO: 72
                                             GPG     S
                                             PED     L
                                             L       R
```

Figure 3D

SEQUENCE LISTING

```
<160> NUMBER OF SEQ ID NOS: 109

<210> SEQ ID NO 1
<211> LENGTH: 422
<212> TYPE: PRT
<213> ORGANISM: Homo sapiens

<400> SEQUENCE: 1

Met Ser Ser Ser Cys Ser Gly Leu Ser Arg Val Leu Val Ala Val Ala
1               5                   10                  15

Thr Ala Leu Val Ser Ala Ser Ser Pro Cys Pro Gln Ala Trp Gly Pro
            20                  25                  30

Pro Gly Val Gln Tyr Gly Gln Pro Gly Arg Ser Val Lys Leu Cys Cys
        35                  40                  45

Pro Gly Val Thr Ala Gly Asp Pro Val Ser Trp Phe Arg Asp Gly Glu
    50                  55                  60

Pro Lys Leu Leu Gln Gly Pro Asp Ser Gly Leu Gly His Glu Leu Val
65                  70                  75                  80

Leu Ala Gln Ala Asp Ser Thr Asp Glu Gly Thr Tyr Ile Cys Gln Thr
                85                  90                  95

Leu Asp Gly Ala Leu Gly Gly Thr Val Thr Leu Gln Leu Gly Tyr Pro
            100                 105                 110

Pro Ala Arg Pro Val Val Ser Cys Gln Ala Ala Asp Tyr Glu Asn Phe
        115                 120                 125

Ser Cys Thr Trp Ser Pro Ser Gln Ile Ser Gly Leu Pro Thr Arg Tyr
    130                 135                 140

Leu Thr Ser Tyr Arg Lys Lys Thr Val Leu Gly Ala Asp Ser Gln Arg
145                 150                 155                 160

Arg Ser Pro Ser Thr Gly Pro Trp Pro Cys Pro Gln Asp Pro Leu Gly
                165                 170                 175

Ala Ala Arg Cys Val Val His Gly Ala Glu Phe Trp Ser Gln Tyr Arg
            180                 185                 190

Ile Asn Val Thr Glu Val Asn Pro Leu Gly Ala Ser Thr Arg Leu Leu
        195                 200                 205

Asp Val Ser Leu Gln Ser Ile Leu Arg Pro Asp Pro Pro Gln Gly Leu
    210                 215                 220

Arg Val Glu Ser Val Pro Gly Tyr Pro Arg Arg Leu Arg Ala Ser Trp
225                 230                 235                 240
```

```
Thr Tyr Pro Ala Ser Trp Pro Cys Gln Pro His Phe Leu Leu Lys Phe
            245                 250                 255

Arg Leu Gln Tyr Arg Pro Ala Gln His Pro Ala Trp Ser Thr Val Glu
        260                 265                 270

Pro Ala Gly Leu Glu Glu Val Ile Thr Asp Ala Val Ala Gly Leu Pro
        275                 280                 285

His Ala Val Arg Val Ser Ala Arg Asp Phe Leu Asp Ala Gly Thr Trp
        290                 295                 300

Ser Thr Trp Ser Pro Glu Ala Trp Gly Thr Pro Ser Thr Gly Thr Ile
305                 310                 315                 320

Pro Lys Glu Ile Pro Ala Trp Gly Gln Leu His Thr Gln Pro Glu Val
            325                 330                 335

Glu Pro Gln Val Asp Ser Pro Ala Pro Pro Arg Pro Ser Leu Gln Pro
        340                 345                 350

His Pro Arg Leu Leu Asp His Arg Asp Ser Val Glu Gln Val Ala Val
        355                 360                 365

Leu Ala Ser Leu Gly Ile Leu Ser Phe Leu Gly Leu Val Ala Gly Ala
        370                 375                 380

Leu Ala Leu Gly Leu Trp Leu Arg Leu Arg Arg Gly Gly Lys Asp Gly
385                 390                 395                 400

Ser Pro Lys Pro Gly Phe Leu Ala Ser Val Ile Pro Val Asp Arg Arg
            405                 410                 415

Pro Gly Ala Pro Asn Leu
            420

<210> SEQ ID NO 2
<211> LENGTH: 432
<212> TYPE: PRT
<213> ORGANISM: Macaca fascicularis

<400> SEQUENCE: 2

Met Ser Ser Cys Ser Gly Leu Thr Arg Val Leu Val Ala Val Ala
1               5                   10                  15

Thr Ala Leu Val Ser Ser Ser Pro Cys Pro Gln Ala Trp Gly Pro
            20                  25                  30

Pro Gly Val Gln Tyr Gly Gln Pro Gly Arg Pro Val Met Leu Cys Cys
        35                  40                  45

Pro Gly Val Ser Ala Gly Thr Pro Val Ser Trp Phe Arg Asp Gly Asp
        50                  55                  60

Ser Arg Leu Leu Gln Gly Pro Asp Ser Gly Leu Gly His Arg Leu Val
65                  70                  75                  80

Leu Ala Gln Val Asp Ser Pro Asp Glu Gly Thr Tyr Val Cys Gln Thr
            85                  90                  95

Leu Asp Gly Val Ser Gly Gly Met Val Thr Leu Lys Leu Gly Phe Pro
        100                 105                 110

Pro Ala Arg Pro Glu Val Ser Cys Gln Ala Val Asp Tyr Glu Asn Phe
        115                 120                 125

Ser Cys Thr Trp Ser Pro Gly Gln Val Ser Gly Leu Pro Thr Arg Tyr
        130                 135                 140

Leu Thr Ser Tyr Arg Lys Lys Thr Leu Pro Gly Ala Glu Ser Gln Arg
145                 150                 155                 160

Glu Ser Pro Ser Thr Gly Pro Trp Pro Cys Pro Gln Asp Pro Leu Glu
            165                 170                 175

Ala Ser Arg Cys Val Val His Gly Ala Glu Phe Trp Ser Glu Tyr Arg
        180                 185                 190
```

-continued

```
Ile Asn Val Thr Glu Val Asn Pro Leu Gly Ala Ser Thr Cys Leu Leu
        195                 200                 205

Asp Val Arg Leu Gln Ser Ile Leu Arg Pro Asp Pro Gln Gly Leu
210                 215                 220

Arg Val Glu Ser Val Pro Gly Tyr Pro Arg Arg Leu His Ala Ser Trp
225                 230                 235                 240

Thr Tyr Pro Ala Ser Arg Arg Gln Pro His Phe Leu Leu Lys Phe
            245                 250                 255

Arg Leu Gln Tyr Arg Pro Ala Gln His Pro Ala Trp Ser Thr Val Glu
                260                 265                 270

Pro Ile Gly Leu Glu Glu Val Ile Thr Asp Thr Val Ala Gly Leu Pro
            275                 280                 285

His Ala Val Arg Val Ser Ala Arg Asp Phe Leu Asp Ala Gly Thr Trp
        290                 295                 300

Ser Ala Trp Ser Pro Glu Ala Trp Gly Thr Pro Ser Thr Gly Leu Leu
305                 310                 315                 320

Gln Asp Glu Ile Pro Asp Trp Ser Gln Gly His Gly Gln Leu Glu
                325                 330                 335

Ala Val Val Ala Gln Glu Asp Ser Leu Ala Pro Ala Arg Pro Ser Leu
            340                 345                 350

Gln Pro Asp Pro Arg Pro Leu Asp His Arg Asp Pro Leu Glu Gln Val
            355                 360                 365

Ala Val Leu Ala Ser Leu Gly Ile Phe Ser Cys Leu Gly Leu Ala Val
            370                 375                 380

Gly Ala Leu Ala Leu Gly Leu Trp Leu Arg Leu Arg Arg Ser Gly Lys
385                 390                 395                 400

Glu Gly Pro Gln Lys Pro Gly Leu Leu Ala Pro Met Ile Pro Val Glu
                405                 410                 415

Lys Leu Pro Gly Ile Pro Asn Leu Gln Arg Thr Pro Glu Asn Phe Ser
            420                 425                 430

<210> SEQ ID NO 3
<211> LENGTH: 349
<212> TYPE: PRT
<213> ORGANISM: artificial
<220> FEATURE:
<223> OTHER INFORMATION: polypeptide comprising amino acids 23 to 363
      of SEQ ID NO: 1 comprising a 8xHIS tag and a serine at a position
      corresponding to position 248 of SEQ ID NO: 1 (also referred to as
      "WT F/L")

<400> SEQUENCE: 3

Ser Ser Pro Cys Pro Gln Ala Trp Gly Pro Gly Val Gln Tyr Gly
1               5                   10                  15

Gln Pro Gly Arg Ser Val Lys Leu Cys Cys Pro Gly Val Thr Ala Gly
                20                  25                  30

Asp Pro Val Ser Trp Phe Arg Asp Gly Glu Pro Lys Leu Leu Gln Gly
            35                  40                  45

Pro Asp Ser Gly Leu Gly His Glu Leu Val Leu Ala Gln Ala Asp Ser
        50                  55                  60

Thr Asp Glu Gly Thr Tyr Ile Cys Gln Thr Leu Asp Gly Ala Leu Gly
65                  70                  75                  80

Gly Thr Val Thr Leu Gln Leu Gly Tyr Pro Pro Ala Arg Pro Val Val
                85                  90                  95

Ser Cys Gln Ala Ala Asp Tyr Glu Asn Phe Ser Cys Thr Trp Ser Pro
            100                 105                 110
```

```
Ser Gln Ile Ser Gly Leu Pro Thr Arg Tyr Leu Thr Ser Tyr Arg Lys
            115                 120                 125

Lys Thr Val Leu Gly Ala Asp Ser Gln Arg Arg Ser Pro Ser Thr Gly
130                 135                 140

Pro Trp Pro Cys Pro Gln Asp Pro Leu Gly Ala Ala Arg Cys Val Val
145                 150                 155                 160

His Gly Ala Glu Phe Trp Ser Gln Tyr Arg Ile Asn Val Thr Glu Val
                165                 170                 175

Asn Pro Leu Gly Ala Ser Thr Arg Leu Leu Asp Val Ser Leu Gln Ser
            180                 185                 190

Ile Leu Arg Pro Asp Pro Pro Gln Gly Leu Arg Val Glu Ser Val Pro
        195                 200                 205

Gly Tyr Pro Arg Arg Leu Arg Ala Ser Trp Thr Tyr Pro Ala Ser Trp
210                 215                 220

Pro Ser Gln Pro His Phe Leu Leu Lys Phe Arg Leu Gln Tyr Arg Pro
225                 230                 235                 240

Ala Gln His Pro Ala Trp Ser Thr Val Glu Pro Ala Gly Leu Glu Glu
                245                 250                 255

Val Ile Thr Asp Ala Val Ala Gly Leu Pro His Ala Val Arg Val Ser
            260                 265                 270

Ala Arg Asp Phe Leu Asp Ala Gly Thr Trp Ser Thr Trp Ser Pro Glu
        275                 280                 285

Ala Trp Gly Thr Pro Ser Thr Gly Thr Ile Pro Lys Glu Ile Pro Ala
290                 295                 300

Trp Gly Gln Leu His Thr Gln Pro Glu Val Glu Pro Gln Val Asp Ser
305                 310                 315                 320

Pro Ala Pro Pro Arg Pro Ser Leu Gln Pro His Pro Arg Leu Leu Asp
                325                 330                 335

His Arg Asp Ser Val His His His His His His
            340                 345

<210> SEQ ID NO 4
<211> LENGTH: 422
<212> TYPE: PRT
<213> ORGANISM: Homo sapiens

<400> SEQUENCE: 4

Met Ser Ser Ser Cys Ser Gly Leu Ser Arg Val Leu Ala Val Ala
1               5                   10                  15

Thr Ala Leu Val Ser Ala Ser Ser Pro Cys Pro Gln Ala Trp Gly Pro
            20                  25                  30

Pro Gly Val Gln Tyr Gly Gln Pro Gly Arg Ser Val Lys Leu Cys Cys
        35                  40                  45

Pro Gly Val Thr Ala Gly Asp Pro Val Ser Trp Phe Arg Asp Gly Glu
    50                  55                  60

Pro Lys Leu Leu Gln Gly Pro Asp Ser Gly Leu Gly His Glu Leu Val
65                  70                  75                  80

Leu Ala Gln Ala Asp Ser Thr Asp Glu Gly Thr Tyr Ile Cys Gln Thr
                85                  90                  95

Leu Asp Gly Ala Leu Gly Gly Thr Val Thr Leu Gln Leu Gly Tyr Pro
            100                 105                 110

Pro Ala Arg Pro Val Val Ser Cys Gln Ala Ala Asp Tyr Glu Asn Phe
        115                 120                 125

Ser Cys Thr Trp Ser Pro Ser Gln Ile Ser Gly Leu Pro Thr Arg Tyr
    130                 135                 140
```

```
Leu Thr Ser Tyr Arg Lys Lys Thr Val Leu Gly Ala Asp Ser Gln Arg
145                 150                 155                 160

Arg Ser Pro Ser Thr Gly Pro Trp Pro Cys Pro Gln Asp Pro Leu Gly
            165                 170                 175

Ala Ala Arg Cys Val Val His Gly Ala Glu Phe Trp Ser Gln Tyr Arg
        180                 185                 190

Ile Asn Val Thr Glu Val Asn Pro Leu Gly Ala Ser Thr Arg Leu Leu
            195                 200                 205

Asp Val Ser Leu Gln Ser Ile Leu Arg Pro Asp Pro Gln Gly Leu
        210                 215                 220

Arg Val Glu Ser Val Pro Gly Tyr Pro Arg Arg Leu Arg Ala Ser Trp
225                 230                 235                 240

Thr Tyr Pro Ala Ser Trp Pro Cys Gln Pro His Phe Leu Leu Lys Phe
            245                 250                 255

Arg Leu Gln Tyr Arg Pro Ala Gln His Pro Ala Trp Ser Thr Val Glu
            260                 265                 270

Pro Ala Gly Leu Glu Glu Val Ile Thr Asp Ala Val Ala Gly Leu Pro
            275                 280                 285

His Ala Val Arg Val Ser Ala Arg Asp Phe Leu Asp Ala Gly Thr Trp
            290                 295                 300

Ser Thr Trp Ser Pro Glu Ala Trp Gly Thr Pro Ser Thr Gly Thr Ile
305                 310                 315                 320

Pro Lys Glu Ile Pro Ala Trp Gly Gln Leu His Thr Gln Pro Glu Val
                325                 330                 335

Glu Pro Gln Val Asp Ser Pro Ala Pro Arg Pro Ser Leu Gln Pro
            340                 345                 350

His Pro Arg Leu Leu Asp His Arg Asp Ser Val Glu Gln Val Ala Val
            355                 360                 365

Leu Ala Ser Leu Gly Ile Leu Ser Phe Leu Gly Leu Val Ala Gly Ala
            370                 375                 380

Leu Ala Leu Gly Leu Trp Leu Arg Leu Arg Arg Gly Gly Lys Asp Gly
385                 390                 395                 400

Ser Pro Lys Pro Gly Phe Leu Ala Ser Val Ile Pro Val Asp Arg Arg
                405                 410                 415

Pro Gly Ala Pro Asn Leu
            420

<210> SEQ ID NO 5
<211> LENGTH: 107
<212> TYPE: PRT
<213> ORGANISM: Artificial Sequence
<220> FEATURE:
<223> OTHER INFORMATION: amino acid sequence of VL chain of antibody 8E2

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

```
Glu Asp Ile Ala Thr Tyr Tyr Cys Gln Gln Tyr Asp Asn Leu Ser Pro
                85                  90                  95
Thr Phe Gly Pro Gly Thr Lys Val Asp Ile Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: amino acid sequence of VL chain of antibody
      TS-303

<400> SEQUENCE: 6

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Val Asp Tyr Trp
            20                  25                  30
Val Glu Trp Tyr Gln Gln Lys Pro Gly Lys Ala Pro Lys Leu Leu Ile
        35                  40                  45
Tyr Asp Ala Ser Asn Leu Gln Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln Tyr Asp Asn Leu Ser Pro
                85                  90                  95
Thr Phe Gly Pro Gly Thr Lys Val Asp Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: amino acid sequence of VL chain of antibody
      TS-305

<400> SEQUENCE: 7

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Val Gly Ile Tyr
            20                  25                  30
Val Glu Trp Tyr Gln Gln Lys Pro Gly Lys Ala Pro Lys Leu Leu Ile
        35                  40                  45
Tyr Asp Ala Ser Asn Leu Gln Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln Tyr Asp Asn Leu Ser Pro
                85                  90                  95
Thr Phe Gly Pro Gly Thr Lys Val Asp Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: mino acid sequence of VL chain of antibody
      TS-306
```

```
<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Asp Lys Tyr
            20                  25                  30

Val Glu Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Ser Pro
                85                  90                  95

Thr Phe Gly Pro Gly Thr Lys Val Asp Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: amino acid sequence of VL chain of antibody
      TS-307

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Ser Met Tyr
            20                  25                  30

Val Glu Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Ser Pro
                85                  90                  95

Thr Phe Gly Pro Gly Thr Lys Val Asp Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: amino acid sequence of VL chain of antibody
      TS-310

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Ala Met Tyr
            20                  25                  30

Ile Glu Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60
```

-continued

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Ser Pro
                 85                  90                  95

Thr Phe Gly Pro Gly Thr Lys Val Asp Ile Lys
            100                 105

<210> SEQ ID NO 11
<211> LENGTH: 107
<212> TYPE: PRT
<213> ORGANISM: Artificial Sequence
<220> FEATURE:
<223> OTHER INFORMATION: amino acid sequence of VL chain of antibody
      TS-311

<400> SEQUENCE: 11

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Val Ser Gln Tyr
                20                  25                  30

Ile Glu Trp Tyr Gln Gln Lys Pro Gly Lys Ala Pro Lys Leu Leu Ile
            35                  40                  45

Tyr Asp Ala Ser Asn Leu Gln Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Ser Pro
                 85                  90                  95

Thr Phe Gly Pro Gly Thr Lys Val Asp Ile Lys
            100                 105

<210> SEQ ID NO 12
<211> LENGTH: 107
<212> TYPE: PRT
<213> ORGANISM: Artificial Sequence
<220> FEATURE:
<223> OTHER INFORMATION: amino acid sequence of VL chain of antibody
      TS-312

<400> SEQUENCE: 12

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Gly Gln Tyr
                20                  25                  30

Val Glu Trp Tyr Gln Gln Lys Pro Gly Lys Ala Pro Lys Leu Leu Ile
            35                  40                  45

Tyr Asp Ala Ser Asn Leu Gln Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Ser Pro
                 85                  90                  95

Thr Phe Gly Pro Gly Thr Lys Val Asp Ile Lys
            100                 105

<210> SEQ ID NO 13
<211> LENGTH: 107
<212> TYPE: PRT
<213> ORGANISM: Artificial Sequence
<220> FEATURE:
```

<223> OTHER INFORMATION: amino acid sequence of VL chain of antibody
       TS-313

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Ser Gly Tyr
            20                  25                  30

Val Glu Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Ser Pro
                85                  90                  95

Thr Phe Gly Pro Gly Thr Lys Val Asp Ile Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: amino acid sequence of VL chain of antibody
       TS-322

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val His His Tyr
            20                  25                  30

Met Glu Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Ser Pro
                85                  90                  95

Thr Phe Gly Pro Gly Thr Lys Val Asp Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: amino acid sequence of VL chain of antibody
       TS-2

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly

```
                 50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ala Glu Asp Gln Ser Pro
                 85                  90                  95

Thr Phe Gly Pro Gly Thr Lys Val Asp Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: amino acid sequence of VL chain of antibody
      TS-4

<400> SEQUENCE: 16

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Asn Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Gln Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Glu Phe Gln Ser Pro
                 85                  90                  95

Thr Phe Gly Pro Gly Thr Lys Val Asp Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: amino acid sequence of VL chain of antibody
      TS-6

<400> SEQUENCE: 17

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Asn Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Gln Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Glu Gln Phe Glu Ser Gln Ser Pro
                 85                  90                  95

Thr Phe Gly Pro Gly Thr Lys Val Asp Ile Lys
            100                 105

<210> SEQ ID NO 18
<211> LENGTH: 107
<212> TYPE: PRT
```

<213> ORGANISM: Artificial Sequence
<220> FEATURE:
<223> OTHER INFORMATION: amino acid sequence of VL chain of antibody TS-7

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Glu Asn Gln Ser Pro
                85                  90                  95

Thr Phe Gly Pro Gly Thr Lys Val Asp Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: amino acid sequence of VL chain of antibody TS-9

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Glu Glu Gln Ser Pro
                85                  90                  95

Thr Phe Gly Pro Gly Thr Lys Val Asp Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: amino acid sequence of VL chain of antibody TS-13

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

```
Tyr Asp Ala Ser Asn Leu Gln Thr Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Asn Glu Thr Gln Ser Pro
                 85                  90                  95

Thr Phe Gly Pro Gly Thr Lys Val Asp Ile Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: amino acid sequence of VL chain of antibody
      TS-14

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asn Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Gln Thr Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Asp Asn Gln Ser Pro
                 85                  90                  95

Thr Phe Gly Pro Gly Thr Lys Val Asp Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: amino acid sequence of VL chain of antibody
      TS-17

<400> SEQUENCE: 22

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asn Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Gln Thr Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Ser Gln Phe Glu Ser Gln Ser Pro
                 85                  90                  95

Thr Phe Gly Pro Gly Thr Lys Val Asp Ile Lys
            100                 105

<210> SEQ ID NO 23
```

```
<211> LENGTH: 107
<212> TYPE: PRT
<213> ORGANISM: Artificial Sequence
<220> FEATURE:
<223> OTHER INFORMATION: amino acid sequence of VL chain of antibody
      TS-20

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asn Glu Ser Gln Ser Pro
                85                  90                  95

Thr Phe Gly Pro Gly Thr Lys Val Asp Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: amino acid sequence of VL chain of antibody
      TS-21

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Glu Ser Gln Ser Pro
                85                  90                  95

Thr Phe Gly Pro Gly Thr Lys Val Asp Ile Lys
            100                 105

<210> SEQ ID NO 25
<211> LENGTH: 107
<212> TYPE: PRT
<213> ORGANISM: Artificial Sequence
<220> FEATURE:
<223> OTHER INFORMATION: amino acid sequence of VL chain of antibody
      TS-22

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30
```

-continued

Leu Asn Trp Tyr Gln Gln Lys Pro Gly Lys Ala Pro Lys Leu Leu Ile
             35                  40                  45

Tyr Asp Ala Ser Asn Leu Gln Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Phe Glu Thr Gln Ser Pro
                 85                  90                  95

Thr Phe Gly Pro Gly Thr Lys Val Asp Ile Lys
            100                 105

<210> SEQ ID NO 26
<211> LENGTH: 107
<212> TYPE: PRT
<213> ORGANISM: Artificial Sequence
<220> FEATURE:
<223> OTHER INFORMATION: amino acid sequence of VL chain of antibody
      TS-29

<400> SEQUENCE: 26

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asn Asn Tyr
             20                  25                  30

Leu Asn Trp Tyr Gln Gln Lys Pro Gly Lys Ala Pro Lys Leu Leu Ile
             35                  40                  45

Tyr Asp Ala Ser Asn Leu Gln Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ser Glu Glu Gln Ser Pro
                 85                  90                  95

Thr Phe Gly Pro Gly Thr Lys Val Asp Ile Lys
            100                 105

<210> SEQ ID NO 27
<211> LENGTH: 107
<212> TYPE: PRT
<213> ORGANISM: Artificial Sequence
<220> FEATURE:
<223> OTHER INFORMATION: amino acid sequence of VL chain of antibody
      TS-32

<400> SEQUENCE: 27

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asn Asn Tyr
             20                  25                  30

Leu Asn Trp Tyr Gln Gln Lys Pro Gly Lys Ala Pro Lys Leu Leu Ile
             35                  40                  45

Tyr Asp Ala Ser Asn Leu Gln Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Thr Gln Trp Glu Thr Gln Ser Pro
                 85                  90                  95

Thr Phe Gly Pro Gly Thr Lys Val Asp Ile Lys
            100                 105

<210> SEQ ID NO 28
<211> LENGTH: 107
<212> TYPE: PRT
<213> ORGANISM: Artificial Sequence
<220> FEATURE:
<223> OTHER INFORMATION: amino acid sequence of VL chain of antibody TS-49

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Glu Ser Gln Ala Pro
                85                  90                  95

Glu Phe Gly Pro Gly Thr Lys Val Asp Ile Lys
            100                 105

<210> SEQ ID NO 29
<211> LENGTH: 107
<212> TYPE: PRT
<213> ORGANISM: Artificial Sequence
<220> FEATURE:
<223> OTHER INFORMATION: amino acid sequence of VL chain of antibody TS-51

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Glu Ser Gln Trp Pro
                85                  90                  95

Phe Phe Gly Pro Gly Thr Lys Val Asp Ile Lys
            100                 105

<210> SEQ ID NO 30
<211> LENGTH: 107
<212> TYPE: PRT
<213> ORGANISM: Artificial Sequence
<220> FEATURE:
<223> OTHER INFORMATION: amino acid sequence of VL chain of antibody TS-55

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr

```
            20                  25                  30

Leu Asn Trp Tyr Gln Gln Lys Pro Gly Lys Ala Pro Lys Leu Leu Ile
            35                  40                  45

Tyr Asp Ala Ser Asn Leu Gln Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Glu Thr Gln Thr Pro
                85                  90                  95

Ala Phe Gly Pro Gly Thr Lys Val Asp Ile Lys
            100                 105

<210> SEQ ID NO 31
<211> LENGTH: 107
<212> TYPE: PRT
<213> ORGANISM: Artificial Sequence
<220> FEATURE:
<223> OTHER INFORMATION: amino acid sequence of VL chain of antibody
      TS-57

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
            35                  40                  45

Tyr Asp Ala Ser Asn Leu Gln Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Glu Thr Gln Met Pro
                85                  90                  95

Leu Phe Gly Pro Gly Thr Lys Val Asp Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: amino acid sequence of VL chain of antibody
      TS-58

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
            35                  40                  45

Tyr Asp Ala Ser Asn Leu Gln Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Glu Thr Gln Gln Pro
                85                  90                  95

Phe Phe Gly Pro Gly Thr Lys Val Asp Ile Lys
```

```
                100                 105

<210> SEQ ID NO 33
<211> LENGTH: 107
<212> TYPE: PRT
<213> ORGANISM: Artificial Sequence
<220> FEATURE:
<223> OTHER INFORMATION: amino acid sequence of VL chain of antibody
      TS-63

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Thr Gln Gln Pro
                85                  90                  95

Asn Phe Gly Pro Gly Thr Lys Val Asp Ile Lys
            100                 105

<210> SEQ ID NO 34
<211> LENGTH: 107
<212> TYPE: PRT
<213> ORGANISM: Artificial Sequence
<220> FEATURE:
<223> OTHER INFORMATION: amino acid sequence of VL chain of antibody
      TS-64

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Glu Ser Gln Trp Pro
                85                  90                  95

Gln Phe Gly Pro Gly Thr Lys Val Asp Ile Lys
            100                 105

<210> SEQ ID NO 35
<211> LENGTH: 107
<212> TYPE: PRT
<213> ORGANISM: Artificial Sequence
<220> FEATURE:
<223> OTHER INFORMATION: amino acid sequence of consensus of VL chain
      of 8E2 antibody and derivatives
<220> FEATURE:
<221> NAME/KEY: VARIANT
<222> LOCATION: (29)..(29)
<223> OTHER INFORMATION: X=I or V
<220> FEATURE:
```

```
<221> NAME/KEY: VARIANT
<222> LOCATION: (30)..(30)
<223> OTHER INFORMATION: X=N or D or G or S or A or H
<220> FEATURE:
<221> NAME/KEY: VARIANT
<222> LOCATION: (31)..(31)
<223> OTHER INFORMATION: X=N or Y or I or K or M or Q or G or H
<220> FEATURE:
<221> NAME/KEY: VARIANT
<222> LOCATION: (32)..(32)
<223> OTHER INFORMATION: X=Y or W
<220> FEATURE:
<221> NAME/KEY: VARIANT
<222> LOCATION: (33)..(33)
<223> OTHER INFORMATION: X=L or V or I or M
<220> FEATURE:
<221> NAME/KEY: VARIANT
<222> LOCATION: (34)..(34)
<223> OTHER INFORMATION: X=N or E
<220> FEATURE:
<221> NAME/KEY: VARIANT
<222> LOCATION: (89)..(89)
<223> OTHER INFORMATION: X=Q or E or S or T
<220> FEATURE:
<221> NAME/KEY: VARIANT
<222> LOCATION: (91)..(91)
<223> OTHER INFORMATION: X=Y or A or H or F or N or S or W
<220> FEATURE:
<221> NAME/KEY: VARIANT
<222> LOCATION: (92)..(92)
<223> OTHER INFORMATION: X=D or E
<220> FEATURE:
<221> NAME/KEY: VARIANT
<222> LOCATION: (93)..(93)
<223> OTHER INFORMATION: X=N or D or F or S or E or T
<220> FEATURE:
<221> NAME/KEY: VARIANT
<222> LOCATION: (94)..(94)
<223> OTHER INFORMATION: X=L or Q
<220> FEATURE:
<221> NAME/KEY: VARIANT
<222> LOCATION: (95)..(95)
<223> OTHER INFORMATION: X=S or A or W or T or M or Q
<220> FEATURE:
<221> NAME/KEY: VARIANT
<222> LOCATION: (97)..(97)
<223> OTHER INFORMATION: X=T or E or F or A or L or N or Q

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Xaa Xaa Xaa Xaa
            20                  25                  30

Xaa Xaa Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Xaa Gln Xaa Xaa Xaa Xaa Xaa Pro
                85                  90                  95

Xaa Phe Gly Pro Gly Thr Lys Val Asp Ile Lys
            100                 105

<210> SEQ ID NO 36
<211> LENGTH: 107
<212> TYPE: PRT
<213> ORGANISM: Artificial Sequence
<220> FEATURE:
<223> OTHER INFORMATION: amino acid sequence of consensus of VL chain
      of 8E2 antibody and select derivatives
```

```
<220> FEATURE:
<221> NAME/KEY: VARIANT
<222> LOCATION: (29)..(29)
<223> OTHER INFORMATION: X=I or V
<220> FEATURE:
<221> NAME/KEY: VARIANT
<222> LOCATION: (30)..(30)
<223> OTHER INFORMATION: X=D or N
<220> FEATURE:
<221> NAME/KEY: VARIANT
<222> LOCATION: (31)..(31)
<223> OTHER INFORMATION: X=K or N
<220> FEATURE:
<221> NAME/KEY: VARIANT
<222> LOCATION: (33)..(33)
<223> OTHER INFORMATION: X=L or V
<220> FEATURE:
<221> NAME/KEY: VARIANT
<222> LOCATION: (34)..(34)
<223> OTHER INFORMATION: X=N or E
<220> FEATURE:
<221> NAME/KEY: VARIANT
<222> LOCATION: (91)..(91)
<223> OTHER INFORMATION: X=Y or A or H
<220> FEATURE:
<221> NAME/KEY: VARIANT
<222> LOCATION: (92)..(92)
<223> OTHER INFORMATION: X=D or E
<220> FEATURE:
<221> NAME/KEY: VARIANT
<222> LOCATION: (93)..(93)
<223> OTHER INFORMATION: X=N or D or F or N or S
<220> FEATURE:
<221> NAME/KEY: VARIANT
<222> LOCATION: (94)..(94)
<223> OTHER INFORMATION: X=L or Q
<220> FEATURE:
<221> NAME/KEY: VARIANT
<222> LOCATION: (95)..(95)
<223> OTHER INFORMATION: X=S or W
<220> FEATURE:
<221> NAME/KEY: VARIANT
<222> LOCATION: (97)..(97)
<223> OTHER INFORMATION: X=T or F

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Xaa Xaa Xaa Tyr
            20                  25                  30

Xaa Xaa Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Xaa Xaa Xaa Xaa Xaa Pro
                85                  90                  95

Xaa Phe Gly Pro Gly Thr Lys Val Asp Ile Lys
            100                 105

<210> SEQ ID NO 37
<211> LENGTH: 118
<212> TYPE: PRT
<213> ORGANISM: Artificial Sequence
<220> FEATURE:
<223> OTHER INFORMATION: amino acid sequence of VH chain of antibody
      8E2

<400> SEQUENCE: 37
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Pro Gly Trp Gly Ser Phe Asp Leu Trp Gly Arg Gly Thr
            100                 105                 110

Leu Val Thr Val Ser Ser
        115

<210> SEQ ID NO 38
<211> LENGTH: 118
<212> TYPE: PRT
<213> ORGANISM: Artificial Sequence
<220> FEATURE:
<223> OTHER INFORMATION: amino acid sequence of VH chain of antibody
      TS-66

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Trp Trp
            20                  25                  30

Ser Ile Ala Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Pro Gly Trp Gly Ser Phe Asp Leu Trp Gly Arg Gly Thr
            100                 105                 110

Leu Val Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: amino acid sequence of VH chain of antibody
      TS-69

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Trp Trp
            20                  25                  30

Ser Val Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
     50                  55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                 85                  90                  95

Ala Lys Gly Pro Gly Trp Gly Ser Phe Asp Leu Trp Gly Arg Gly Thr
            100                 105                 110

Leu Val Thr Val Ser Ser
            115

<210> SEQ ID NO 40
<211> LENGTH: 118
<212> TYPE: PRT
<213> ORGANISM: Artificial Sequence
<220> FEATURE:
<223> OTHER INFORMATION: amino acid sequence of VH chain of antibody
      TS-71

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Arg Trp
            20                  25                  30

Ser Thr Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Ser Phe Asp Leu Trp Gly Arg Gly Thr
            100                 105                 110

Leu Val Thr Val Ser Ser
            115

<210> SEQ ID NO 41
<211> LENGTH: 118
<212> TYPE: PRT
<213> ORGANISM: Artificial Sequence
<220> FEATURE:
<223> OTHER INFORMATION: amino acid sequence of VH chain of antibody
      TS-76

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Arg Trp
            20                  25                  30

Ser Ile Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Ser Phe Asp Leu Trp Gly Arg Gly Thr
            100                 105                 110

Leu Val Thr Val Ser Ser
        115

<210> SEQ ID NO 42
<211> LENGTH: 118
<212> TYPE: PRT
<213> ORGANISM: Artificial Sequence
<220> FEATURE:
<223> OTHER INFORMATION: amino acid sequence of VH chain of antibody
      TS-79

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Trp Phe
            20                  25                  30

Ser Val Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Ser Phe Asp Leu Trp Gly Arg Gly Thr
            100                 105                 110

Leu Val Thr Val Ser Ser
        115

<210> SEQ ID NO 43
<211> LENGTH: 118
<212> TYPE: PRT
<213> ORGANISM: Artificial Sequence
<220> FEATURE:
<223> OTHER INFORMATION: amino acid sequence of VH chain of antibody
      TS-82

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Arg Trp
            20                  25                  30

Ser Val Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Ser Phe Asp Leu Trp Gly Arg Gly Thr
            100                 105                 110

Leu Val Thr Val Ser Ser
        115

<210> SEQ ID NO 44
<211> LENGTH: 118

```
<212> TYPE: PRT
<213> ORGANISM: Artificial Sequence
<220> FEATURE:
<223> OTHER INFORMATION: amino acid sequence of VH chain of antibody
      TS-88

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Arg Trp
            20                  25                  30

Ser Thr Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Ser Phe Asp Leu Trp Gly Arg Gly Thr
            100                 105                 110

Leu Val Thr Val Ser Ser
        115

<210> SEQ ID NO 45
<211> LENGTH: 118
<212> TYPE: PRT
<213> ORGANISM: Artificial Sequence
<220> FEATURE:
<223> OTHER INFORMATION: amino acid sequence of VH chain of antibody
      TS-89

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Arg Trp
            20                  25                  30

Ser Ile Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Ser Phe Asp Leu Trp Gly Arg Gly Thr
            100                 105                 110

Leu Val Thr Val Ser Ser
        115

<210> SEQ ID NO 46
<211> LENGTH: 118
<212> TYPE: PRT
<213> ORGANISM: Artificial Sequence
<220> FEATURE:
<223> OTHER INFORMATION: amino acid sequence of VH chain of antibody
      TS-91

<400> SEQUENCE: 46

Glu Val Gln Leu Leu Glu Ser Gly Gly Gly Leu Val Gln Pro Gly Gly
```

-continued

```
                1               5                      10                      15
Ser Leu Arg Leu Ser Cys Ala Ala Ser Gly Phe Thr Phe Gly Trp Trp
                    20                      25                      30
Ser Leu Thr Trp Val Arg Gln Ala Pro Gly Lys Gly Leu Glu Trp Val
                    35                      40                      45
Ser Ser Ile Val Pro Ser Gly Gly His Thr Gln Tyr Ala Asp Ser Val
            50                      55                      60
Lys Gly Arg Phe Thr Ile Ser Arg Asp Asn Ser Lys Asn Thr Leu Tyr
 65                      70                      75                      80
Leu Gln Met Asn Ser Leu Arg Ala Glu Asp Thr Ala Val Tyr Tyr Cys
                            85                      90                      95
Ala Lys Gly Pro Gly Trp Gly Ser Phe Asp Leu Trp Gly Arg Gly Thr
                    100                     105                     110
Leu Val Thr Val Ser Ser
            115
```

<210> SEQ ID NO 47
<211> LENGTH: 118
<212> TYPE: PRT
<213> ORGANISM: Artificial Sequence
<220> FEATURE:
<223> OTHER INFORMATION: amino acid sequence of VH chain of antibody
      TS-92

<400> SEQUENCE: 47

```
Glu Val Gln Leu Leu Glu Ser Gly Gly Gly Leu Val Gln Pro Gly Gly
 1               5                      10                      15
Ser Leu Arg Leu Ser Cys Ala Ala Ser Gly Phe Thr Phe Ser Trp Trp
                    20                      25                      30
Ser Ile Thr Trp Val Arg Gln Ala Pro Gly Lys Gly Leu Glu Trp Val
                    35                      40                      45
Ser Ser Ile Val Pro Ser Gly Gly His Thr Gln Tyr Ala Asp Ser Val
            50                      55                      60
Lys Gly Arg Phe Thr Ile Ser Arg Asp Asn Ser Lys Asn Thr Leu Tyr
 65                      70                      75                      80
Leu Gln Met Asn Ser Leu Arg Ala Glu Asp Thr Ala Val Tyr Tyr Cys
                            85                      90                      95
Ala Lys Gly Pro Gly Trp Gly Ser Phe Asp Leu Trp Gly Arg Gly Thr
                    100                     105                     110
Leu Val Thr Val Ser Ser
            115
```

<210> SEQ ID NO 48
<211> LENGTH: 118
<212> TYPE: PRT
<213> ORGANISM: Artificial Sequence
<220> FEATURE:
<223> OTHER INFORMATION: amino acid sequence of VH chain of antibody
      TS-97

<400> SEQUENCE: 48

```
Glu Val Gln Leu Leu Glu Ser Gly Gly Gly Leu Val Gln Pro Gly Gly
 1               5                      10                      15
Ser Leu Arg Leu Ser Cys Ala Ala Ser Gly Phe Thr Phe Ser Trp Tyr
                    20                      25                      30
Ser Met Thr Trp Val Arg Gln Ala Pro Gly Lys Gly Leu Glu Trp Val
                    35                      40                      45
Ser Ser Ile Val Pro Trp Ala Asp Tyr Thr Gln Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Pro Gly Trp Gly Ser Phe Asp Leu Trp Gly Arg Gly Thr
                100                 105                 110

Leu Val Thr Val Ser Ser
            115

<210> SEQ ID NO 49
<211> LENGTH: 118
<212> TYPE: PRT
<213> ORGANISM: Artificial Sequence
<220> FEATURE:
<223> OTHER INFORMATION: amino acid sequence of VH chain of antibody
      TS-101

<400> SEQUENCE: 49

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
             20                  25                  30

Ser Met Thr Trp Val Arg Gln Ala Pro Gly Lys Gly Leu Glu Trp Val
         35                  40                  45

Ser Ser Ile Val Pro Trp Gly Asp Leu Thr Gln Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Pro Gly Trp Gly Ser Phe Asp Leu Trp Gly Arg Gly Thr
                100                 105                 110

Leu Val Thr Val Ser Ser
            115

<210> SEQ ID NO 50
<211> LENGTH: 118
<212> TYPE: PRT
<213> ORGANISM: Artificial Sequence
<220> FEATURE:
<223> OTHER INFORMATION: amino acid sequence of VH chain of antibody
      TS-103

<400> SEQUENCE: 50

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
             20                  25                  30

Ser Met Thr Trp Val Arg Gln Ala Pro Gly Lys Gly Leu Glu Trp Val
         35                  40                  45

Ser Ser Ile Val Pro Tyr Gly Asp Leu Thr Gln Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Pro Gly Trp Gly Ser Phe Asp Leu Trp Gly Arg Gly Thr
```

Leu Val Thr Val Ser Ser
        115

<210> SEQ ID NO 51
<211> LENGTH: 118
<212> TYPE: PRT
<213> ORGANISM: Artificial Sequence
<220> FEATURE:
<223> OTHER INFORMATION: amino acid sequence of VH chain of antibody
      TS-104

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
        35                  40                  45

Ser Ser Ile Val Pro Trp Gly Thr Ile Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Ser Phe Asp Leu Trp Gly Arg Gly Thr
            100                 105                 110

Leu Val Thr Val Ser Ser
        115

<210> SEQ ID NO 52
<211> LENGTH: 118
<212> TYPE: PRT
<213> ORGANISM: Artificial Sequence
<220> FEATURE:
<223> OTHER INFORMATION: amino acid sequence of VH chain of antibody
      TS-107

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
        35                  40                  45

Ser Ser Ile Val Pro Trp Gly Asp Phe Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Ser Phe Asp Leu Trp Gly Arg Gly Thr
            100                 105                 110

Leu Val Thr Val Ser Ser
        115

<210> SEQ ID NO 53
<211> LENGTH: 118
<212> TYPE: PRT

```
<213> ORGANISM: Artificial Sequence
<220> FEATURE:
<223> OTHER INFORMATION: amino acid sequence of VH chain of antibody
      TS-108

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
        35                  40                  45

Ser Ser Ile Val Pro Trp Gly Thr Leu Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Ser Phe Asp Leu Trp Gly Arg Gly Thr
            100                 105                 110

Leu Val Thr Val Ser Ser
        115

<210> SEQ ID NO 54
<211> LENGTH: 118
<212> TYPE: PRT
<213> ORGANISM: Artificial Sequence
<220> FEATURE:
<223> OTHER INFORMATION: amino acid sequence of VH chain of antibody
      TS-115

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
        35                  40                  45

Ser Ser Ile Val Pro His Gly Asp Leu Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Ser Phe Asp Leu Trp Gly Arg Gly Thr
            100                 105                 110

Leu Val Thr Val Ser Ser
        115

<210> SEQ ID NO 55
<211> LENGTH: 118
<212> TYPE: PRT
<213> ORGANISM: Artificial Sequence
<220> FEATURE:
<223> OTHER INFORMATION: amino acid sequence of VH chain of antibody
      TS-129

<400> SEQUENCE: 55

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Trp Tyr
        20                  25                  30

Ser Met Thr Trp Val Arg Gln Ala Pro Gly Lys Gly Leu Glu Trp Val
            35                  40                  45

Ser Ser Ile Val Pro Ser Gly Gly His Thr Gln Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Pro Glu Asp Trp Gly Met Phe Asp Leu Trp Gly Arg Gly Thr
            100                 105                 110

Leu Val Thr Val Ser Ser
        115

<210> SEQ ID NO 56
<211> LENGTH: 118
<212> TYPE: PRT
<213> ORGANISM: Artificial Sequence
<220> FEATURE:
<223> OTHER INFORMATION: amino acid sequence of VH chain of antibody
      TS-133

<400> SEQUENCE: 56

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
        20                  25                  30

Ser Met Thr Trp Val Arg Gln Ala Pro Gly Lys Gly Leu Glu Trp Val
            35                  40                  45

Ser Ser Ile Val Pro Ser Gly Gly His Thr Gln Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Pro Val Asp Trp Gly Arg Phe Asp Leu Trp Gly Arg Gly Thr
            100                 105                 110

Leu Val Thr Val Ser Ser
        115

<210> SEQ ID NO 57
<211> LENGTH: 118
<212> TYPE: PRT
<213> ORGANISM: Artificial Sequence
<220> FEATURE:
<223> OTHER INFORMATION: amino acid sequence of VH chain of antibody
      TS-134

<400> SEQUENCE: 57

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
        20                  25                  30

Ser Met Thr Trp Val Arg Gln Ala Pro Gly Lys Gly Leu Glu Trp Val
            35                  40                  45

Ser Ser Ile Val Pro Ser Gly Gly His Thr Gln Tyr Ala Asp Ser Val
 50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Glu Asp Trp Gly Leu Phe Asp Leu Trp Gly Arg Gly Thr
            100                 105                 110

Leu Val Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: amino acid sequence of VH chain of antibody
      TS-135

<400> SEQUENCE: 58

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
             20                  25                  30

Ser Met Thr Trp Val Arg Gln Ala Pro Gly Lys Gly Leu Glu Trp Val
         35                  40                  45

Ser Ser Ile Val Pro Ser Gly Gly His Thr Gln Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Leu Asp Trp Gly Leu Phe Asp Leu Trp Gly Arg Gly Thr
            100                 105                 110

Leu Val Thr Val Ser Ser
        115

<210> SEQ ID NO 59
<211> LENGTH: 118
<212> TYPE: PRT
<213> ORGANISM: Artificial Sequence
<220> FEATURE:
<223> OTHER INFORMATION: amino acid sequence of VH chain of antibody
      TS-136

<400> SEQUENCE: 59

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
             20                  25                  30

Ser Met Thr Trp Val Arg Gln Ala Pro Gly Lys Gly Leu Glu Trp Val
         35                  40                  45

Ser Ser Ile Val Pro Ser Gly Gly His Thr Gln Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Leu Asp Trp Gly Arg Phe Asp Leu Trp Gly Arg Gly Thr
            100                 105                 110
```

```
Leu Val Thr Val Ser Ser
        115

<210> SEQ ID NO 60
<211> LENGTH: 118
<212> TYPE: PRT
<213> ORGANISM: Artificial Sequence
<220> FEATURE:
<223> OTHER INFORMATION: amino acid sequence of VH chain of antibody
      TS-140

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asn Asp Trp Gly Leu Phe Asp Leu Trp Gly Arg Gly Thr
            100                 105                 110

Leu Val Thr Val Ser Ser
        115

<210> SEQ ID NO 61
<211> LENGTH: 118
<212> TYPE: PRT
<213> ORGANISM: Artificial Sequence
<220> FEATURE:
<223> OTHER INFORMATION: amino acid sequence of VH chain of antibody
      TS-143

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Asp Trp Gly Leu Phe Asp Leu Trp Gly Arg Gly Thr
            100                 105                 110

Leu Val Thr Val Ser Ser
        115

<210> SEQ ID NO 62
<211> LENGTH: 118
<212> TYPE: PRT
<213> ORGANISM: Artificial Sequence
```

```
<220> FEATURE:
<223> OTHER INFORMATION: amino acid sequence of VH chain of antibody
      TS-151

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Asp Trp Gly Arg Phe Asp Leu Trp Gly Arg Gly Thr
            100                 105                 110

Leu Val Thr Val Ser Ser
        115

<210> SEQ ID NO 63
<211> LENGTH: 118
<212> TYPE: PRT
<213> ORGANISM: Artificial Sequence
<220> FEATURE:
<223> OTHER INFORMATION: amino acid sequence of VH chain of antibody
      TS-156

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Glu Asp Trp Gly Arg Phe Asp Leu Trp Gly Arg Gly Thr
            100                 105                 110

Leu Val Thr Val Ser Ser
        115

<210> SEQ ID NO 64
<211> LENGTH: 118
<212> TYPE: PRT
<213> ORGANISM: Artificial Sequence
<220> FEATURE:
<223> OTHER INFORMATION: amino acid sequence of VH chain of antibody
      TS-213

<400> SEQUENCE: 64

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
            35                  40                  45

Ser Ser Ile Val Pro Ser Gly Gly His Thr Gln Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Gln Phe Ala Val Trp Gly Arg Gly Thr
            100                 105                 110

Leu Val Thr Val Ser Ser
            115

<210> SEQ ID NO 65
<211> LENGTH: 118
<212> TYPE: PRT
<213> ORGANISM: Artificial Sequence
<220> FEATURE:
<223> OTHER INFORMATION: amino acid sequence of VH chain of antibody
      TS-214

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
            35                  40                  45

Ser Ser Ile Val Pro Ser Gly Gly His Thr Gln Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Ser Phe Trp Phe Trp Gly Arg Gly Thr
            100                 105                 110

Leu Val Thr Val Ser Ser
            115

<210> SEQ ID NO 66
<211> LENGTH: 118
<212> TYPE: PRT
<213> ORGANISM: Artificial Sequence
<220> FEATURE:
<223> OTHER INFORMATION: amino acid sequence of VH chain of antibody
      TS-215

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
            35                  40                  45

Ser Ser Ile Val Pro Ser Gly Gly His Thr Gln Tyr Ala Asp Ser Val
        50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Pro Gly Trp Gly Ser Phe Trp Gln Trp Gly Arg Gly Thr
            100                 105                 110

Leu Val Thr Val Ser Ser
        115
```

<210> SEQ ID NO 67
<211> LENGTH: 118
<212> TYPE: PRT
<213> ORGANISM: Artificial Sequence
<220> FEATURE:
<223> OTHER INFORMATION: amino acid sequence of VH chain of antibody
      TS-218

<400> SEQUENCE: 67

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Pro Gly Trp Gly Ser Phe Trp Glu Trp Gly Arg Gly Thr
            100                 105                 110

Leu Val Thr Val Ser Ser
        115
```

<210> SEQ ID NO 68
<211> LENGTH: 118
<212> TYPE: PRT
<213> ORGANISM: Artificial Sequence
<220> FEATURE:
<223> OTHER INFORMATION: amino acid sequence of VH chain of antibody
      TS-221

<400> SEQUENCE: 68

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Pro Gly Trp Gly Ser Phe Trp Tyr Trp Gly Arg Gly Thr
            100                 105                 110
```

Leu Val Thr Val Ser Ser
        115

<210> SEQ ID NO 69
<211> LENGTH: 118
<212> TYPE: PRT
<213> ORGANISM: Artificial Sequence
<220> FEATURE:
<223> OTHER INFORMATION: amino acid sequence of VH chain of antibody
      TS-222

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Thr Phe Ala Tyr Trp Gly Arg Gly Thr
            100                 105                 110

Leu Val Thr Val Ser Ser
        115

<210> SEQ ID NO 70
<211> LENGTH: 118
<212> TYPE: PRT
<213> ORGANISM: Artificial Sequence
<220> FEATURE:
<223> OTHER INFORMATION: amino acid sequence of VH chain of antibody
      TS-224

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Thr Trp Val Arg Gln Ala Pro Gly Lys Gly Leu Glu Trp Val
        35                  40                  45

Ser Ser Ile Val Pro Ser Gly Gly His Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Trp Gly Ser Phe Trp Thr Trp Gly Arg Gly Thr
            100                 105                 110

Leu Val Thr Val Ser Ser
        115

<210> SEQ ID NO 71
<211> LENGTH: 118
<212> TYPE: PRT
<213> ORGANISM: Artificial Sequence
<220> FEATURE:

```
<223> OTHER INFORMATION: amino acid sequence of consensus of VH chain of
      8E2 antibody and derivatives
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: VARIANT
<222> LOCATION: (31)..(31)
<223> OTHER INFORMATION: X=W or R
<220> FEATURE:
<221> NAME/KEY: VARIANT
<222> LOCATION: (32)..(32)
<223> OTHER INFORMATION: X=Y or W or F
<220> FEATURE:
<221> NAME/KEY: VARIANT
<222> LOCATION: (34)..(34)
<223> OTHER INFORMATION: X=M or I or V or T or L
<220> FEATURE:
<221> NAME/KEY: VARIANT
<222> LOCATION: (35)..(35)
<223> OTHER INFORMATION: X=T or A
<220> FEATURE:
<221> NAME/KEY: VARIANT
<222> LOCATION: (53)..(53)
<223> OTHER INFORMATION: X=S or W or Y or H
<220> FEATURE:
<221> NAME/KEY: VARIANT
<222> LOCATION: (54)..(54)
<223> OTHER INFORMATION: X=G or A
<220> FEATURE:
<221> NAME/KEY: VARIANT
<222> LOCATION: (55)..(55)
<223> OTHER INFORMATION: X=G or D or T
<220> FEATURE:
<221> NAME/KEY: VARIANT
<222> LOCATION: (56)..(56)
<223> OTHER INFORMATION: X=H or Y or L or I or F
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: VARIANT
<222> LOCATION: (99)..(99)
<223> OTHER INFORMATION: X=G or P
<220> FEATURE:
<221> NAME/KEY: VARIANT
<222> LOCATION: (100)..(100)
<223> OTHER INFORMATION: X=P or E or V or L or N or H or E
<220> FEATURE:
<221> NAME/KEY: VARIANT
<222> LOCATION: (101)..(101)
<223> OTHER INFORMATION: X=G or D
<220> FEATURE:
<221> NAME/KEY: VARIANT
<222> LOCATION: (104)..(104)
<223> OTHER INFORMATION: X=S or M or R or L or Q or T
<220> FEATURE:
<221> NAME/KEY: VARIANT
<222> LOCATION: (106)..(106)
<223> OTHER INFORMATION: X=D or A or W
<220> FEATURE:
<221> NAME/KEY: VARIANT
<222> LOCATION: (107)..(107)
<223> OTHER INFORMATION: X=L or V or F or Q or E or Y or T

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Xaa
            20                  25                  30

Ser Xaa Xaa Trp Val Arg Gln Ala Pro Gly Lys Gly Leu Glu Trp Val
        35                  40                  45

Ser Ser Ile Val Pro Xaa Xaa Xaa Xaa Thr Gln Tyr Ala Asp Ser Val
```

```
                        50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Xaa Xaa Xaa Trp Gly Xaa Phe Xaa Xaa Trp Gly Arg Gly Thr
               100                 105                 110

Leu Val Thr Val Ser Ser
        115

<210> SEQ ID NO 72
<211> LENGTH: 118
<212> TYPE: PRT
<213> ORGANISM: Artificial Sequence
<220> FEATURE:
<223> OTHER INFORMATION: amino acid sequence of consensus of VH chain of
      8E2 antibody and select derivatives
<220> FEATURE:
<221> NAME/KEY: VARIANT
<222> LOCATION: (53)..(53)
<223> OTHER INFORMATION: X=W or S
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: VARIANT
<222> LOCATION: (55)..(55)
<223> OTHER INFORMATION: X=G or D or T
<220> FEATURE:
<221> NAME/KEY: VARIANT
<222> LOCATION: (56)..(56)
<223> OTHER INFORMATION: X=H or L
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: VARIANT
<222> LOCATION: (99)..(99)
<223> OTHER INFORMATION: X=G or P
<220> FEATURE:
<221> NAME/KEY: VARIANT
<222> LOCATION: (100)..(100)
<223> OTHER INFORMATION: X=P or E or L
<220> FEATURE:
<221> NAME/KEY: VARIANT
<222> LOCATION: (101)..(101)
<223> OTHER INFORMATION: X=G or D
<220> FEATURE:
<221> NAME/KEY: VARIANT
<222> LOCATION: (104)..(104)
<223> OTHER INFORMATION: X=S or L or R

<400> SEQUENCE: 72

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
                20                  25                  30

Ser Met Thr Trp Val Arg Gln Ala Pro Gly Lys Gly Leu Glu Trp Val
            35                  40                  45

Ser Ser Ile Val Pro Xaa Gly Xaa Xaa Thr Gln Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Lys Xaa Xaa Xaa Trp Gly Xaa Phe Asp Leu Trp Gly Arg Gly Thr
            100                 105                 110

Leu Val Thr Val Ser Ser
115

<210> SEQ ID NO 73
<211> LENGTH: 114
<212> TYPE: PRT
<213> ORGANISM: Artificial Sequence
<220> FEATURE:
<223> OTHER INFORMATION: amino acid sequence of VL chain of antibody 8E4

<400> SEQUENCE: 73

Gln Ser Ala Leu Thr Gln Pro Pro Ser Ala Ser Gly Ser Pro Gly Gln
1               5                   10                  15

Ser Val Ala Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Leu Ile Tyr Glu Val Thr Lys Arg Pro Ser Gly Val Pro Asp Arg Phe
    50                  55                  60

Ser Gly Ser Lys Ala Gly Asn Thr Ala Ser Leu Thr Val Ser Gly Leu
65                  70                  75                  80

Gln Ala Glu Asp Glu Ala Asp Tyr Tyr Cys Ser Ser Tyr Gly Gly Ser
                85                  90                  95

Asn Asn Ala Gly Val Phe Gly Thr Gly Thr Lys Val Thr Val Leu Gly
            100                 105                 110

Gln Pro

<210> SEQ ID NO 74
<211> LENGTH: 126
<212> TYPE: PRT
<213> ORGANISM: Artificial Sequence
<220> FEATURE:
<223> OTHER INFORMATION: amino acid sequence of VH chain of antibody 8E4

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Phe Met Gly Trp Val Arg Gln Ala Pro Gly Lys Gly Leu Glu Trp Val
        35                  40                  45

Ser Tyr Ile Tyr Pro Ser Gly Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Arg Asp Glu Gly Tyr Cys Ser Ser Thr Ser Cys Tyr Phe Asp Ala
            100                 105                 110

Phe Asp Ile Trp Gly Gln Gly Thr Met Val Thr Val Ser Ser
        115                 120                 125

<210> SEQ ID NO 75
<211> LENGTH: 107
<212> TYPE: PRT
<213> ORGANISM: Artificial Sequence
<220> FEATURE:

```
<223> OTHER INFORMATION: amino acid sequence of VL chain of antibody
      8D10

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Leu His Lys Pro Gly Lys Ala Pro Lys Leu Leu Ile
        35                  40                  45

Tyr Asp Ala Ser Asn Leu Gln Thr Gly Val Pro Ser Arg Phe Ser Gly
50                  55                  60

Ser Gly Ser Gly Thr Asp Phe Thr Phe Thr Ile Thr Ser Leu Gln Pro
65                  70                  75                  80

Glu Asp Phe Gly Thr Tyr Tyr Cys Gln Gln Tyr Asp Thr Leu His Pro
                85                  90                  95

Ser Phe Gly Pro Gly Thr Thr Val Asp Ile Lys
            100                 105

<210> SEQ ID NO 76
<211> LENGTH: 118
<212> TYPE: PRT
<213> ORGANISM: Artificial Sequence
<220> FEATURE:
<223> OTHER INFORMATION: amino acid sequence of VH chain of antibody
      8D10

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Met Met Gly Trp Val Arg Gln Ala Pro Gly Lys Gly Leu Glu Trp Val
        35                  40                  45

Ser Ser Ile Val Pro Ser Gly Gly Ile Thr Ile Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Met Gly Ile Val Ala Thr Asp Trp Gly Gln Gly Thr
            100                 105                 110

Leu Val Thr Val Ser Ser
        115

<210> SEQ ID NO 77
<211> LENGTH: 11
<212> TYPE: PRT
<213> ORGANISM: Artificial Sequence
<220> FEATURE:
<223> OTHER INFORMATION: amino acid sequence of consensus of CDR1 of VL
      chain of 8E2 antibody and derivatives
<220> FEATURE:
<221> NAME/KEY: VARIANT
<222> LOCATION: (6)..(6)
<223> OTHER INFORMATION: X=I or V
<220> FEATURE:
<221> NAME/KEY: VARIANT
<222> LOCATION: (7)..(7)
<223> OTHER INFORMATION: X=N or D or G or S or A or H
<220> FEATURE:
<221> NAME/KEY: VARIANT
```

```
<222> LOCATION: (8)..(8)
<223> OTHER INFORMATION: X=N or Y or I or K or M or Q or G or H
<220> FEATURE:
<221> NAME/KEY: VARIANT
<222> LOCATION: (9)..(9)
<223> OTHER INFORMATION: X=Y or W
<220> FEATURE:
<221> NAME/KEY: VARIANT
<222> LOCATION: (10)..(10)
<223> OTHER INFORMATION: X=L or V or I or M
<220> FEATURE:
<221> NAME/KEY: VARIANT
<222> LOCATION: (11)..(11)
<223> OTHER INFORMATION: X=N or E

<400> SEQUENCE: 77

Gln Ala Ser Gln Asp Xaa Xaa Xaa Xaa Xaa Xaa
1               5                   10

<210> SEQ ID NO 78
<211> LENGTH: 9
<212> TYPE: PRT
<213> ORGANISM: Artificial Sequence
<220> FEATURE:
<223> OTHER INFORMATION: amino acid sequence of consensus of CDR3 of
      VL chain of 8E2 antibody and derivatives
<220> FEATURE:
<221> NAME/KEY: VARIANT
<222> LOCATION: (1)..(1)
<223> OTHER INFORMATION: X=Q or E or S or T
<220> FEATURE:
<221> NAME/KEY: VARIANT
<222> LOCATION: (3)..(3)
<223> OTHER INFORMATION: X=Y or A or H or F or N or S or W
<220> FEATURE:
<221> NAME/KEY: VARIANT
<222> LOCATION: (4)..(4)
<223> OTHER INFORMATION: X=D or E
<220> FEATURE:
<221> NAME/KEY: VARIANT
<222> LOCATION: (5)..(5)
<223> OTHER INFORMATION: X=N or D or F or S or E or T
<220> FEATURE:
<221> NAME/KEY: VARIANT
<222> LOCATION: (6)..(6)
<223> OTHER INFORMATION: X=L or Q
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: VARIANT
<222> LOCATION: (9)..(9)
<223> OTHER INFORMATION: X=T or F or A or L or N or Q

<400> SEQUENCE: 78

Xaa Gln Xaa Xaa Xaa Xaa Xaa Pro Xaa
1               5

<210> SEQ ID NO 79
<211> LENGTH: 5
<212> TYPE: PRT
<213> ORGANISM: Artificial Sequence
<220> FEATURE:
<223> OTHER INFORMATION: amino acid sequence of consensus of CDR1 of
      VH chain of 8E2 antibody and derivatives
<220> FEATURE:
<221> NAME/KEY: VARIANT
<222> LOCATION: (1)..(1)
<223> OTHER INFORMATION: X=W or R
<220> FEATURE:
<221> NAME/KEY: VARIANT
<222> LOCATION: (2)..(2)
<223> OTHER INFORMATION: X=Y or W or F
<220> FEATURE:
```

```
<221> NAME/KEY: VARIANT
<222> LOCATION: (4)..(4)
<223> OTHER INFORMATION: X=M or I or V or T or L
<220> FEATURE:
<221> NAME/KEY: VARIANT
<222> LOCATION: (5)..(5)
<223> OTHER INFORMATION: X=T or A

<400> SEQUENCE: 79

Xaa Xaa Ser Xaa Xaa
1               5

<210> SEQ ID NO 80
<211> LENGTH: 17
<212> TYPE: PRT
<213> ORGANISM: Artificial Sequence
<220> FEATURE:
<223> OTHER INFORMATION: amino acid sequence of consensus of CDR2 of
      VH chain of 8E2 antibody and derivatives
<220> FEATURE:
<221> NAME/KEY: VARIANT
<222> LOCATION: (5)..(5)
<223> OTHER INFORMATION: X=S or W or Y or H
<220> FEATURE:
<221> NAME/KEY: VARIANT
<222> LOCATION: (6)..(6)
<223> OTHER INFORMATION: X=G or A
<220> FEATURE:
<221> NAME/KEY: VARIANT
<222> LOCATION: (7)..(7)
<223> OTHER INFORMATION: X=G or D or T
<220> FEATURE:
<221> NAME/KEY: VARIANT
<222> LOCATION: (8)..(8)
<223> OTHER INFORMATION: X=H or Y or L or I or F

<400> SEQUENCE: 80

Ser Ile Val Pro Xaa Xaa Xaa Xaa Thr Gln Tyr Ala Asp Ser Val Lys
1               5                   10                  15

Gly

<210> SEQ ID NO 81
<211> LENGTH: 9
<212> TYPE: PRT
<213> ORGANISM: Artificial Sequence
<220> FEATURE:
<223> OTHER INFORMATION: amino acid sequence of consensus of CDR3 of
      VH chain of 8E2 antibody and derivatives
<220> FEATURE:
<221> NAME/KEY: VARIANT
<222> LOCATION: (1)..(1)
<223> OTHER INFORMATION: X=G or P
<220> FEATURE:
<221> NAME/KEY: VARIANT
<222> LOCATION: (2)..(2)
<223> OTHER INFORMATION: X=P or E or V or L or N or H or E
<220> FEATURE:
<221> NAME/KEY: VARIANT
<222> LOCATION: (3)..(3)
<223> OTHER INFORMATION: X=G or D
<220> FEATURE:
<221> NAME/KEY: VARIANT
<222> LOCATION: (6)..(6)
<223> OTHER INFORMATION: X=S or M or R or L or Q or T
<220> FEATURE:
<221> NAME/KEY: VARIANT
<222> LOCATION: (8)..(8)
<223> OTHER INFORMATION: X=D or A or W
<220> FEATURE:
<221> NAME/KEY: VARIANT
<222> LOCATION: (9)..(9)
<223> OTHER INFORMATION: X=L or V or F or Q or E or Y or T

<400> SEQUENCE: 81
```

```
Xaa Xaa Xaa Trp Gly Xaa Phe Xaa Xaa
1               5
```

<210> SEQ ID NO 82
<211> LENGTH: 424
<212> TYPE: PRT
<213> ORGANISM: Mus musculus

<400> SEQUENCE: 82

```
Met Ser Ser Ser Cys Ser Gly Leu Thr Arg Val Leu Val Ala Val Ala
1               5                   10                  15

Thr Ala Leu Val Ser Ser Ser Pro Cys Pro Gln Ala Trp Gly Pro
            20                  25                  30

Pro Gly Val Gln Tyr Gly Gln Pro Gly Arg Pro Val Met Leu Cys Cys
        35                  40                  45

Pro Gly Val Ser Ala Gly Thr Pro Val Ser Trp Phe Arg Asp Gly Asp
    50                  55                  60

Ser Arg Leu Leu Gln Gly Pro Asp Ser Gly Leu Gly His Arg Leu Val
65                  70                  75                  80

Leu Ala Gln Val Asp Ser Pro Asp Glu Gly Thr Tyr Val Cys Gln Thr
                85                  90                  95

Leu Asp Gly Val Ser Gly Gly Met Val Thr Leu Lys Leu Gly Phe Pro
            100                 105                 110

Pro Ala Arg Pro Glu Val Ser Cys Gln Ala Val Asp Tyr Glu Asn Phe
        115                 120                 125

Ser Cys Thr Trp Ser Pro Gly Gln Val Ser Gly Leu Pro Thr Arg Tyr
    130                 135                 140

Leu Thr Ser Tyr Arg Lys Lys Thr Leu Pro Gly Ala Glu Ser Gln Arg
145                 150                 155                 160

Glu Ser Pro Ser Thr Gly Pro Trp Pro Cys Pro Gln Asp Pro Leu Glu
                165                 170                 175

Ala Ser Arg Cys Val Val His Gly Ala Glu Phe Trp Ser Glu Tyr Arg
            180                 185                 190

Ile Asn Val Thr Glu Val Asn Pro Leu Gly Ala Ser Thr Cys Leu Leu
        195                 200                 205

Asp Val Arg Leu Gln Ser Ile Leu Arg Pro Asp Pro Pro Gln Gly Leu
    210                 215                 220

Arg Val Glu Ser Val Pro Gly Tyr Pro Arg Arg Leu His Ala Ser Trp
225                 230                 235                 240

Thr Tyr Pro Ala Ser Trp Arg Arg Gln Pro His Phe Leu Leu Lys Phe
                245                 250                 255

Arg Leu Gln Tyr Arg Pro Ala Gln His Pro Ala Trp Ser Thr Val Glu
            260                 265                 270

Pro Ile Gly Leu Glu Glu Val Ile Thr Asp Thr Val Ala Gly Leu Pro
        275                 280                 285

His Ala Val Arg Val Ser Ala Arg Asp Phe Leu Asp Ala Gly Thr Trp
    290                 295                 300

Ser Ala Trp Ser Pro Glu Ala Trp Gly Thr Pro Ser Thr Gly Leu Leu
305                 310                 315                 320

Gln Asp Glu Ile Pro Asp Trp Ser Gln Gly His Gly Gln Gln Leu Glu
                325                 330                 335

Ala Val Val Ala Gln Glu Asp Ser Leu Ala Pro Ala Arg Pro Ser Leu
            340                 345                 350

Gln Pro Asp Pro Arg Pro Leu Asp His Arg Asp Pro Leu Glu Gln Val
```

```
                355                 360                 365
Ala Val Leu Ala Ser Leu Gly Ile Phe Ser Cys Leu Gly Leu Ala Val
        370                 375                 380
Gly Ala Leu Ala Leu Gly Leu Trp Leu Arg Leu Arg Arg Ser Gly Lys
385                 390                 395                 400
Glu Gly Pro Gln Lys Pro Gly Leu Leu Ala Pro Met Ile Pro Val Glu
                405                 410                 415
Lys Leu Pro Gly Ile Pro Asn Leu
                420

<210> SEQ ID NO 83
<211> LENGTH: 214
<212> TYPE: PRT
<213> ORGANISM: Artificial Sequence
<220> FEATURE:
<223> OTHER INFORMATION: amino acid sequence of heavy chain of antibody
      8E2

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Thr Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr His Phe Thr Phe Thr Ile Asn Thr Leu Gln Pro
65                  70                  75                  80

Glu Asp Ile Ala Thr Tyr Tyr Cys Gln Gln Tyr Asp Asn Leu Ser Pro
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 84
<211> LENGTH: 302
<212> TYPE: PRT
<213> ORGANISM: Artificial Sequence
<220> FEATURE:
<223> OTHER INFORMATION: amino acid sequence of light chain of antibody
      8E2

<400> SEQUENCE: 84

Glu Val Gln Leu Leu Glu Ser Gly Gly Gly Leu Val Gln Pro Gly Gly
```

```
  1               5                  10                 15
Ser Leu Arg Leu Ser Cys Ala Ala Ser Gly Phe Thr Phe Ser Trp Tyr
                20                 25                 30
Ser Met Thr Trp Val Arg Gln Ala Pro Gly Lys Gly Leu Glu Trp Val
                35                 40                 45
Ser Ser Ile Val Pro Ser Gly Gly His Thr Gln Tyr Ala Asp Ser Val
                50                 55                 60
Lys Gly Arg Phe Thr Ile Ser Arg Asp Asn Ser Lys Asn Thr Leu Tyr
 65                 70                 75                 80
Leu Gln Met Asn Ser Leu Arg Ala Glu Asp Thr Ala Val Tyr Tyr Cys
                85                 90                 95
Ala Lys Gly Pro Gly Trp Gly Ser Phe Asp Leu Trp Gly Arg Gly Thr
                100                105                110
Leu Val Thr Val Ser Ser Ala Ser Thr Lys Gly Pro Ser Val Phe Pro
                115                120                125
Leu Ala Pro Cys Ser Arg Ser Thr Ser Glu Ser Thr Ala Ala Leu Gly
                130                135                140
Cys Leu Val Lys Asp Tyr Phe Pro Glu Pro Val Thr Val Ser Trp Asn
145                150                155                160
Ser Gly Ala Leu Thr Ser Gly Val His Thr Phe Pro Ala Val Leu Gln
                165                170                175
Ser Ser Gly Leu Tyr Ser Leu Ser Ser Val Val Thr Val Pro Ser Ser
                180                185                190
Ser Leu Gly Thr Lys Thr Tyr Thr Cys Asn Val Asp His Lys Pro Ser
                195                200                205
Asn Thr Lys Val Asp Lys Arg Val Glu Ser Lys Tyr Gly Pro Pro Cys
                210                215                220
Pro Pro Cys Pro Ala Pro Glu Phe Leu Gly Gly Pro Ser Val Phe Leu
225                230                235                240
Phe Pro Pro Lys Pro Lys Asp Thr Leu Met Ile Ser Arg Thr Pro Glu
                245                250                255
Val Thr Cys Val Val Val Asp Val Ser Gln Glu Asp Pro Glu Val Gln
                260                265                270
Phe Asn Trp Tyr Val Asp Gly Val Glu Val His Asn Ala Lys Thr Lys
                275                280                285
Pro Arg Glu Glu Gln Phe Asn Ser Thr Tyr Arg Val Val Ser
                290                295                300
```

<210> SEQ ID NO 85
<211> LENGTH: 304
<212> TYPE: PRT
<213> ORGANISM: Artificial Sequence
<220> FEATURE:
<223> OTHER INFORMATION: polypeptide comprising amino acids 23 to 318 of
      Homo sapiens IL-11Rα (SEQ ID NO: 1), a 8xHIS tag and a serine at a
      position corresponding to position 248 of SEQ ID NO:1 (also
      referred to as "WT D1/2")

<400> SEQUENCE: 85

```
Ser Ser Pro Cys Pro Gln Ala Trp Gly Pro Pro Gly Val Gln Tyr Gly
 1               5                  10                 15
Gln Pro Gly Arg Ser Val Lys Leu Cys Cys Pro Gly Val Thr Ala Gly
                20                 25                 30
Asp Pro Val Ser Trp Phe Arg Asp Gly Glu Pro Lys Leu Leu Gln Gly
                35                 40                 45
Pro Asp Ser Gly Leu Gly His Glu Leu Val Leu Ala Gln Ala Asp Ser
```

```
            50                  55                  60
Thr Asp Glu Gly Thr Tyr Ile Cys Gln Thr Leu Asp Gly Ala Leu Gly
 65                  70                  75                  80

Gly Thr Val Thr Leu Gln Leu Gly Tyr Pro Pro Ala Arg Pro Val Val
                 85                  90                  95

Ser Cys Gln Ala Ala Asp Tyr Glu Asn Phe Ser Cys Thr Trp Ser Pro
                100                 105                 110

Ser Gln Ile Ser Gly Leu Pro Thr Arg Tyr Leu Thr Ser Tyr Arg Lys
                115                 120                 125

Lys Thr Val Leu Gly Ala Asp Ser Gln Arg Arg Ser Pro Ser Thr Gly
130                 135                 140

Pro Trp Pro Cys Pro Gln Asp Pro Leu Gly Ala Ala Arg Cys Val Val
145                 150                 155                 160

His Gly Ala Glu Phe Trp Ser Gln Tyr Arg Ile Asn Val Thr Glu Val
                165                 170                 175

Asn Pro Leu Gly Ala Ser Thr Arg Leu Leu Asp Val Ser Leu Gln Ser
                180                 185                 190

Ile Leu Arg Pro Asp Pro Pro Gln Gly Leu Arg Val Glu Ser Val Pro
                195                 200                 205

Gly Tyr Pro Arg Arg Leu Arg Ala Ser Trp Thr Tyr Pro Ala Ser Trp
                210                 215                 220

Pro Ser Gln Pro His Phe Leu Leu Lys Phe Arg Leu Gln Tyr Arg Pro
225                 230                 235                 240

Ala Gln His Pro Ala Trp Ser Thr Val Glu Pro Ala Gly Leu Glu Glu
                245                 250                 255

Val Ile Thr Asp Ala Val Ala Gly Leu Pro His Ala Val Arg Val Ser
                260                 265                 270

Ala Arg Asp Phe Leu Asp Ala Gly Thr Trp Ser Thr Trp Ser Pro Glu
                275                 280                 285

Ala Trp Gly Thr Pro Ser Thr Gly His His His His His His
                290                 295                 300

<210> SEQ ID NO 86
<211> LENGTH: 353
<212> TYPE: PRT
<213> ORGANISM: Artificial Sequence
<220> FEATURE:
<223> OTHER INFORMATION: amino acid sequence of a polypeptide comprising
      amino acids 23-110 of SEQ ID NO: 1 and amino acids 111-367 of SEQ
      ID NO: 82 in which there is a serine at a position corresponding
      to position 206 of SEQ ID NO: 82 and a HIS tag

<400> SEQUENCE: 86

Ser Ser Pro Cys Pro Gln Ala Trp Gly Pro Gly Val Gln Tyr Gly
 1               5                  10                  15

Gln Pro Gly Arg Ser Val Lys Leu Cys Cys Pro Gly Val Thr Ala Gly
                 20                  25                  30

Asp Pro Val Ser Trp Phe Arg Asp Gly Glu Pro Lys Leu Leu Gln Gly
                 35                  40                  45

Pro Asp Ser Gly Leu Gly His Glu Leu Val Leu Ala Gln Ala Asp Ser
 50                  55                  60

Thr Asp Glu Gly Thr Tyr Ile Cys Gln Thr Leu Asp Gly Ala Leu Gly
 65                  70                  75                  80

Gly Thr Val Thr Leu Gln Leu Gly Phe Pro Pro Ala Arg Pro Glu Val
                 85                  90                  95

Ser Cys Gln Ala Val Asp Tyr Glu Asn Phe Ser Cys Thr Trp Ser Pro
```

```
            100                 105                 110
Gly Gln Val Ser Gly Leu Pro Thr Arg Tyr Leu Thr Ser Tyr Arg Lys
            115                 120                 125

Lys Thr Leu Pro Gly Ala Glu Ser Gln Arg Glu Ser Pro Ser Thr Gly
        130                 135                 140

Pro Trp Pro Cys Pro Gln Asp Pro Leu Glu Ala Ser Arg Cys Val Val
145                 150                 155                 160

His Gly Ala Glu Phe Trp Ser Glu Tyr Arg Ile Asn Val Thr Glu Val
                165                 170                 175

Asn Pro Leu Gly Ala Ser Thr Ser Leu Leu Asp Val Arg Leu Gln Ser
            180                 185                 190

Ile Leu Arg Pro Asp Pro Pro Gln Gly Leu Arg Val Glu Ser Val Pro
        195                 200                 205

Gly Tyr Pro Arg Arg Leu His Ala Ser Trp Thr Tyr Pro Ala Ser Trp
    210                 215                 220

Arg Arg Gln Pro His Phe Leu Leu Lys Phe Arg Leu Gln Tyr Arg Pro
225                 230                 235                 240

Ala Gln His Pro Ala Trp Ser Thr Val Glu Pro Ile Gly Leu Glu Glu
                245                 250                 255

Val Ile Thr Asp Ala Val Ala Gly Leu Pro His Ala Val Arg Val Ser
            260                 265                 270

Ala Arg Asp Phe Leu Asp Ala Gly Thr Trp Ser Ala Trp Ser Pro Glu
        275                 280                 285

Ala Trp Gly Thr Pro Ser Thr Gly Pro Leu Gln Asp Glu Ile Pro Asp
    290                 295                 300

Trp Ser Gln Gly His Gly Gln Gln Leu Glu Ala Val Val Ala Gln Glu
305                 310                 315                 320

Asp Ser Pro Ala Pro Ala Arg Pro Ser Leu Gln Pro Asp Pro Arg Pro
                325                 330                 335

Leu Asp His Arg Asp Pro Leu Glu Gln His His His His His His
            340                 345                 350

His
```

```
<210> SEQ ID NO 87
<211> LENGTH: 353
<212> TYPE: PRT
<213> ORGANISM: Artificial Sequence
<220> FEATURE:
<223> OTHER INFORMATION: amino acid sequence of a polypeptide comprising
      amino acids 23-215 of SEQ ID NO: 1 and amino acids 216-367 of SEQ
      ID NO: 82 and a HIS tag

<400> SEQUENCE: 87

Ser Ser Pro Cys Pro Gln Ala Trp Gly Pro Gly Val Gln Tyr Gly
1               5                   10                  15

Gln Pro Gly Arg Ser Val Lys Leu Cys Cys Pro Gly Val Thr Ala Gly
            20                  25                  30

Asp Pro Val Ser Trp Phe Arg Asp Gly Glu Pro Lys Leu Leu Gln Gly
        35                  40                  45

Pro Asp Ser Gly Leu Gly His Glu Leu Val Leu Ala Gln Ala Asp Ser
    50                  55                  60

Thr Asp Glu Gly Thr Tyr Ile Cys Gln Thr Leu Asp Gly Ala Leu Gly
65                  70                  75                  80

Gly Thr Val Thr Leu Gln Leu Gly Tyr Pro Pro Ala Arg Pro Val Val
                85                  90                  95
```

```
Ser Cys Gln Ala Ala Asp Tyr Glu Asn Phe Ser Cys Thr Trp Ser Pro
            100                 105                 110

Ser Gln Ile Ser Gly Leu Pro Thr Arg Tyr Leu Thr Ser Tyr Arg Lys
        115                 120                 125

Lys Thr Val Leu Gly Ala Asp Ser Gln Arg Arg Ser Pro Ser Thr Gly
130                 135                 140

Pro Trp Pro Cys Pro Gln Asp Pro Leu Gly Ala Ala Arg Cys Val Val
145                 150                 155                 160

His Gly Ala Glu Phe Trp Ser Gln Tyr Arg Ile Asn Val Thr Glu Val
                165                 170                 175

Asn Pro Leu Gly Ala Ser Thr Arg Leu Leu Asp Val Ser Leu Gln Ser
            180                 185                 190

Ile Leu Arg Pro Asp Pro Pro Gln Gly Leu Arg Val Glu Ser Val Pro
        195                 200                 205

Gly Tyr Pro Arg Arg Leu His Ala Ser Trp Thr Tyr Pro Ala Ser Trp
    210                 215                 220

Arg Arg Gln Pro His Phe Leu Leu Lys Phe Arg Leu Gln Tyr Arg Pro
225                 230                 235                 240

Ala Gln His Pro Ala Trp Ser Thr Val Glu Pro Ile Gly Leu Glu Glu
                245                 250                 255

Val Ile Thr Asp Ala Val Ala Gly Leu Pro His Ala Val Arg Val Ser
            260                 265                 270

Ala Arg Asp Phe Leu Asp Ala Gly Thr Trp Ser Ala Trp Ser Pro Glu
        275                 280                 285

Ala Trp Gly Thr Pro Ser Thr Gly Pro Leu Gln Asp Glu Ile Pro Asp
290                 295                 300

Trp Ser Gln Gly His Gly Gln Gln Leu Glu Ala Val Val Ala Gln Glu
305                 310                 315                 320

Asp Ser Pro Ala Pro Ala Arg Pro Ser Leu Gln Pro Asp Pro Arg Pro
                325                 330                 335

Leu Asp His Arg Asp Pro Leu Glu Gln His His His His His His
            340                 345                 350

His

<210> SEQ ID NO 88
<211> LENGTH: 353
<212> TYPE: PRT
<213> ORGANISM: Artificial Sequence
<220> FEATURE:
<223> OTHER INFORMATION: amino acid sequence of a polypeptide comprising
      amino acids 23-318 of SEQ ID NO: 1 in which there is a serine at a
      position corresponding to position 226 of SEQ ID NO: 1 and amino
      acids 319-367 of SEQ ID NO: 82 and a HIS tag

<400> SEQUENCE: 88

Ser Ser Pro Cys Pro Gln Ala Trp Gly Pro Pro Gly Val Gln Tyr Gly
1               5                   10                  15

Gln Pro Gly Arg Ser Val Lys Leu Cys Cys Pro Gly Val Thr Ala Gly
            20                  25                  30

Asp Pro Val Ser Trp Phe Arg Asp Gly Glu Pro Lys Leu Leu Gln Gly
        35                  40                  45

Pro Asp Ser Gly Leu Gly His Glu Leu Val Leu Ala Gln Ala Asp Ser
    50                  55                  60

Thr Asp Glu Gly Thr Tyr Ile Cys Gln Thr Leu Asp Gly Ala Leu Gly
65                  70                  75                  80

Gly Thr Val Thr Leu Gln Leu Gly Tyr Pro Pro Ala Arg Pro Val Val
```

```
                        85                  90                  95
Ser Cys Gln Ala Ala Asp Tyr Glu Asn Phe Ser Cys Thr Trp Ser Pro
            100                 105                 110

Ser Gln Ile Ser Gly Leu Pro Thr Arg Tyr Leu Thr Ser Tyr Arg Lys
            115                 120                 125

Lys Thr Val Leu Gly Ala Asp Ser Gln Arg Arg Ser Pro Ser Thr Gly
        130                 135                 140

Pro Trp Pro Cys Pro Gln Asp Pro Leu Gly Ala Ala Arg Cys Val Val
145                 150                 155                 160

His Gly Ala Glu Phe Trp Ser Gln Tyr Arg Ile Asn Val Thr Glu Val
                165                 170                 175

Asn Pro Leu Gly Ala Ser Thr Arg Leu Leu Asp Val Ser Leu Gln Ser
            180                 185                 190

Ile Leu Arg Pro Asp Pro Gln Gly Leu Arg Val Glu Ser Val Pro
        195                 200                 205

Gly Tyr Pro Arg Arg Leu Arg Ala Ser Trp Thr Tyr Pro Ala Ser Trp
    210                 215                 220

Pro Ser Gln Pro His Phe Leu Leu Lys Phe Arg Leu Gln Tyr Arg Pro
225                 230                 235                 240

Ala Gln His Pro Ala Trp Ser Thr Val Glu Pro Ala Gly Leu Glu Glu
                245                 250                 255

Val Ile Thr Asp Ala Val Ala Gly Leu Pro His Ala Val Arg Val Ser
            260                 265                 270

Ala Arg Asp Phe Leu Asp Ala Gly Thr Trp Ser Thr Trp Ser Pro Glu
        275                 280                 285

Ala Trp Gly Thr Pro Ser Thr Gly Pro Leu Gln Asp Glu Ile Pro Asp
        290                 295                 300

Trp Ser Gln Gly His Gly Gln Gln Leu Glu Ala Val Val Ala Gln Glu
305                 310                 315                 320

Asp Ser Pro Ala Pro Ala Arg Pro Ser Leu Gln Pro Asp Pro Arg Pro
                325                 330                 335

Leu Asp His Arg Asp Pro Leu Glu Gln His His His His His His
            340                 345                 350

His

<210> SEQ ID NO 89
<211> LENGTH: 348
<212> TYPE: PRT
<213> ORGANISM: Artificial Sequence
<220> FEATURE:
<223> OTHER INFORMATION: amino acid sequence of a polypeptide comprising
      amino acids 24-215 of SEQ ID NO: 82 in which there is a serine at
      a position corresponding to position 206 of SEQ ID NO: 82 and
      amino acids 216-363 of SEQ ID NO: 1 and a HIS tag

<400> SEQUENCE: 89

Ser Pro Cys Pro Gln Ala Trp Gly Pro Pro Gly Val Gln Tyr Gly Gln
1               5                   10                  15

Pro Gly Arg Pro Val Met Leu Cys Cys Pro Gly Val Ser Ala Gly Thr
            20                  25                  30

Pro Val Ser Trp Phe Arg Asp Gly Asp Ser Arg Leu Leu Gln Gly Pro
        35                  40                  45

Asp Ser Gly Leu Gly His Arg Leu Val Leu Ala Gln Val Asp Ser Pro
    50                  55                  60

Asp Glu Gly Thr Tyr Val Cys Gln Thr Leu Asp Gly Val Ser Gly Gly
65                  70                  75                  80
```

Met Val Thr Leu Lys Leu Gly Phe Pro Pro Ala Arg Pro Glu Val Ser
            85                  90                  95

Cys Gln Ala Val Asp Tyr Glu Asn Phe Ser Cys Thr Trp Ser Pro Gly
            100                 105                 110

Gln Val Ser Gly Leu Pro Thr Arg Tyr Leu Thr Ser Tyr Arg Lys Lys
            115                 120                 125

Thr Leu Pro Gly Ala Glu Ser Gln Arg Glu Ser Pro Ser Thr Gly Pro
130                 135                 140

Trp Pro Cys Pro Gln Asp Pro Leu Glu Ala Ser Arg Cys Val Val His
145                 150                 155                 160

Gly Ala Glu Phe Trp Ser Glu Tyr Arg Ile Asn Val Thr Glu Val Asn
            165                 170                 175

Pro Leu Gly Ala Ser Thr Ser Leu Leu Asp Val Arg Leu Gln Ser Ile
            180                 185                 190

Leu Arg Pro Asp Pro Pro Gln Gly Leu Arg Val Glu Ser Val Pro Gly
            195                 200                 205

Tyr Pro Arg Arg Leu Arg Ala Ser Trp Thr Tyr Pro Ala Ser Trp Pro
            210                 215                 220

Ser Gln Pro His Phe Leu Leu Lys Phe Arg Leu Gln Tyr Arg Pro Ala
225                 230                 235                 240

Gln His Pro Ala Trp Ser Thr Val Glu Pro Ala Gly Leu Glu Glu Val
            245                 250                 255

Ile Thr Asp Ala Val Ala Gly Leu Pro His Ala Val Arg Val Ser Ala
            260                 265                 270

Arg Asp Phe Leu Asp Ala Gly Thr Trp Ser Thr Trp Ser Pro Glu Ala
            275                 280                 285

Trp Gly Thr Pro Ser Thr Gly Thr Ile Pro Lys Glu Ile Pro Ala Trp
            290                 295                 300

Gly Gln Leu His Thr Gln Pro Glu Val Glu Pro Gln Val Asp Ser Pro
305                 310                 315                 320

Ala Pro Pro Arg Pro Ser Leu Gln Pro His Pro Arg Leu Leu Asp His
            325                 330                 335

Arg Asp Ser Val His His His His His His
            340                 345

<210> SEQ ID NO 90
<211> LENGTH: 352
<212> TYPE: PRT
<213> ORGANISM: artificial
<220> FEATURE:
<223> OTHER INFORMATION: amino acid sequence of Mus musculus sIL-11Ra
      comprising amino acids 24 to 367 of SEQ ID NO: 82 comprising a HIS
      tag and a serine at a position corresponding to position 206 of
      SEQ ID NO: 82

<400> SEQUENCE: 90

Ser Pro Cys Pro Gln Ala Trp Gly Pro Gly Val Gln Tyr Gly Gln
1               5                   10                  15

Pro Gly Arg Pro Val Met Leu Cys Cys Pro Gly Val Ser Ala Gly Thr
            20                  25                  30

Pro Val Ser Trp Phe Arg Asp Gly Asp Ser Arg Leu Leu Gln Gly Pro
            35                  40                  45

Asp Ser Gly Leu Gly His Arg Leu Val Leu Ala Gln Val Asp Ser Pro
50                  55                  60

Asp Glu Gly Thr Tyr Val Cys Gln Thr Leu Asp Gly Val Ser Gly Gly
65                  70                  75                  80

Met Val Thr Leu Lys Leu Gly Phe Pro Pro Ala Arg Pro Glu Val Ser
                85                  90                  95
Cys Gln Ala Val Asp Tyr Glu Asn Phe Ser Cys Thr Trp Ser Pro Gly
            100                 105                 110
Gln Val Ser Gly Leu Pro Thr Arg Tyr Leu Thr Ser Tyr Arg Lys Lys
        115                 120                 125
Thr Leu Pro Gly Ala Glu Ser Gln Arg Glu Ser Pro Ser Thr Gly Pro
    130                 135                 140
Trp Pro Cys Pro Gln Asp Pro Leu Glu Ala Ser Arg Cys Val Val His
145                 150                 155                 160
Gly Ala Glu Phe Trp Ser Glu Tyr Arg Ile Asn Val Thr Glu Val Asn
                165                 170                 175
Pro Leu Gly Ala Ser Thr Ser Leu Leu Asp Val Arg Leu Gln Ser Ile
            180                 185                 190
Leu Arg Pro Asp Pro Pro Gln Gly Leu Arg Val Glu Ser Val Pro Gly
        195                 200                 205
Tyr Pro Arg Arg Leu His Ala Ser Trp Thr Tyr Pro Ala Ser Trp Arg
    210                 215                 220
Arg Gln Pro His Phe Leu Leu Lys Phe Arg Leu Gln Tyr Arg Pro Ala
225                 230                 235                 240
Gln His Pro Ala Trp Ser Thr Val Glu Pro Ile Gly Leu Glu Glu Val
                245                 250                 255
Ile Thr Asp Ala Val Ala Gly Leu Pro His Ala Val Arg Val Ser Ala
            260                 265                 270
Arg Asp Phe Leu Asp Ala Gly Thr Trp Ser Ala Trp Ser Pro Glu Ala
        275                 280                 285
Trp Gly Thr Pro Ser Thr Gly Pro Leu Gln Asp Glu Ile Pro Asp Trp
    290                 295                 300
Ser Gln Gly His Gly Gln Leu Glu Ala Val Val Ala Gln Glu Asp
305                 310                 315                 320
Ser Pro Ala Pro Ala Arg Pro Ser Leu Gln Pro Asp Pro Arg Pro Leu
                325                 330                 335
Asp His Arg Asp Pro Leu Glu Gln His His His His His His
            340                 345                 350

<210> SEQ ID NO 91
<211> LENGTH: 217
<212> TYPE: PRT
<213> ORGANISM: Artificial Sequence
<220> FEATURE:
<223> OTHER INFORMATION: amino acid sequence of light chain of antibody
      8E4

<400> SEQUENCE: 91

Gln Ser Ala Leu Thr Gln Pro Pro Ser Ala Ser Gly Ser Pro Gly Gln
1               5                   10                  15
Ser Val Ala Ile Ser Cys Thr Gly Thr Ser Ser Asp Val Gly Gly Tyr
            20                  25                  30
Asn Phe Val Ser Trp Tyr Gln Gln His Pro Gly Lys Ala Pro Lys Leu
        35                  40                  45
Leu Ile Tyr Glu Val Thr Lys Arg Pro Ser Gly Val Pro Asp Arg Phe
    50                  55                  60
Ser Gly Ser Lys Ala Gly Asn Thr Ala Ser Leu Thr Val Ser Gly Leu
65                  70                  75                  80
Gln Ala Glu Asp Glu Ala Asp Tyr Tyr Cys Ser Ser Tyr Gly Gly Ser

```
                        85                  90                  95
Asn Asn Ala Gly Val Phe Gly Thr Gly Thr Lys Val Thr Val Leu Gly
                100                 105                 110

Gln Pro Lys Ala Asn Pro Thr Val Thr Leu Phe Pro Pro Ser Ser Glu
            115                 120                 125

Glu Leu Gln Ala Asn Lys Ala Thr Leu Val Cys Leu Ile Ser Asp Phe
        130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
210                 215
```

<210> SEQ ID NO 92
<211> LENGTH: 453
<212> TYPE: PRT
<213> ORGANISM: Artificial Sequence
<220> FEATURE:
<223> OTHER INFORMATION: amino acid sequence of heavy chain of antibody 8E4

<400> SEQUENCE: 92

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Phe Met Gly Trp Val Arg Gln Ala Pro Gly Lys Gly Leu Glu Trp Val
        35                  40                  45

Ser Tyr Ile Tyr Pro Ser Gly Gly Ser Thr Gly Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Arg Asp Glu Gly Tyr Cys Ser Ser Thr Ser Cys Tyr Phe Asp Ala
                100                 105                 110

Phe Asp Ile Trp Gly Gln Gly Thr Met Val Thr Val Ser Ser Ala Ser
            115                 120                 125

Thr Lys Gly Pro Ser Val Phe Pro Leu Ala Pro Cys Ser Arg Ser Thr
        130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
210                 215                 220
```

```
Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
        450

<210> SEQ ID NO 93
<211> LENGTH: 214
<212> TYPE: PRT
<213> ORGANISM: Artificial Sequence
<220> FEATURE:
<223> OTHER INFORMATION: amino acid sequence of light chain of antibody
      8D10

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Leu His Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Thr Ser Leu Gln Pro
65                  70                  75                  80

Glu Asp Phe Gly Thr Tyr Tyr Cys Gln Gln Tyr Asp Thr Leu His Pro
                85                  90                  95

Ser Phe Gly Pro Gly Thr Thr Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 94
<211> LENGTH: 445
<212> TYPE: PRT
<213> ORGANISM: Artificial Sequence
<220> FEATURE:
<223> OTHER INFORMATION: amino acid sequence of heavy chain of antibody
      8D10

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
                20                  25                  30

Met Met Gly Trp Val Arg Gln Ala Pro Gly Lys Gly Leu Glu Trp Val
            35                  40                  45

Ser Ser Ile Val Pro Ser Gly Gly Ile Thr Ile Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Met Gly Ile Val Ala Thr Asp Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
```

```
                        260                 265                 270
Phe Asn Trp Tyr Val Asp Gly Val Glu Val His Asn Ala Lys Thr Lys
                275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
                435                 440                 445

<210> SEQ ID NO 95
<211> LENGTH: 304
<212> TYPE: PRT
<213> ORGANISM: artificial
<220> FEATURE:
<223> OTHER INFORMATION: amino acid sequence of SEQ ID NO: 85 comprising
      a glutamic acid at a position corresponding to position 117 of SEQ
      ID NO: 1

<400> SEQUENCE: 95

Ser Ser Pro Cys Pro Gln Ala Trp Gly Pro Gly Val Gln Tyr Gly
1               5                   10                  15

Gln Pro Gly Arg Ser Val Lys Leu Cys Cys Pro Gly Val Thr Ala Gly
            20                  25                  30

Asp Pro Val Ser Trp Phe Arg Asp Gly Glu Pro Lys Leu Leu Gln Gly
        35                  40                  45

Pro Asp Ser Gly Leu Gly His Glu Leu Val Leu Ala Gln Ala Asp Ser
    50                  55                  60

Thr Asp Glu Gly Thr Tyr Ile Cys Gln Thr Leu Asp Gly Ala Leu Gly
65                  70                  75                  80

Gly Thr Val Thr Leu Gln Leu Gly Tyr Pro Pro Ala Arg Pro Glu Val
                85                  90                  95

Ser Cys Gln Ala Ala Asp Tyr Glu Asn Phe Ser Cys Thr Trp Ser Pro
            100                 105                 110

Ser Gln Ile Ser Gly Leu Pro Thr Arg Tyr Leu Thr Ser Tyr Arg Lys
        115                 120                 125

Lys Thr Val Leu Gly Ala Asp Ser Gln Arg Arg Ser Pro Ser Thr Gly
130                 135                 140

Pro Trp Pro Cys Pro Gln Asp Pro Leu Gly Ala Ala Arg Cys Val Val
145                 150                 155                 160

His Gly Ala Glu Phe Trp Ser Gln Tyr Arg Ile Asn Val Thr Glu Val
                165                 170                 175
```

```
Asn Pro Leu Gly Ala Ser Thr Arg Leu Leu Asp Val Ser Leu Gln Ser
            180                 185                 190

Ile Leu Arg Pro Asp Pro Pro Gln Gly Leu Arg Val Glu Ser Val Pro
            195                 200                 205

Gly Tyr Pro Arg Arg Leu Arg Ala Ser Trp Thr Tyr Pro Ala Ser Trp
    210                 215                 220

Pro Cys Gln Pro His Phe Leu Leu Lys Phe Arg Leu Gln Tyr Arg Pro
225                 230                 235                 240

Ala Gln His Pro Ala Trp Ser Thr Val Glu Pro Ala Gly Leu Glu Glu
                245                 250                 255

Val Ile Thr Asp Ala Val Ala Gly Leu Pro His Ala Val Arg Val Ser
            260                 265                 270

Ala Arg Asp Phe Leu Asp Ala Gly Thr Trp Ser Thr Trp Ser Pro Glu
            275                 280                 285

Ala Trp Gly Thr Pro Ser Thr Gly His His His His His His
    290                 295                 300

<210> SEQ ID NO 96
<211> LENGTH: 304
<212> TYPE: PRT
<213> ORGANISM: artificial
<220> FEATURE:
<223> OTHER INFORMATION: amino acid sequence of SEQ ID NO: 85 comprising
      an arginine at a position corresponding to position 66 of SEQ ID
      NO: 1

<400> SEQUENCE: 96

Ser Ser Pro Cys Pro Gln Ala Trp Gly Pro Gly Val Gln Tyr Gly
1               5                   10                  15

Gln Pro Gly Arg Ser Val Lys Leu Cys Cys Pro Gly Val Thr Ala Gly
            20                  25                  30

Asp Pro Val Ser Trp Phe Arg Asp Gly Glu Pro Arg Leu Leu Gln Gly
            35                  40                  45

Pro Asp Ser Gly Leu Gly His Glu Leu Val Leu Ala Gln Ala Asp Ser
50                  55                  60

Thr Asp Glu Gly Thr Tyr Ile Cys Gln Thr Leu Asp Gly Ala Leu Gly
65                  70                  75                  80

Gly Thr Val Thr Leu Gln Leu Gly Tyr Pro Pro Ala Arg Pro Val Val
            85                  90                  95

Ser Cys Gln Ala Ala Asp Tyr Glu Asn Phe Ser Cys Thr Trp Ser Pro
            100                 105                 110

Ser Gln Ile Ser Gly Leu Pro Thr Arg Tyr Leu Thr Ser Tyr Arg Lys
            115                 120                 125

Lys Thr Val Leu Gly Ala Asp Ser Gln Arg Arg Ser Pro Ser Thr Gly
    130                 135                 140

Pro Trp Pro Cys Pro Gln Asp Pro Leu Gly Ala Ala Arg Cys Val Val
145                 150                 155                 160

His Gly Ala Glu Phe Trp Ser Gln Tyr Arg Ile Asn Val Thr Glu Val
                165                 170                 175

Asn Pro Leu Gly Ala Ser Thr Arg Leu Leu Asp Val Ser Leu Gln Ser
            180                 185                 190

Ile Leu Arg Pro Asp Pro Pro Gln Gly Leu Arg Val Glu Ser Val Pro
            195                 200                 205

Gly Tyr Pro Arg Arg Leu Arg Ala Ser Trp Thr Tyr Pro Ala Ser Trp
    210                 215                 220
```

```
Pro Cys Gln Pro His Phe Leu Leu Lys Phe Arg Leu Gln Tyr Arg Pro
225                 230                 235                 240

Ala Gln His Pro Ala Trp Ser Thr Val Glu Pro Ala Gly Leu Glu Glu
                245                 250                 255

Val Ile Thr Asp Ala Val Ala Gly Leu Pro His Ala Val Arg Val Ser
            260                 265                 270

Ala Arg Asp Phe Leu Asp Ala Gly Thr Trp Ser Thr Trp Ser Pro Glu
        275                 280                 285

Ala Trp Gly Thr Pro Ser Thr Gly His His His His His His
    290                 295                 300
```

<210> SEQ ID NO 97
<211> LENGTH: 304
<212> TYPE: PRT
<213> ORGANISM: artificial
<220> FEATURE:
<223> OTHER INFORMATION: amino acid sequence of SEQ ID NO: 85 comprising a serine at a position corresponding to position 65 of SEQ ID NO: 1

<400> SEQUENCE: 97

```
Ser Ser Pro Cys Pro Gln Ala Trp Gly Pro Gly Val Gln Tyr Gly
1               5                   10                  15

Gln Pro Gly Arg Ser Val Lys Leu Cys Cys Pro Gly Val Thr Ala Gly
                20                  25                  30

Asp Pro Val Ser Trp Phe Arg Asp Gly Glu Ser Lys Leu Leu Gln Gly
            35                  40                  45

Pro Asp Ser Gly Leu Gly His Glu Leu Val Leu Ala Gln Ala Asp Ser
        50                  55                  60

Thr Asp Glu Gly Thr Tyr Ile Cys Gln Thr Leu Asp Gly Ala Leu Gly
65                  70                  75                  80

Gly Thr Val Thr Leu Gln Leu Gly Tyr Pro Pro Ala Arg Pro Val Val
                85                  90                  95

Ser Cys Gln Ala Ala Asp Tyr Glu Asn Phe Ser Cys Thr Trp Ser Pro
                100                 105                 110

Ser Gln Ile Ser Gly Leu Pro Thr Arg Tyr Leu Thr Ser Tyr Arg Lys
            115                 120                 125

Lys Thr Val Leu Gly Ala Asp Ser Gln Arg Arg Ser Pro Ser Thr Gly
        130                 135                 140

Pro Trp Pro Cys Pro Gln Asp Pro Leu Gly Ala Ala Arg Cys Val Val
145                 150                 155                 160

His Gly Ala Glu Phe Trp Ser Gln Tyr Arg Ile Asn Val Thr Glu Val
                165                 170                 175

Asn Pro Leu Gly Ala Ser Thr Arg Leu Leu Asp Val Ser Leu Gln Ser
            180                 185                 190

Ile Leu Arg Pro Asp Pro Pro Gln Gly Leu Arg Val Glu Ser Val Pro
        195                 200                 205

Gly Tyr Pro Arg Arg Leu Arg Ala Ser Trp Thr Tyr Pro Ala Ser Trp
    210                 215                 220

Pro Cys Gln Pro His Phe Leu Leu Lys Phe Arg Leu Gln Tyr Arg Pro
225                 230                 235                 240

Ala Gln His Pro Ala Trp Ser Thr Val Glu Pro Ala Gly Leu Glu Glu
                245                 250                 255

Val Ile Thr Asp Ala Val Ala Gly Leu Pro His Ala Val Arg Val Ser
            260                 265                 270

Ala Arg Asp Phe Leu Asp Ala Gly Thr Trp Ser Thr Trp Ser Pro Glu
```

Ala Trp Gly Thr Pro Ser Thr Gly His His His His His His His
   290                 295                 300

<210> SEQ ID NO 98
<211> LENGTH: 304
<212> TYPE: PRT
<213> ORGANISM: artificial
<220> FEATURE:
<223> OTHER INFORMATION: amino acid sequence of SEQ ID NO: 85 comprising
      a serine at a position corresponding to position 101 of SEQ ID NO:
      1

<400> SEQUENCE: 98

Ser Ser Pro Cys Pro Gln Ala Trp Gly Pro Gly Val Gln Tyr Gly
1               5                   10                  15

Gln Pro Gly Arg Ser Val Lys Leu Cys Cys Pro Gly Val Thr Ala Gly
            20                  25                  30

Asp Pro Val Ser Trp Phe Arg Asp Gly Glu Pro Lys Leu Leu Gln Gly
        35                  40                  45

Pro Asp Ser Gly Leu Gly His Glu Leu Val Leu Ala Gln Ala Asp Ser
    50                  55                  60

Thr Asp Glu Gly Thr Tyr Ile Cys Gln Thr Leu Asp Gly Ala Ser Gly
65                  70                  75                  80

Gly Thr Val Thr Leu Gln Leu Gly Tyr Pro Pro Ala Arg Pro Val Val
                85                  90                  95

Ser Cys Gln Ala Ala Asp Tyr Glu Asn Phe Ser Cys Thr Trp Ser Pro
            100                 105                 110

Ser Gln Ile Ser Gly Leu Pro Thr Arg Tyr Leu Thr Ser Tyr Arg Lys
        115                 120                 125

Lys Thr Val Leu Gly Ala Asp Ser Gln Arg Arg Ser Pro Ser Thr Gly
    130                 135                 140

Pro Trp Pro Cys Pro Gln Asp Pro Leu Gly Ala Ala Arg Cys Val Val
145                 150                 155                 160

His Gly Ala Glu Phe Trp Ser Gln Tyr Arg Ile Asn Val Thr Glu Val
                165                 170                 175

Asn Pro Leu Gly Ala Ser Thr Arg Leu Leu Asp Val Ser Leu Gln Ser
            180                 185                 190

Ile Leu Arg Pro Asp Pro Pro Gln Gly Leu Arg Val Glu Ser Val Pro
        195                 200                 205

Gly Tyr Pro Arg Arg Leu Arg Ala Ser Trp Thr Tyr Pro Ala Ser Trp
    210                 215                 220

Pro Cys Gln Pro His Phe Leu Leu Lys Phe Arg Leu Gln Tyr Arg Pro
225                 230                 235                 240

Ala Gln His Pro Ala Trp Ser Thr Val Glu Pro Ala Gly Leu Glu Glu
                245                 250                 255

Val Ile Thr Asp Ala Val Ala Gly Leu Pro His Ala Val Arg Val Ser
            260                 265                 270

Ala Arg Asp Phe Leu Asp Ala Gly Thr Trp Ser Thr Trp Ser Pro Glu
        275                 280                 285

Ala Trp Gly Thr Pro Ser Thr Gly His His His His His His His
    290                 295                 300

<210> SEQ ID NO 99
<211> LENGTH: 304
<212> TYPE: PRT
<213> ORGANISM: artificial

```
<220> FEATURE:
<223> OTHER INFORMATION: amino acid sequence of SEQ ID NO: 85 comprising
      an serine at a position corresponding to position 178 of SEQ ID
      NO: 1

<400> SEQUENCE: 99

Ser Ser Pro Cys Pro Gln Ala Trp Gly Pro Gly Val Gln Tyr Gly
1               5                   10                  15

Gln Pro Gly Arg Ser Val Lys Leu Cys Cys Pro Gly Val Thr Ala Gly
            20                  25                  30

Asp Pro Val Ser Trp Phe Arg Asp Gly Glu Pro Lys Leu Leu Gln Gly
                35                  40                  45

Pro Asp Ser Gly Leu Gly His Glu Leu Val Leu Ala Gln Ala Asp Ser
        50                  55                  60

Thr Asp Glu Gly Thr Tyr Ile Cys Gln Thr Leu Asp Gly Ala Leu Gly
65                  70                  75                  80

Gly Thr Val Thr Leu Gln Leu Gly Tyr Pro Pro Ala Arg Pro Val Val
                85                  90                  95

Ser Cys Gln Ala Ala Asp Tyr Glu Asn Phe Ser Cys Thr Trp Ser Pro
                100                 105                 110

Ser Gln Ile Ser Gly Leu Pro Thr Arg Tyr Leu Thr Ser Tyr Arg Lys
            115                 120                 125

Lys Thr Val Leu Gly Ala Asp Ser Gln Arg Arg Ser Pro Ser Thr Gly
130                 135                 140

Pro Trp Pro Cys Pro Gln Asp Pro Leu Gly Ala Ser Arg Cys Val Val
145                 150                 155                 160

His Gly Ala Glu Phe Trp Ser Gln Tyr Arg Ile Asn Val Thr Glu Val
                165                 170                 175

Asn Pro Leu Gly Ala Ser Thr Arg Leu Leu Asp Val Ser Leu Gln Ser
            180                 185                 190

Ile Leu Arg Pro Asp Pro Gln Gly Leu Arg Val Glu Ser Val Pro
            195                 200                 205

Gly Tyr Pro Arg Arg Leu Arg Ala Ser Trp Thr Tyr Pro Ala Ser Trp
            210                 215                 220

Pro Cys Gln Pro His Phe Leu Leu Lys Phe Arg Leu Gln Tyr Arg Pro
225                 230                 235                 240

Ala Gln His Pro Ala Trp Ser Thr Val Glu Pro Ala Gly Leu Glu Glu
                245                 250                 255

Val Ile Thr Asp Ala Val Ala Gly Leu Pro His Ala Val Arg Val Ser
                260                 265                 270

Ala Arg Asp Phe Leu Asp Ala Gly Thr Trp Ser Thr Trp Ser Pro Glu
            275                 280                 285

Ala Trp Gly Thr Pro Ser Thr Gly His His His His His His
            290                 295                 300

<210> SEQ ID NO 100
<211> LENGTH: 400
<212> TYPE: PRT
<213> ORGANISM: Homo sapiens

<400> SEQUENCE: 100

Ser Ser Pro Cys Pro Gln Ala Trp Gly Pro Gly Val Gln Tyr Gly
1               5                   10                  15

Gln Pro Gly Arg Ser Val Lys Leu Cys Cys Pro Gly Val Thr Ala Gly
            20                  25                  30

Asp Pro Val Ser Trp Phe Arg Asp Gly Glu Pro Lys Leu Leu Gln Gly
```

```
            35                  40                  45
Pro Asp Ser Gly Leu Gly His Glu Leu Val Leu Ala Gln Ala Asp Ser
 50                  55                  60

Thr Asp Glu Gly Thr Tyr Ile Cys Gln Thr Leu Asp Gly Ala Leu Gly
 65                  70                  75                  80

Gly Thr Val Thr Leu Gln Leu Gly Tyr Pro Pro Ala Arg Pro Val Val
                 85                  90                  95

Ser Cys Gln Ala Ala Asp Tyr Glu Asn Phe Ser Cys Thr Trp Ser Pro
                100                 105                 110

Ser Gln Ile Ser Gly Leu Pro Thr Arg Tyr Leu Thr Ser Tyr Arg Lys
            115                 120                 125

Lys Thr Val Leu Gly Ala Asp Ser Gln Arg Arg Ser Pro Ser Thr Gly
130                 135                 140

Pro Trp Pro Cys Pro Gln Asp Pro Leu Gly Ala Ala Arg Cys Val Val
145                 150                 155                 160

His Gly Ala Glu Phe Trp Ser Gln Tyr Arg Ile Asn Val Thr Glu Val
                165                 170                 175

Asn Pro Leu Gly Ala Ser Thr Arg Leu Leu Asp Val Ser Leu Gln Ser
            180                 185                 190

Ile Leu Arg Pro Asp Pro Pro Gln Gly Leu Arg Val Glu Ser Val Pro
            195                 200                 205

Gly Tyr Pro Arg Arg Leu Arg Ala Ser Trp Thr Tyr Pro Ala Ser Trp
210                 215                 220

Pro Cys Gln Pro His Phe Leu Leu Lys Phe Arg Leu Gln Tyr Arg Pro
225                 230                 235                 240

Ala Gln His Pro Ala Trp Ser Thr Val Glu Pro Ala Gly Leu Glu Glu
                245                 250                 255

Val Ile Thr Asp Ala Val Ala Gly Leu Pro His Ala Val Arg Val Ser
            260                 265                 270

Ala Arg Asp Phe Leu Asp Ala Gly Thr Trp Ser Thr Trp Ser Pro Glu
            275                 280                 285

Ala Trp Gly Thr Pro Ser Thr Gly Thr Ile Pro Lys Glu Ile Pro Ala
290                 295                 300

Trp Gly Gln Leu His Thr Gln Pro Glu Val Glu Pro Gln Val Asp Ser
305                 310                 315                 320

Pro Ala Pro Pro Arg Pro Ser Leu Gln Pro His Pro Arg Leu Leu Asp
                325                 330                 335

His Arg Asp Ser Val Glu Gln Val Ala Val Leu Ala Ser Leu Gly Ile
            340                 345                 350

Leu Ser Phe Leu Gly Leu Val Ala Gly Ala Leu Ala Leu Gly Leu Trp
            355                 360                 365

Leu Arg Leu Arg Arg Gly Gly Lys Asp Gly Ser Pro Lys Pro Gly Phe
370                 375                 380

Leu Ala Ser Val Ile Pro Val Asp Arg Arg Pro Gly Ala Pro Asn Leu
385                 390                 395                 400

<210> SEQ ID NO 101
<211> LENGTH: 410
<212> TYPE: PRT
<213> ORGANISM: Macaca fascicularis

<400> SEQUENCE: 101

Ser Ser Pro Cys Pro Gln Ala Trp Gly Pro Gly Val Gln Tyr Gly
 1               5                  10                  15
```

Gln Pro Gly Arg Pro Val Met Leu Cys Cys Pro Gly Val Ser Ala Gly
                20                  25                  30

Thr Pro Val Ser Trp Phe Arg Asp Gly Asp Ser Arg Leu Leu Gln Gly
            35                  40                  45

Pro Asp Ser Gly Leu Gly His Arg Leu Val Leu Ala Gln Val Asp Ser
        50                  55                  60

Pro Asp Glu Gly Thr Tyr Val Cys Gln Thr Leu Asp Gly Val Ser Gly
65                  70                  75                  80

Gly Met Val Thr Leu Lys Leu Gly Phe Pro Pro Ala Arg Pro Glu Val
                85                  90                  95

Ser Cys Gln Ala Val Asp Tyr Glu Asn Phe Ser Cys Thr Trp Ser Pro
            100                 105                 110

Gly Gln Val Ser Gly Leu Pro Thr Arg Tyr Leu Thr Ser Tyr Arg Lys
        115                 120                 125

Lys Thr Leu Pro Gly Ala Glu Ser Gln Arg Glu Ser Pro Ser Thr Gly
130                 135                 140

Pro Trp Pro Cys Pro Gln Asp Pro Leu Glu Ala Ser Arg Cys Val Val
145                 150                 155                 160

His Gly Ala Glu Phe Trp Ser Glu Tyr Arg Ile Asn Val Thr Glu Val
                165                 170                 175

Asn Pro Leu Gly Ala Ser Thr Cys Leu Leu Asp Val Arg Leu Gln Ser
            180                 185                 190

Ile Leu Arg Pro Asp Pro Pro Gln Gly Leu Arg Val Glu Ser Val Pro
        195                 200                 205

Gly Tyr Pro Arg Arg Leu His Ala Ser Trp Thr Tyr Pro Ala Ser Trp
210                 215                 220

Arg Arg Gln Pro His Phe Leu Leu Lys Phe Arg Leu Gln Tyr Arg Pro
225                 230                 235                 240

Ala Gln His Pro Ala Trp Ser Thr Val Glu Pro Ile Gly Leu Glu Glu
                245                 250                 255

Val Ile Thr Asp Thr Val Ala Gly Leu Pro His Ala Val Arg Val Ser
            260                 265                 270

Ala Arg Asp Phe Leu Asp Ala Gly Thr Trp Ser Ala Trp Ser Pro Glu
        275                 280                 285

Ala Trp Gly Thr Pro Ser Thr Gly Leu Leu Gln Asp Glu Ile Pro Asp
290                 295                 300

Trp Ser Gln Gly His Gly Gln Gln Leu Glu Ala Val Val Ala Gln Glu
305                 310                 315                 320

Asp Ser Leu Ala Pro Ala Arg Pro Ser Leu Gln Pro Asp Pro Arg Pro
                325                 330                 335

Leu Asp His Arg Asp Pro Leu Glu Gln Val Ala Val Leu Ala Ser Leu
            340                 345                 350

Gly Ile Phe Ser Cys Leu Gly Leu Ala Val Gly Ala Leu Ala Leu Gly
        355                 360                 365

Leu Trp Leu Arg Leu Arg Arg Ser Gly Lys Glu Gly Pro Gln Lys Pro
370                 375                 380

Gly Leu Leu Ala Pro Met Ile Pro Val Glu Lys Leu Pro Gly Ile Pro
385                 390                 395                 400

Asn Leu Gln Arg Thr Pro Glu Asn Phe Ser
                405                 410

<210> SEQ ID NO 102
<211> LENGTH: 401
<212> TYPE: PRT

<213> ORGANISM: Mus musculus

<400> SEQUENCE: 102

Ser Pro Cys Pro Gln Ala Trp Gly Pro Pro Val Gln Tyr Gly Gln
1               5                   10                  15

Pro Gly Arg Pro Val Met Leu Cys Cys Pro Gly Val Ser Ala Gly Thr
            20                  25                  30

Pro Val Ser Trp Phe Arg Asp Gly Asp Ser Arg Leu Leu Gln Gly Pro
        35                  40                  45

Asp Ser Gly Leu Gly His Arg Leu Val Leu Ala Gln Val Asp Ser Pro
    50                  55                  60

Asp Glu Gly Thr Tyr Val Cys Gln Thr Leu Asp Gly Val Ser Gly Gly
65                  70                  75                  80

Met Val Thr Leu Lys Leu Gly Phe Pro Pro Ala Arg Pro Glu Val Ser
                85                  90                  95

Cys Gln Ala Val Asp Tyr Glu Asn Phe Ser Cys Thr Trp Ser Pro Gly
                100                 105                 110

Gln Val Ser Gly Leu Pro Thr Arg Tyr Leu Thr Ser Tyr Arg Lys Lys
            115                 120                 125

Thr Leu Pro Gly Ala Glu Ser Gln Arg Glu Ser Pro Ser Thr Gly Pro
    130                 135                 140

Trp Pro Cys Pro Gln Asp Pro Leu Glu Ala Ser Arg Cys Val Val His
145                 150                 155                 160

Gly Ala Glu Phe Trp Ser Glu Tyr Arg Ile Asn Val Thr Glu Val Asn
                165                 170                 175

Pro Leu Gly Ala Ser Thr Cys Leu Leu Asp Val Arg Leu Gln Ser Ile
            180                 185                 190

Leu Arg Pro Asp Pro Pro Gln Gly Leu Arg Val Glu Ser Val Pro Gly
    195                 200                 205

Tyr Pro Arg Arg Leu His Ala Ser Trp Thr Tyr Pro Ala Ser Trp Arg
    210                 215                 220

Arg Gln Pro His Phe Leu Leu Lys Phe Arg Leu Gln Tyr Arg Pro Ala
225                 230                 235                 240

Gln His Pro Ala Trp Ser Thr Val Glu Pro Ile Gly Leu Glu Glu Val
                245                 250                 255

Ile Thr Asp Thr Val Ala Gly Leu Pro His Ala Val Arg Val Ser Ala
            260                 265                 270

Arg Asp Phe Leu Asp Ala Gly Thr Trp Ser Ala Trp Ser Pro Glu Ala
    275                 280                 285

Trp Gly Thr Pro Ser Thr Gly Leu Leu Gln Asp Glu Ile Pro Asp Trp
290                 295                 300

Ser Gln Gly His Gly Gln Gln Leu Glu Ala Val Val Ala Gln Glu Asp
305                 310                 315                 320

Ser Leu Ala Pro Ala Arg Pro Ser Leu Gln Pro Asp Pro Arg Pro Leu
                325                 330                 335

Asp His Arg Asp Pro Leu Glu Gln Val Ala Val Leu Ala Ser Leu Gly
            340                 345                 350

Ile Phe Ser Cys Leu Gly Leu Ala Val Gly Ala Leu Ala Leu Gly Leu
    355                 360                 365

Trp Leu Arg Leu Arg Arg Ser Gly Lys Glu Gly Pro Gln Lys Pro Gly
370                 375                 380

Leu Leu Ala Pro Met Ile Pro Val Glu Lys Leu Pro Gly Ile Pro Asn
385                 390                 395                 400

Leu

```
<210> SEQ ID NO 103
<211> LENGTH: 6
<212> TYPE: PRT
<213> ORGANISM: Artificial Sequence
<220> FEATURE:
<223> OTHER INFORMATION: 8E2 L1 consensus sequence
<220> FEATURE:
<221> NAME/KEY: VARIANT
<222> LOCATION: (3)..(3)
<223> OTHER INFORMATION: X=Y or I or K or M or Q or G or H

<400> SEQUENCE: 103

Val Ser Xaa Tyr Val Glu
1               5

<210> SEQ ID NO 104
<211> LENGTH: 6
<212> TYPE: PRT
<213> ORGANISM: Artificial Sequence
<220> FEATURE:
<223> OTHER INFORMATION: 8E2 L3.1 consensus sequence
<220> FEATURE:
<221> NAME/KEY: VARIANT
<222> LOCATION: (3)..(3)
<223> OTHER INFORMATION: X=A or H or F or N or S or W

<400> SEQUENCE: 104

Gln Gln Xaa Glu Ser Gln
1               5

<210> SEQ ID NO 105
<211> LENGTH: 6
<212> TYPE: PRT
<213> ORGANISM: Artificial Sequence
<220> FEATURE:
<223> OTHER INFORMATION: 8E2 L3.2
<220> FEATURE:
<221> NAME/KEY: VARIANT
<222> LOCATION: (4)..(4)
<223> OTHER INFORMATION: X=A ow W or T or M or Q or W

<400> SEQUENCE: 105

Glu Thr Gln Xaa Pro Phe
1               5

<210> SEQ ID NO 106
<211> LENGTH: 6
<212> TYPE: PRT
<213> ORGANISM: Artificial Sequence
<220> FEATURE:
<223> OTHER INFORMATION: 8E2 H1 consensus sequence

<400> SEQUENCE: 106

Trp Trp Trp Ser Ile Thr
1               5

<210> SEQ ID NO 107
<211> LENGTH: 6
<212> TYPE: PRT
<213> ORGANISM: Artificial Sequence
<220> FEATURE:
<223> OTHER INFORMATION: 8E2 H2 consensus sequence

<400> SEQUENCE: 107

Val Pro Trp Gly Asp Leu
1               5
```

```
<210> SEQ ID NO 108
<211> LENGTH: 6
<212> TYPE: PRT
<213> ORGANISM: Artificial Sequence
<220> FEATURE:
<223> OTHER INFORMATION: 8E2 H3.1 consesnsus sequence
<220> FEATURE:
<221> NAME/KEY: VARIANT
<222> LOCATION: (6)..(6)
<223> OTHER INFORMATION: X=M or R or L

<400> SEQUENCE: 108

Pro Glu Asp Trp Gly Xaa
1               5

<210> SEQ ID NO 109
<211> LENGTH: 6
<212> TYPE: PRT
<213> ORGANISM: Artificial Sequence
<220> FEATURE:
<223> OTHER INFORMATION: 8E2 H3.2 consensus sequence

<400> SEQUENCE: 109

Trp Gly Ser Phe Trp Tyr
1               5
```

IL-11R BINDING PROTEINS

RELATED APPLICATION DATA

The present application claims priority from Australian Patent Application No. 2013900389 entitled "IL-11R binding proteins and uses thereof" filed on 7 Feb. 2013 and from U.S. Patent Application No. 61/764,756 entitled "IL-11R binding proteins and uses thereof" filed on 14 Feb. 2013. The entire contents of those applications are hereby incorporated by reference.

SEQUENCE LISTING

The Sequence Listing in the ASCII text file, named as P29799_SequenceListingProvisional.txt of 164 KB, created on Feb. 14, 2013, and submitted to the United States Patent and Trademark Office via EFS-Web, is incorporated herein by reference.

FIELD

The present disclosure relates to proteins comprising antigen binding sites of antibodies that bind to interleukin-11 (IL-11) receptor alpha (IL-11Rα) and uses thereof, e.g., in therapy.

BACKGROUND

IL-11 is a member of the IL-6 cytokine family which also comprises IL-27, IL-31, leukemia inhibitory factor (LIF), oncostatin M (OSM) and ciliary neurotrophic factor (CNTF) amongst others. IL-6 family cytokines induce signal transduction via a common signal-transducing receptor β-subunit, gp130 and a specific receptor α-subunit. In the case of IL-11, binding of this cytokine to its specific receptor α-subunit, IL-11Rα, induces gp130 homodimerization. Dimerization of gp130 activates the JAK/STAT signaling pathway and leads to the activation of signal transducer and activator of transcription (STAT) 3 (STAT3) and to a lesser extent, STAT1.

IL-11 signaling is known to play a role in hematopoiesis, immune response, inflammation, adipogenesis, osteoclastogenesis, neurogenesis, megakaryocyte maturation and platelet production. IL-11 is used clinically or is in development for treating a variety of conditions, e.g., chemotherapy-induced thrombocytopenia, and various inflammatory disorders including arthritis, inflammatory bowel disease, radiation-induced lung damage, sepsis and psoriasis. However, clinical use of IL-11 has been restricted due to reports of serious adverse events including edema. Moreover, IL-11 has been shown to have deleterious effects in various conditions.

For example, IL-11 has been found to act as an inhibitor of bone formation, and is critical for osteoclast formation and activity and bone resorption. Thus, blocking the activity of IL-11 has been proposed as a treatment for osteoporosis and for preventing bone resorption/promoting bone formation in other conditions such as metastatic bone cancer, myeloma, Paget's disease of bone, and bone fracture and healing.

IL-11 signaling has been implicated as having a pathogenic role during the early phase of tuberculosis. Blocking IL-11 with an anti-IL-11 antibody was shown to diminish histopathology and neutrophilic infiltration of the lung tissue in mice infected with *Mycobacterium tuberculosis*.

Antagonism of IL-11 has also been proposed as a method of treating Th2-mediated disorders including asthma, chronic obstructive pulmonary disease (COPD), rhinitis, allergies and atopic dermatitis. In this regard, blocking IL-11 signaling using a mutant form of IL-11 that does not induce signal transduction was shown to be of therapeutic benefit in a mouse model of asthma.

IL-11 and/or IL-11Rα is overexpressed in liver cancer, pancreatic cancer, gastric cancer, osteosarcoma, endometrial cancer and ovarian cancer. Moreover, as discussed above, IL-11 induced gp130 dimerization leads to activation of STAT3, which induces expression of genes associated with angiogenesis (e.g. VEGF), cell cycle progression (e.g. cylin D1) and cell survival (e.g. Bcl-XL, survival). Persistent STAT3 activity appears to be associated with hematologic malignancies and tumors of epithelial origin. Excessive STAT3 activation promotes the growth and survival of gastric cells, is associated with increased gastric angiogenesis and leads to gastric tumorigenesis in mice. However, gastric inflammation, hyperplasia and tumor formation are suppressed in IL-11 unresponsive mice or in mice treated with a non-signaling mutant of IL-11.

IL-11 is also involved in other biological processes, such as, inhibition of adipogenesis, induction of cachexia (e.g., cancer cachexia), induction of a febrile response, modulation of extracellular matrix metabolism, stimulation of acute-phase reactants and embryo implantation.

It will be apparent to the skilled artisan from the foregoing that reagents that neutralize IL-11 signaling are desirable for their potential to provide a therapeutic benefit in any of a number of diverse conditions. Reagents that bind to the IL-11Rα are also desirable since they have the advantage of being capable of specifically targeting cells in vivo as opposed to needing to bind to and neutralize soluble IL-11 throughout a subject.

Despite this desirability, many reagents (e.g., antibodies) that bind to IL-11Rα do not neutralize IL-11 signaling. For example, Blanc et al (*Journal of Immunological Methods* 241: 43-59, 2000) described a panel of 14 mouse monoclonal antibodies raised against human IL-11Rα but none of them were capable of inhibiting IL-11-induced proliferation of BaF3/gp130/IL-11R cells, indicating that the antibodies do not neutralize IL-11 signaling. Commercially available anti-IL-11Rα antibodies, e.g., 4D12 available from Santa Cruz Biotechnology, Inc., also do not neutralize IL-11 signaling.

SUMMARY

In producing the present invention, the inventors sought to produce reagents (e.g., antibodies and proteins comprising antigen binding domains thereof) that bind to IL-11Rα and neutralize IL-11 signaling. The inventors produced a series of antibodies having such activity, some of which potently neutralize IL-11 signaling, e.g., prevent proliferation of IL-11-dependent BaF3 cell proliferation. These antibodies were shown to be cross-reactive with human IL-11Rα (hIL-11Rα) and cynomolgus monkey IL-11Rα (cynoIL-11Rα), meaning that they may be used in primate models of human disease. The antibodies were also found to bind to overlapping epitopes. The inventors then affinity matured one of these antibodies and produced a series of additional antibodies having additional desirable properties, e.g., neutralization of IL-11 signaling and/or improved affinity and/or sequences similar to human germline (e.g., having a reduced likelihood of inducing an immune response when administered to a human).

Based on the foregoing, it will be apparent to the skilled artisan that the inventors have produced a protein comprising an antigen binding domain of an antibody, the antigen binding domain capable of binding to or specifically binding to IL-11Rα and neutralizing IL-11 signaling.

In one example, the present disclosure provides an IL-11Rα-binding protein comprising an antigen binding domain of an antibody, the antigen binding domain binds to or specifically binds to IL-11Rα and neutralizes IL-11 signaling, wherein the antigen binding domain is capable of binding to hIL-11Rα and cynoIL-11Rα.

In one example, the IL-11Rα-binding protein neutralizes human IL-11 (hIL-11) and/or cynomolgus monkey IL-11 (cynoIL-11) signaling.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and the protein inhibits IL-11 (e.g., hIL-11 or cynoIL-11)-mediated proliferation of BaF3 cells expressing IL-11Rα and gp130 with an $IC_{50}$ of 10 µg/ml or less. In one example, the $IC_{50}$ is 5 µg/ml or less. For example, the $IC_{50}$ is 4 µg/ml or less or 3.5 µg/ml or less. In one example, the $IC_{50}$ is 3 µg/ml or less or 2 µg/ml or less. For example, the $IC_{50}$ is 1 µg/ml or less. For example, the $IC_{50}$ is 0.9 µg/ml or less or 0.8 µg/ml or less or 0.7 µg/ml. In one example, the $IC_{50}$ is 0.7 µg/ml or less. In one example, relating to each of the foregoing examples, the $IC_{50}$ can be 10 pg/ml or more or 10 ng/ml or more.

In one example, the IL-11Rα-binding protein inhibits IL-11 (e.g., hIL-11 or cynoIL-11)-mediated proliferation of BaF3 cells expressing IL-11Rα and gp130 with an $IC_{50}$ at least about 1.5 fold greater than antibody 8E2 (comprising a heavy chain comprising a sequence set forth in SEQ ID NO: 83 and a light chain comprising a sequence set forth in SEQ ID NO: 84). In one example, the $IC_{50}$ is at least about 2 fold greater or at least about 2.5 fold greater or at least about 3 fold greater than antibody 8E2.

In one example, the $IC_{50}$ is determined by culturing BaF3 cells expressing IL-11Rα and gp130 (e.g., genetically modified to express IL-11Rα and/or gp130) (e.g., about $1 \times 10^4$ cells) in the presence of from about 0.5 ng/mL hIL-11 to about 5 ng/mL hIL-11 (e.g., in the presence of about 0.5 ng/mL hIL-11 or about 5 ng/mL hIL-11) for about 48 hours. In one example, proliferation is determined by measuring incorporation of 3H-thymidine into DNA during the last 6 hours of culture. In assays performed to determine neutralization of cynoIL-11, the cells can be cultured in the presence of from about 0.5 ng/mL cynoIL-11 to about 5 ng/mL cynoIL-11 (e.g., in the presence of about 0.5 ng/mL cynoIL-11 or about 5 ng/mL cynoIL-11).

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and the level of binding of the IL-11Rα-binding protein to a polypeptide of SEQ ID NO: 86 is lower than the level of binding of the IL-11Rα-binding to a polypeptide of SEQ ID NO: 3 and/or 85.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and the level of binding of the IL-11Rα-binding protein to a polypeptide of SEQ ID NO: 89 is lower than the level of binding of the IL-11Rα-binding to a polypeptide of SEQ ID NO: 3 and/or 85.

In one example, the level of binding is determined by Western Blotting and/or by fluorescence-activated cell sorting (FACS) of cells expressing the polypeptide.

In one example, the level of binding of the IL-11Rα-binding protein to the polypeptide of SEQ ID NO: 86 or 89 is reduced by at least about 10 fold or 20 fold or 50 fold or 100 fold or 150 fold or 200 fold compared to the binding of the IL-11Rα-binding protein to the polypeptide of SEQ ID NO: 3 and/or 85.

In one example, the IL-11Rα-binding protein does not detectably bind to the polypeptide of SEQ ID NO: 86 or 89.

In one example, the IL-11Rα-binding protein binds to a polypeptide of SEQ ID NO: 87 or 88. For example, the level of binding of the IL-11Rα-binding protein binds to a polypeptide of SEQ ID NO: 87 or 88 is similar to or about the same as (e.g., within about 20% or 15% or 10% or 5%) of the level of binding to the polypeptide of SEQ ID NO: 3 and/or 85.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and the antigen binding domain binds to an epitope comprising residues within the first fibronectin III domain of IL-11Rα.

In one example, the epitope comprises residues within the immunoglobulin-like domain and the first fibronectin III domain of IL-11Rα

In one example, the epitope comprises residues between amino acids 111-215 of SEQ ID NO: 1.

In one example, the epitope comprises residues between amino acids 1-215 of SEQ ID NO: 1.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and wherein the protein competitively inhibits binding of antibody 8E2 (comprising a $V_H$ comprising a sequence set forth in SEQ ID NO: 37 and a $V_L$ comprising a sequence set forth in SEQ ID NO: 5) to hIL-11Rα and/or to a polypeptide of SEQ ID NO: 3 and/or 85.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and wherein the protein competitively inhibits binding of antibody 8E4 (comprising a $V_H$ comprising a sequence set forth in SEQ ID NO: 74 and a $V_L$ comprising a sequence set forth in SEQ ID NO: 73) to hIL-11Rα and/or to a polypeptide of SEQ ID NO: 3 and/or 85.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and wherein the protein competitively inhibits binding of antibody 8D10 (comprising a $V_H$ comprising a sequence set forth in SEQ ID NO: 76 and a $V_L$ comprising a sequence set forth in SEQ ID NO: 75) to hIL-11Rα and/or to a polypeptide of SEQ ID NO: 3 and/or 85.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and wherein the protein competitively inhibits binding of antibody 8E2 (comprising a heavy chain comprising a $V_H$ comprising a sequence set forth in SEQ ID NO: 37 and a human IgG4 constant region and a light chain comprising a $V_L$ comprising a sequence set forth in SEQ ID NO: 5 and a human light chain constant region) to hIL-11Rα and/or to a polypeptide of SEQ ID NO: 3 and/or 85.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and wherein the protein competitively inhibits binding of antibody 8E4 (comprising a heavy chain comprising a $V_H$ comprising a sequence set forth in SEQ ID NO: 74 and a human IgG4 constant region and a light chain comprising a $V_L$ comprising a sequence set forth in SEQ ID NO: 73 and a human light chain constant region) to hIL-11Rα and/or to a polypeptide of SEQ ID NO: 3 and/or 85.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and wherein the protein competitively inhibits binding of antibody 8D10 (comprising a heavy chain comprising a $V_H$ comprising a sequence set forth in SEQ ID NO: 76 and a human IgG4 constant region and a light chain comprising a $V_L$ comprising a sequence set forth in SEQ ID NO: 75 and a human light chain constant region) to hIL-11Rα and/or to a polypeptide of SEQ ID NO: 3 and/or 85.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and wherein the protein competitively inhibits binding of antibody 8E2 (comprising a heavy chain comprising a sequence set forth in SEQ ID NO: 83 and a light chain comprising a sequence set forth in SEQ ID NO: 84) to hIL-11Rα and/or to a polypeptide of SEQ ID NO: 3 and/or 85.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and wherein the protein competitively inhibits binding of antibody 8E4 (comprising a heavy chain comprising a sequence set forth in SEQ ID NO: 92 and a light chain comprising a sequence set forth in SEQ ID NO: 91) to hIL-11Rα and/or to a polypeptide of SEQ ID NO: 3 and/or 85.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and wherein the protein competitively inhibits binding of antibody 8D10 ((comprising a heavy chain comprising a sequence set forth in SEQ ID NO: 94 and a light chain comprising a sequence set forth in SEQ ID NO: 93) to hIL-11Rα and/or to a polypeptide of SEQ ID NO: 3 and/or 85.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and wherein the level of binding of the IL-11Rα-binding protein to a polypeptide of SEQ ID NO: 95 is lower than the level of binding of the IL-11Rα-binding protein to a polypeptide of SEQ ID NO: 85.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and wherein the level of binding of the IL-11Rα-binding protein to a polypeptide of SEQ ID NO: 96 is lower than the level of binding of the IL-11Rα-binding protein to a polypeptide of SEQ ID NO: 85.

In one example, the level of binding of the IL-11Rα-binding protein to the polypeptide comprising the substitution is reduced by at least about 1.5 fold or 2 fold.

In one example, the level of binding of the IL-11Rα-binding protein to the polypeptide comprising the substitution is reduced by at least about 3 fold or 4 fold or 5 fold or 10 fold.

In one example, the IL-11Rα-binding protein does not detectably bind to the polypeptide comprising the substitution.

In one example, the level of binding is assessed using a biosensor, e.g., by surface plasmon resonance. For example, the IL-11Rα-binding protein is immobilized and the level of binding to a polypeptide of SEQ ID NO: 85, 95 or 96 is determined. As exemplified herein, by assessing the level of binding at several concentrations an affinity can be determined.

In another example, the level of binding is assessed using FACS. For example, binding of the IL-11Rα-binding protein to a cell expressing a polypeptide of SEQ ID NO: 85, 95 or 96 or to a form of the IL-11Rα comprising a substitution described herein.

In one example, the IL-11Rα-binding protein preferentially binds to a polypeptide of SEQ ID NO: 85 relative to its ability to bind to a polypeptide of SEQ ID NO: 95 or 96.

In one example, the IL-11Rα-binding protein competitively inhibits binding of antibody 8E2 (comprising a $V_H$ comprising a sequence set forth in SEQ ID NO: 37 and a $V_L$ comprising a sequence set forth in SEQ ID NO: 5) and/or 8E4 (comprising a $V_H$ comprising a sequence set forth in SEQ ID NO: 74 and a $V_L$ comprising a sequence set forth in SEQ ID NO: 73) and/or 8D10 (comprising a $V_H$ comprising a sequence set forth in SEQ ID NO: 76 and a $V_L$ comprising a sequence set forth in SEQ ID NO: 75) to a polypeptide of SEQ ID NO: 3 and/or 85.

In one example, the antigen binding domain cross-reacts with:
(i) a polypeptide of SEQ ID NO: 97; and/or
(ii) a polypeptide of SEQ ID NO: 98; and/or
(iii) a polypeptide of SEQ ID NO: 99.

In one example, the IL-11Rα-binding protein does not detectably bind to mouse IL-11Rα (SEQ ID NO: 82 or 102) and/or to a polypeptide of SEQ ID NO: 90.

In one example, the IL-11Rα-binding protein cross-reacts with mouse IL-11Rα (SEQ ID NO: 82 or 102) and/or to a polypeptide of SEQ ID NO: 90.

In one example, the IL-11Rα-binding protein has an affinity constant ($K_D$) for human IL-11Rα and/or the polypeptide of SEQ ID NO: 3 and/or 85 of about $9 \times 10^{-9}$M or less. For example, the $K_D$ is about $8 \times 10^{-9}$M or less or about $7 \times 10^{-9}$M or less or about $6 \times 10^{-9}$M or less or about $5 \times 10^{-9}$M or less. In one example, the $K_D$ is about $4.8 \times 10^{-9}$M or less.

In another example, the IL-11Rα-binding protein has an affinity constant ($K_D$) for human IL-11Rα and/or the polypeptide of SEQ ID NO: 3 and/or 85 of about $2 \times 10^{-9}$M or less. For example, the $K_D$ is about $1 \times 10^{-9}$M or less or about $9 \times 10^{-10}$M or less or about $8 \times 10^{-10}$M or less or about $7 \times 10^{-10}$M or less. In one example, the $K_D$ is about $5 \times 10^{-10}$M or less. In one example, the $K_D$ is about $4 \times 10^{-10}$M or less. In one example, the $K_D$ is about $3 \times 10^{-10}$M or less. In one example, the $K_D$ is about $2 \times 10^{-10}$M or less. In one example, the $K_D$ is about $1.5 \times 10^{-10}$M or less.

In one example, relating to each of the foregoing examples, the $K_D$ can be $0.1 \times 10^{-12}$M or more or $1 \times 10^{-12}$M or more.

In one example, the $K_D$ is assessed using a biosensor, e.g., by surface plasmon resonance. For example, the IL-11Rα-binding protein is immobilized and the level of binding to a polypeptide of SEQ ID NO: 85 is determined.

In one example, the IL-11Rα-binding protein has a thermal transition midpoint (Tm) of about 60° C. or greater. For example, the Tm is about 61° C. or greater, for example, about 62° C. or greater, such as, about 63° C. or greater. For example, the Tm is about 65° C. or greater. For example, the Tm is about 69° C. or greater. For example, the Tm is about 70° C. or greater. Proteins having higher Tms are considered to be more stable, thereby providing for better storage and/or reduced effects upon administration, e.g., due to aggregation.

The present disclosure additionally or alternatively provides an IL-11Rα-binding protein comprising an antigen binding domain of an antibody, wherein the antigen binding domain binds to or specifically binds to IL-11Rα and neutralizes IL-11 signaling and wherein the antigen binding domain comprises at least one of:

(i) a $V_H$ comprising a complementarity determining region (CDR) 1 comprising a sequence at least about 40% identical (or 50% identical or 60% identical or 70% identical or 80% identical or 90% identical or 95% identical or 98% identical or 99% identical or 100% identical) to a sequence set forth between amino acids 31-35 of SEQ ID NO: 37, a CDR2 comprising a sequence at least about 76% identical (or 80% identical or 90% identical or 95% identical or 98% identical or 99% identical or 100% identical) to a sequence set forth between amino acids 50-66 of SEQ ID NO: 37 and a CDR3 comprising a sequence at least about 55% identical (or 60% identical or 70% identical or 80% identical or 90% identical or 95% identical or 98% identical or 99% identical or 100% identical) to a sequence set forth between amino acids 99-107 of SEQ ID NO: 37;

(ii) a $V_H$ comprising a sequence at least about 95% or 96% or 97% or 98% or 99% identical to a sequence set forth in SEQ ID NO: 37;

(iii) a $V_L$ comprising a CDR1 comprising a sequence at least about 45% identical (or 50% identical or 55% identical or 60% identical or 70% identical or 80% identical or 90% identical or 95% identical or 98% identical or 99% identical or 100% identical) to a sequence set forth between amino acids 24-34 of SEQ ID NO: 5, a CDR2 comprising a sequence set forth between amino acids 50-56 of SEQ ID NO: 5 and a CDR3 comprising a sequence at least about 44% identical (or 56% identical or 60% identical or 70% identical or 80% identical or 90% identical or 95% identical or 98% identical or 99% identical or 100% identical) to a sequence set forth between amino acids 89-97 of SEQ ID NO: 5;

(iv) a $V_L$ comprising a sequence at least about 94% identical (or 95% identical or 96% identical or 97% identical or 98% identical or 99% identical) to a sequence set forth in SEQ ID NO: 5;

(v) a $V_H$ comprising a CDR1 comprising a sequence set forth between amino acids 31-35 of SEQ ID NO: 74, a CDR2 comprising a sequence set forth between amino acids 50-66 of SEQ ID NO: 74 and a CDR3 comprising a sequence set forth between amino acids 99-115 of SEQ ID NO: 74;

(vi) a $V_H$ comprising a sequence set forth in SEQ ID NO: 74;

(vii) a $V_L$ comprising a CDR1 comprising a sequence set forth between amino acids 23-36 of SEQ ID NO: 73, a CDR2 comprising a sequence set forth between amino acids 52-58 of SEQ ID NO: 73 and a CDR3 comprising a sequence set forth between amino acids 91-101 of SEQ ID NO: 73;

(viii) a $V_L$ comprising a sequence set forth in SEQ ID NO: 73;

(ix) a $V_H$ comprising a CDR1 comprising a sequence set forth between amino acids 31-35 of SEQ ID NO: 76, a CDR2 comprising a sequence set forth between amino acids 50-66 of SEQ ID NO: 76 and a CDR3 comprising a sequence set forth between amino acids 99-107 of SEQ ID NO: 76;

(x) a $V_H$ comprising a sequence set forth in SEQ ID NO: 76;

(xi) a $V_L$ comprising a CDR1 comprising a sequence set forth between amino acids 24-34 of SEQ ID NO: 75, a CDR2 comprising a sequence set forth between amino acids 50-57 of SEQ ID NO: 75 and a CDR3 comprising a sequence set forth between amino acids 89-97 of SEQ ID NO: 75;

(xii) a $V_L$ comprising a sequence set forth in SEQ ID NO: 75;
(xiii) a $V_H$ as set forth in (i) and a $V_L$ as set forth in (iii);
(xiv) a $V_H$ as set forth in (i) and a $V_L$ as set forth in (iv);
(xv) a $V_H$ as set forth in (ii) and a $V_L$ as set forth in (iii);
(xvi) a $V_H$ as set forth in (ii) and a $V_L$ as set forth in (iv);
(xvii) a $V_H$ as set forth in (v) and a $V_L$ as set forth in (vii);
(xviii) a $V_H$ as set forth in (v) and a $V_L$ as set forth in (viii);
(xix) a $V_H$ as set forth in (vi) and a $V_L$ as set forth in (vii);
(xx) a $V_H$ as set forth in (vi) and a $V_L$ as set forth in (viii);
(xxi) a $V_H$ as set forth in (ix) and a $V_L$ as set forth in (xi);
(xxii) a $V_H$ as set forth in (ix) and a $V_L$ as set forth in (xii);
(xxiii) a $V_H$ as set forth in (x) and a $V_L$ as set forth in (xi); or
(xxiv) a $V_H$ as set forth in (x) and a $V_L$ as set forth in (xii).

In one example, the antigen binding domain comprises:

(i) a $V_H$ comprising a CDR1 comprising a sequence set forth between amino acids 31-35 of SEQ ID NO: 37, a CDR2 comprising a sequence at least about 80% identical (or 90% identical or 95% identical or 98% identical or 99% identical or 100% identical) to a sequence set forth between amino acids 50-66 of SEQ ID NO: 37 and a CDR3 comprising a sequence at least about 55% identical (or 60% identical or 70% identical or 80% identical or 90% identical or 95% identical or 98% identical or 99% identical or 100% identical) to a sequence set forth between amino acids 99-107 of SEQ ID NO: 37 and a $V_L$ comprising a CDR1 comprising a sequence set forth between amino acids 24-34 of SEQ ID NO: 5, a CDR2 comprising a sequence set forth between amino acids 50-56 of SEQ ID NO: 5 and a CDR3 comprising a sequence set forth between amino acids 89-97 of SEQ ID NO: 5 or a $V_L$ comprising a sequence set forth in SEQ ID NO: 5;

(ii) a $V_H$ comprising a CDR1 comprising a sequence set forth between amino acids 31-35 of SEQ ID NO: 37, a CDR2 comprising a sequence at least about 80% identical (or 90% identical or 95% identical or 98% identical or 99% identical or 100% identical) to a sequence set forth between amino acids 50-66 of SEQ ID NO: 37 and a CDR3 comprising a sequence set forth between amino acids 99-107 of SEQ ID NO: 37 and a $V_L$ comprising a CDR1 comprising a sequence set forth between amino acids 24-34 of SEQ ID NO: 5, a CDR2 comprising a sequence set forth between amino acids 50-56 of SEQ ID NO: 5 and a CDR3 comprising a sequence set forth between amino acids 89-97 of SEQ ID NO: 5 or a $V_L$ comprising a sequence set forth in SEQ ID NO: 5; or (iii) a $V_H$ comprising a CDR1 comprising a sequence set forth between amino acids 31-35 of SEQ ID NO: 37, a CDR2 comprising a sequence set forth between amino acids 50-66 of SEQ ID NO: 37 and a CDR3 comprising a sequence at least about 55% identical (or 60% identical or 70% identical or 80% identical or 90% identical or 95% identical or 98% identical or 99% identical or 100% identical) to a sequence set forth between amino acids 99-107 of SEQ ID NO: 37 and a $V_L$ comprising a CDR1 comprising a sequence set forth between amino acids 24-34 of SEQ ID NO: 5, a CDR2 comprising a sequence set forth between amino acids 50-56 of SEQ ID NO: 5 and a CDR3 comprising a sequence set forth between amino acids 89-97 of SEQ ID NO: 5 or a $V_L$ comprising a sequence set forth in SEQ ID NO: 5.

In one example, the antigen binding domain comprises:

(i) a $V_H$ comprising a CDR1 comprising a sequence set forth between amino acids 31-35 of SEQ ID NO: 37, a CDR2 comprising a sequence set forth between amino acids 50-66 of SEQ ID NO: 37 and a CDR3 comprising a sequence set forth between amino acids 99-107 of SEQ ID NO: 37 or a $V_H$ comprising a sequence set forth in SEQ ID NO: 37 and a $V_L$ comprising a CDR1 comprising a sequence at least about 54% identical (or 60% identical or 70% identical or 80% identical or 90% identical or 95% identical or 98% identical or 99% identical or 100% identical) to a sequence set forth between amino acids 24-34 of SEQ ID NO: 5, a CDR2 comprising a sequence set forth between amino acids 50-56 of SEQ ID NO: 5 and a CDR3 comprising a sequence at least about 66% identical (or 70% identical or 80% identical or 90% identical or 95% identical or 98% identical or 99% identical or 100% identical) to a sequence set forth between amino acids 89-97 of SEQ ID NO: 5;

(ii) a $V_H$ comprising a CDR1 comprising a sequence set forth between amino acids 31-35 of SEQ ID NO: 37, a CDR2 comprising a sequence set forth between amino acids 50-66 of SEQ ID NO: 37 and a CDR3 comprising a sequence set forth between amino acids 99-107 of SEQ ID NO: 37 or a $V_H$ comprising a sequence set forth in SEQ ID NO: 37 and a $V_L$ comprising a CDR1 comprising a sequence at least about 54% identical (or 60% identical or 70% identical or 80% identical or 90% identical or 95% identical or 98% identical or 99% identical or 100% identical) to a sequence set forth between amino acids 24-34 of SEQ ID NO: 5, a CDR2 comprising a sequence set forth between amino acids 50-56 of SEQ ID NO: 5 and a CDR3 comprising a sequence set forth between amino acids 89-97 of SEQ ID NO: 5; or (iii) a $V_H$ comprising a CDR1 comprising a sequence set forth between amino acids 31-35 of SEQ ID NO: 37, a CDR2 comprising a sequence set forth between amino acids 50-66 of SEQ ID NO: 37 and a CDR3 comprising a sequence set forth between amino acids 99-107 of SEQ ID NO: 37 or a $V_H$ comprising a sequence set forth in SEQ ID NO: 37 and a $V_L$ comprising a CDR1 comprising a sequence set forth between amino acids 24-34 of SEQ ID NO: 5, a CDR2 comprising a sequence set forth between amino acids 50-56 of SEQ ID NO: 5 and a CDR3 comprising a sequence at least about 66% identical (or 70% identical or 80% identical or 90% identical or 95% identical or 98% identical or 99% identical or 100% identical) to a sequence set forth between amino acids 89-97 of SEQ ID NO: 5.

In one example, the antigen binding domain comprises:

(i) a $V_H$ comprising a sequence set forth in SEQ ID NO: 71 and a $V_L$ comprising a sequence set forth in SEQ ID NO: 35; or (ii) a $V_H$ comprising a sequence set forth in SEQ ID NO: 72 and a $V_L$ comprising a sequence set forth in SEQ ID NO: 36.

Such an IL-11Rα-binding protein can exhibit any one or more of the functional activities described herein, e.g., preferential binding to a polypeptide of SEQ ID NO: 3 relative to the level of binding of a polypeptide of SEQ ID NO: 3 comprising a substitution as described above.

In one example, differences between the recited sequence and the IL-11Rα-binding protein are substitutions.

The skilled artisan will be capable of determining sites for mutations to an IL-11Rα-binding protein of the disclosure, e.g., within a framework region of a variable region containing protein. Moreover, the inventors have identified numerous sites in a $V_H$ CDR1, CDR2 and/or CDR3 and a $V_L$ CDR1 and/or CDR3 that can be mutated as well as numerous mutations that maintain or improve activity of an IL-11Rα-binding protein of the disclosure. For example a mutation, e.g., a substitution is within HCDR1 and/or one or more (e.g., 2 or 3 or 4) of HCDR2 and/or one or more (e.g., 2 or 3 or 4 or 5 or 6) of the six N-terminal or the six C-terminal residues of HCDR3 of antibody 8E2. For example a mutation, e.g., a substitution is within at least one (e.g., 2 or 3 or 4 or 5 or 6) of the six C-terminal amino acids of LCDR1 and/or one or more (e.g., 2 or 3 or 4 or 5) of the five N-terminal of LCDR3 of antibody 8E2.

In one example, an IL-11Rα-binding protein of the disclosure comprises a light chain CDR1 comprising the sequence: QASQDX$_1$X$_2$X$_3$X$_4$X$_5$X$_6$ (SEQ ID NO: 77)
wherein X$_1$=I or V; X$_2$=N or D or G or S or A or H; X$_3$=N or Y or I or K or M or Q or G or H; X$_4$=Y or W; X$_5$=L or V or I or M and X$_6$=N or E.

In one example, an IL-11Rα-binding protein of the disclosure comprises a light chain CDR3 comprising the sequence: X$_1$QX$_2$X$_3$X$_4$X$_5$X$_6$PX$_7$ (SEQ ID NO: 78)
wherein X$_1$=Q or E or S or T; X$_2$=Y or H or F or N or S or W; X$_3$=D or E; X$_4$=N, D, F, S, E o T; X$_5$=L or Q; X$_6$=S or A or W or T or M or Q and X$_7$=T or E or F or A or L or F or N or Q.

In one example, X$_1$ is Q and X$_2$ is Y.
In one example, X$_6$ is S and X$_7$ is T.
In one example, an IL-11Rα-binding protein of the disclosure comprises a heavy chain CDR1 comprising the sequence:
X$_1$X$_2$SX$_3$X$_4$
wherein X$_1$=W or R; X$_2$=Y or W or F; X$_4$=M or I or V or T or L and X$_5$=T or A In one example, an IL-11Rα-binding protein of the disclosure comprises a heavy chain CDR2 comprising the sequence:
SIVPX$_1$X$_2$X$_3$X$_4$TQYADSVKG
wherein X$_1$=S or W or Y or H; X$_2$=G or A; X$_3$=G or D or T and X$_4$=H or Y or L or I or F In one example, an IL-11Rα-binding protein of the disclosure comprises a heavy chain CDR3 comprising the sequence:
X$_1$X$_2$X$_3$WGX$_4$FX$_5$X$_6$
wherein X$_1$=G or P; X$_2$=P or E or V or L or N or H; X$_3$=G or D; X$_4$=S or M or R or L; X$_5$=D or A or W and X$_6$=L or V or F or Q or E or Y or T In one example, X$_1$ is G, X$_2$ is P and X$_3$ is G.
In one example, X$_5$ is D and X$_6$ is L.
In one example, the IL-11Rα-binding protein comprises one of the foregoing consensus sequences as a CDR and the remaining CDRs are from antibody 8E2.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising a sequence set forth in any one of SEQ ID NOs: 37 to 70, 74 or 76 and/or a $V_L$ comprising a sequence set forth in any one of SEQ ID NOs: 5 to 34, 73 or 75.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises:

(i) a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 5;
(ii) a $V_H$ comprising a sequence set forth in SEQ ID NO: 37 and a $V_L$ comprising a sequence set forth in SEQ ID NO: 5;
(iii) a $V_H$ comprising CDRs 1, 2 and 3 of a sequence set forth in SEQ ID NO: 38 (optionally, also comprising the amino acid N-terminal to CDR1) and a $V_L$ comprising CDRs 1, 2 and 3 of a sequence set forth in SEQ ID NO: 5;
(iv) a $V_H$ comprising a sequence set forth in SEQ ID NO: 38 and a $V_L$ comprising a sequence set forth in SEQ ID NO: 5;
(v) a $V_H$ comprising CDRs 1, 2 and 3 of a sequence set forth in SEQ ID NO: 39 (optionally, also comprising the amino acid N-terminal to CDR1) and a $V_L$ comprising CDRs 1, 2 and 3 of a sequence set forth in SEQ ID NO: 5;
(vi) a $V_H$ comprising a sequence set forth in SEQ ID NO: 39 and a $V_L$ comprising a sequence set forth in SEQ ID NO: 5;
(vii) a $V_H$ comprising CDRs 1, 2 and 3 of a sequence set forth in SEQ ID NO: 40 (optionally, also comprising the amino acid N-terminal to CDR1) and a $V_L$ comprising CDRs 1, 2 and 3 of a sequence set forth in SEQ ID NO: 5;
(viii) a $V_H$ comprising a sequence set forth in SEQ ID NO: 40 and a $V_L$ comprising a sequence set forth in SEQ ID NO: 5;
(ix) a $V_H$ comprising CDRs 1, 2 and 3 of a sequence set forth in SEQ ID NO: 41 (optionally, also comprising the amino acid N-terminal to CDR1) and a $V_L$ comprising CDRs 1, 2 and 3 of a sequence set forth in SEQ ID NO: 5;
(x) a $V_H$ comprising a sequence set forth in SEQ ID NO: 41 and a $V_L$ comprising a sequence set forth in SEQ ID NO: 5;
(xi) a $V_H$ comprising CDRs 1, 2 and 3 of a sequence set forth in SEQ ID NO: 42 (optionally, also comprising the amino acid N-terminal to CDR1) and a $V_L$ comprising CDRs 1, 2 and 3 of a sequence set forth in SEQ ID NO: 5;
(xii) a $V_H$ comprising a sequence set forth in SEQ ID NO: 42 and a $V_L$ comprising a sequence set forth in SEQ ID NO: 5;
(xiii) a $V_H$ comprising CDRs 1, 2 and 3 of a sequence set forth in SEQ ID NO: 43 (optionally, also comprising the amino acid N-terminal to CDR1) and a $V_L$ comprising CDRs 1, 2 and 3 of a sequence set forth in SEQ ID NO: 5;
(xiv) a $V_H$ comprising a sequence set forth in SEQ ID NO: 43 and a $V_L$ comprising a sequence set forth in SEQ ID NO: 5;
(xv) a $V_H$ comprising CDRs 1, 2 and 3 of a sequence set forth in SEQ ID NO: 44 (optionally, also comprising the amino acid N-terminal to CDR1) and a $V_L$ comprising CDRs 1, 2 and 3 of a sequence set forth in SEQ ID NO: 5;
(xvi) a $V_H$ comprising a sequence set forth in SEQ ID NO: 44 and a $V_L$ comprising a sequence set forth in SEQ ID NO: 5;
(xvii) a $V_H$ comprising CDRs 1, 2 and 3 of a sequence set forth in SEQ ID NO: 45 (optionally, also comprising the amino acid N-terminal to CDR1) and a $V_L$ comprising CDRs 1, 2 and 3 of a sequence set forth in SEQ ID NO: 5;
(xviii) a $V_H$ comprising a sequence set forth in SEQ ID NO: 45 and a $V_L$ comprising a sequence set forth in SEQ ID NO: 5;
(xix) a $V_H$ comprising CDRs 1, 2 and 3 of a sequence set forth in SEQ ID NO: 46 (optionally, also comprising the amino acid N-terminal to CDR1) and a $V_L$ comprising CDRs 1, 2 and 3 of a sequence set forth in SEQ ID NO: 5;
(xx) a $V_H$ comprising a sequence set forth in SEQ ID NO: 46 and a $V_L$ comprising a sequence set forth in SEQ ID NO: 5;
(xxi) a $V_H$ comprising CDRs 1, 2 and 3 of a sequence set forth in SEQ ID NO: 47 (optionally, also comprising the amino acid N-terminal to CDR1) and a $V_L$ comprising CDRs 1, 2 and 3 of a sequence set forth in SEQ ID NO: 5;
(xxii) a $V_H$ comprising a sequence set forth in SEQ ID NO: 47 and a $V_L$ comprising a sequence set forth in SEQ ID NO: 5;
(xxiii) a $V_H$ comprising CDRs 1, 2 and 3 of a sequence set forth in SEQ ID NO: 48 (optionally, also comprising the amino acid N-terminal to CDR1) and a $V_L$ comprising CDRs 1, 2 and 3 of a sequence set forth in SEQ ID NO: 5;
(xxiv) a $V_H$ comprising a sequence set forth in SEQ ID NO: 48 and a $V_L$ comprising a sequence set forth in SEQ ID NO: 5;
(xxv) a $V_H$ comprising CDRs 1, 2 and 3 of a sequence set forth in SEQ ID NO: 49 (optionally, also comprising the amino acid N-terminal to CDR1) and a $V_L$ comprising CDRs 1, 2 and 3 of a sequence set forth in SEQ ID NO: 5;
(xxvi) a $V_H$ comprising a sequence set forth in SEQ ID NO: 49 and a $V_L$ comprising a sequence set forth in SEQ ID NO: 5;
(xxvii) a $V_H$ comprising CDRs 1, 2 and 3 of a sequence set forth in SEQ ID NO: 50 (optionally, also comprising the amino acid N-terminal to CDR1) and a $V_L$ comprising CDRs 1, 2 and 3 of a sequence set forth in SEQ ID NO: 5;
(xxviii) a $V_H$ comprising a sequence set forth in SEQ ID NO: 50 and a $V_L$ comprising a sequence set forth in SEQ ID NO: 5;
(xxix) a $V_H$ comprising CDRs 1, 2 and 3 of a sequence set forth in SEQ ID NO: 51 (optionally, also comprising the amino acid N-terminal to CDR1) and a $V_L$ comprising CDRs 1, 2 and 3 of a sequence set forth in SEQ ID NO: 5;
(xxx) a $V_H$ comprising a sequence set forth in SEQ ID NO: 51 and a $V_L$ comprising a sequence set forth in SEQ ID NO: 5;
(xxxi) a $V_H$ comprising CDRs 1, 2 and 3 of a sequence set forth in SEQ ID NO: 52 (optionally, also comprising the amino acid N-terminal to CDR1) and a $V_L$ comprising CDRs 1, 2 and 3 of a sequence set forth in SEQ ID NO: 5;
(xxxii) a $V_H$ comprising a sequence set forth in SEQ ID NO: 52 and a $V_L$ comprising a sequence set forth in SEQ ID NO: 5;
(xxxiii) a $V_H$ comprising CDRs 1, 2 and 3 of a sequence set forth in SEQ ID NO: 53 (optionally, also comprising the amino acid N-terminal to CDR1) and a $V_L$ comprising CDRs 1, 2 and 3 of a sequence set forth in SEQ ID NO: 5;
(xxxiv) a $V_H$ comprising a sequence set forth in SEQ ID NO: 53 and a $V_L$ comprising a sequence set forth in SEQ ID NO: 5;
(xxxv) a $V_H$ comprising CDRs 1, 2 and 3 of a sequence set forth in SEQ ID NO: 54 (optionally, also comprising the amino acid N-terminal to CDR1) and a $V_L$ comprising CDRs 1, 2 and 3 of a sequence set forth in SEQ ID NO: 5;
(xxxvi) a $V_H$ comprising a sequence set forth in SEQ ID NO: 54 and a $V_L$ comprising a sequence set forth in SEQ ID NO: 5;
(xxxvii) a $V_H$ comprising CDRs 1, 2 and 3 of a sequence set forth in SEQ ID NO: 55 (optionally, also comprising the amino acid N-terminal to CDR1) and a $V_L$ comprising CDRs 1, 2 and 3 of a sequence set forth in SEQ ID NO: 5;
(xxxviii) a $V_H$ comprising a sequence set forth in SEQ ID NO: 55 and a $V_L$ comprising a sequence set forth in SEQ ID NO: 5;
(xxxix) a $V_H$ comprising CDRs 1, 2 and 3 of a sequence set forth in SEQ ID NO: 56 (optionally, also comprising the amino acid N-terminal to CDR1) and a $V_L$ comprising CDRs 1, 2 and 3 of a sequence set forth in SEQ ID NO: 5;
(xl) a $V_H$ comprising a sequence set forth in SEQ ID NO: 56 and a $V_L$ comprising a sequence set forth in SEQ ID NO: 5;
(xli) a $V_H$ comprising CDRs 1, 2 and 3 of a sequence set forth in SEQ ID NO: 57 (optionally, also comprising the amino acid N-terminal to CDR1) and a V_L comprising CDRs 1, 2 and 3 of a sequence set forth in SEQ ID NO: 5;
(xlii) a V_H comprising a sequence set forth in SEQ ID NO: 57 and a V_L comprising a sequence set forth in SEQ ID NO: 5;
(xliii) a V_H comprising CDRs 1, 2 and 3 of a sequence set forth in SEQ ID NO: 58 (optionally, also comprising the amino acid N-terminal to CDR1) and a V_L comprising CDRs 1, 2 and 3 of a sequence set forth in SEQ ID NO: 5;
(xliv) a V_H comprising a sequence set forth in SEQ ID NO: 58 and a V_L comprising a sequence set forth in SEQ ID NO: 5;
(xlv) a V_H comprising CDRs 1, 2 and 3 of a sequence set forth in SEQ ID NO: 59 (optionally, also comprising the amino acid N-terminal to CDR1) and a V_L comprising CDRs 1, 2 and 3 of a sequence set forth in SEQ ID NO: 5;
(xlvi) a V_H comprising a sequence set forth in SEQ ID NO: 59 and a V_L comprising a sequence set forth in SEQ ID NO: 5;
(xlvii) a V_H comprising CDRs 1, 2 and 3 of a sequence set forth in SEQ ID NO: 60 (optionally, also comprising the amino acid N-terminal to CDR1) and a V_L comprising CDRs 1, 2 and 3 of a sequence set forth in SEQ ID NO: 5;
(xlviii) a V_H comprising a sequence set forth in SEQ ID NO: 60 and a V_L comprising a sequence set forth in SEQ ID NO: 5;
(xlix) a V_H comprising CDRs 1, 2 and 3 of a sequence set forth in SEQ ID NO: 61 (optionally, also comprising the amino acid N-terminal to CDR1) and a V_L comprising CDRs 1, 2 and 3 of a sequence set forth in SEQ ID NO: 5;
(l) a V_H comprising a sequence set forth in SEQ ID NO: 61 and a V_L comprising a sequence set forth in SEQ ID NO: 5;
(li) a V_H comprising CDRs 1, 2 and 3 of a sequence set forth in SEQ ID NO: 62 (optionally, also comprising the amino acid N-terminal to CDR1) and a V_L comprising CDRs 1, 2 and 3 of a sequence set forth in SEQ ID NO: 5;
(lii) a V_H comprising a sequence set forth in SEQ ID NO: 62 and a V_L comprising a sequence set forth in SEQ ID NO: 5;
(liii) a V_H comprising CDRs 1, 2 and 3 of a sequence set forth in SEQ ID NO: 63 (optionally, also comprising the amino acid N-terminal to CDR1) and a V_L comprising CDRs 1, 2 and 3 of a sequence set forth in SEQ ID NO: 5;
(liv) a V_H comprising a sequence set forth in SEQ ID NO: 63 and a V_L comprising a sequence set forth in SEQ ID NO: 5;
(lv) a V_H comprising CDRs 1, 2 and 3 of a sequence set forth in SEQ ID NO: 64 (optionally, also comprising the amino acid N-terminal to CDR1) and a V_L comprising CDRs 1, 2 and 3 of a sequence set forth in SEQ ID NO: 5;
(lvi) a V_H comprising a sequence set forth in SEQ ID NO: 64 and a V_L comprising a sequence set forth in SEQ ID NO: 5;
(lvii) a V_H comprising CDRs 1, 2 and 3 of a sequence set forth in SEQ ID NO: 65 (optionally, also comprising the amino acid N-terminal to CDR1) and a V_L comprising CDRs 1, 2 and 3 of a sequence set forth in SEQ ID NO: 5;
(lviii) a V_H comprising a sequence set forth in SEQ ID NO: 65 and a V_L comprising a sequence set forth in SEQ ID NO: 5;
(lix) a V_H comprising CDRs 1, 2 and 3 of a sequence set forth in SEQ ID NO: 66 (optionally, also comprising the amino acid N-terminal to CDR1) and a V_L comprising CDRs 1, 2 and 3 of a sequence set forth in SEQ ID NO: 5;
(lx) a V_H comprising a sequence set forth in SEQ ID NO: 66 and a V_L comprising a sequence set forth in SEQ ID NO: 5;
(lxi) a V_H comprising CDRs 1, 2 and 3 of a sequence set forth in SEQ ID NO: 67 (optionally, also comprising the amino acid N-terminal to CDR1) and a V_L comprising CDRs 1, 2 and 3 of a sequence set forth in SEQ ID NO: 5;
(lxii) a V_H comprising a sequence set forth in SEQ ID NO: 67 and a V_L comprising a sequence set forth in SEQ ID NO: 5;
(lxiii) a V_H comprising CDRs 1, 2 and 3 of a sequence set forth in SEQ ID NO: 68 (optionally, also comprising the amino acid N-terminal to CDR1) and a V_L comprising CDRs 1, 2 and 3 of a sequence set forth in SEQ ID NO: 5;
(lxiv) a V_H comprising a sequence set forth in SEQ ID NO: 68 and a V_L comprising a sequence set forth in SEQ ID NO: 5;
(lxv) a V_H comprising CDRs 1, 2 and 3 of a sequence set forth in SEQ ID NO: 69 (optionally, also comprising the amino acid N-terminal to CDR1) and a V_L comprising CDRs 1, 2 and 3 of a sequence set forth in SEQ ID NO: 5;
(lxvi) a V_H comprising a sequence set forth in SEQ ID NO: 69 and a V_L comprising a sequence set forth in SEQ ID NO: 5;
(lxvii) a V_H comprising CDRs 1, 2 and 3 of a sequence set forth in SEQ ID NO: 70 (optionally, also comprising the amino acid N-terminal to CDR1) and a V_L comprising CDRs 1, 2 and 3 of a sequence set forth in SEQ ID NO: 5;
(lxviii) a V_H comprising a sequence set forth in SEQ ID NO: 37 and a V_L comprising a sequence set forth in SEQ ID NO: 5;
(lxix) a V_H comprising CDRs 1, 2 and 3 of a sequence set forth in SEQ ID NO: 70 (optionally, also comprising the amino acid N-terminal to CDR1) and a V_L comprising CDRs 1, 2 and 3 of a sequence set forth in SEQ ID NO: 5;
(lxx) a V_H comprising a sequence set forth in SEQ ID NO: 70 and a V_L comprising a sequence set forth in SEQ ID NO: 5;
(lxxi) a V_H comprising CDRs 1, 2 and 3 of a sequence set forth in SEQ ID NO: 37 (optionally, also comprising the amino acid N-terminal to CDR1) and a V_L comprising CDRs 1, 2 and 3 of a sequence set forth in SEQ ID NO: 6;
(lxxii) a V_H comprising a sequence set forth in SEQ ID NO: 37 and a V_L comprising a sequence set forth in SEQ ID NO: 6;
(lxviii) a V_H comprising CDRs 1, 2 and 3 of a sequence set forth in SEQ ID NO: 37 (optionally, also comprising the amino acid N-terminal to CDR1) and a V_L comprising CDRs 1, 2 and 3 of a sequence set forth in SEQ ID NO: 7;
(lxxiv) a V_H comprising a sequence set forth in SEQ ID NO: 37 and a V_L comprising a sequence set forth in SEQ ID NO: 7;
(lxxv) a V_H comprising CDRs 1, 2 and 3 of a sequence set forth in SEQ ID NO: 37 (optionally, also comprising the amino acid N-terminal to CDR1) and a V_L comprising CDRs 1, 2 and 3 of a sequence set forth in SEQ ID NO: 8;
(lxxvi) a V_H comprising a sequence set forth in SEQ ID NO: 37 and a V_L comprising a sequence set forth in SEQ ID NO: 8;
(lxxvii) a V_H comprising CDRs 1, 2 and 3 of a sequence set forth in SEQ ID NO: 37 (optionally, also comprising the amino acid N-terminal to CDR1) and a V_L comprising CDRs 1, 2 and 3 of a sequence set forth in SEQ ID NO: 9;
(lxxviii) a V_H comprising a sequence set forth in SEQ ID NO: 37 and a V_L comprising a sequence set forth in SEQ ID NO: 9;
(lxxix) a V_H comprising CDRs 1, 2 and 3 of a sequence set forth in SEQ ID NO: 37 (optionally, also comprising the amino acid N-terminal to CDR1) and a V_L comprising CDRs 1, 2 and 3 of a sequence set forth in SEQ ID NO: 10;
(lxxx) a V_H comprising a sequence set forth in SEQ ID NO: 37 and a V_L comprising a sequence set forth in SEQ ID NO: 10;
(lxxxi) a V_H comprising CDRs 1, 2 and 3 of a sequence set forth in SEQ ID NO: 37 (optionally, also comprising the amino acid N-terminal to CDR1) and a V_L comprising CDRs 1, 2 and 3 of a sequence set forth in SEQ ID NO: 11;
(lxxxii) a V_H comprising a sequence set forth in SEQ ID NO: 37 and a V_L comprising a sequence set forth in SEQ ID NO: 11;
(lxxxiii) a V_H comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 12;

(lxxxiv) a V$_H$ comprising a sequence set forth in SEQ ID NO: 37 and a V$_L$ comprising a sequence set forth in SEQ ID NO: 12;

(lxxxv) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 13;

(lxxxvi) a V$_H$ comprising a sequence set forth in SEQ ID NO: 37 and a V$_L$ comprising a sequence set forth in SEQ ID NO: 13;

(lxxxvii) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 14;

(lxxxviii) a V$_H$ comprising a sequence set forth in SEQ ID NO: 37 and a V$_L$ comprising a sequence set forth in SEQ ID NO: 14;

(lxxxix) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 15;

(xc) a V$_H$ comprising a sequence set forth in SEQ ID NO: 37 and a V$_L$ comprising a sequence set forth in SEQ ID NO: 15;

(xci) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 16;

(xcii) a V$_H$ comprising a sequence set forth in SEQ ID NO: 37 and a V$_L$ comprising a sequence set forth in SEQ ID NO: 16;

(xciii) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 17;

(xciv) a V$_H$ comprising a sequence set forth in SEQ ID NO: 37 and a V$_L$ comprising a sequence set forth in SEQ ID NO: 17;

(xcv) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 18;

(xcvi) a V$_H$ comprising a sequence set forth in SEQ ID NO: 37 and a V$_L$ comprising a sequence set forth in SEQ ID NO: 18;

(xcvii) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 19;

(xcviii) a V$_H$ comprising a sequence set forth in SEQ ID NO: 37 and a V$_L$ comprising a sequence set forth in SEQ ID NO: 19;

(xcix) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 20;

(c) a V$_H$ comprising a sequence set forth in SEQ ID NO: 37 and a V$_L$ comprising a sequence set forth in SEQ ID NO: 20;

(ci) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 21;

(cii) a V$_H$ comprising a sequence set forth in SEQ ID NO: 37 and a V$_L$ comprising a sequence set forth in SEQ ID NO: 21;

(ciii) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 22;

(civ) a V$_H$ comprising a sequence set forth in SEQ ID NO: 37 and a V$_L$ comprising a sequence set forth in SEQ ID NO: 22;

(cv) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 23;

(cvi) a V$_H$ comprising a sequence set forth in SEQ ID NO: 37 and a V$_L$ comprising a sequence set forth in SEQ ID NO: 23;

(cvii) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 24;

(cviii) a V$_H$ comprising a sequence set forth in SEQ ID NO: 37 and a V$_L$ comprising a sequence set forth in SEQ ID NO: 24;

(cix) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 25;

(cx) a V$_H$ comprising a sequence set forth in SEQ ID NO: 37 and a V$_L$ comprising a sequence set forth in SEQ ID NO: 25;

(cxi) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 26;

(cxii) a V$_H$ comprising a sequence set forth in SEQ ID NO: 37 and a V$_L$ comprising a sequence set forth in SEQ ID NO: 26;

(cxiii) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 27;

(cxiv) a V$_H$ comprising a sequence set forth in SEQ ID NO: 37 and a V$_L$ comprising a sequence set forth in SEQ ID NO: 27;

(cxv) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 28;

(cxvi) a V$_H$ comprising a sequence set forth in SEQ ID NO: 37 and a V$_L$ comprising a sequence set forth in SEQ ID NO: 28;

(cxvii) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 29;

(cxviii) a V$_H$ comprising a sequence set forth in SEQ ID NO: 37 and a V$_L$ comprising a sequence set forth in SEQ ID NO: 29;

(cxix) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 30;

(cxx) a V$_H$ comprising a sequence set forth in SEQ ID NO: 37 and a V$_L$ comprising a sequence set forth in SEQ ID NO: 30;

(cxxi) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 31;
(cxxii) a V$_H$ comprising a sequence set forth in SEQ ID NO: 37 and a V$_L$ comprising a sequence set forth in SEQ ID NO: 31;
(cxxiii) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 32;
(cxxiv) a V$_H$ comprising a sequence set forth in SEQ ID NO: 37 and a V$_L$ comprising a sequence set forth in SEQ ID NO: 32;
(cxxv) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 33;
(cxxvi) a V$_H$ comprising a sequence set forth in SEQ ID NO: 37 and a V$_L$ comprising a sequence set forth in SEQ ID NO: 33;
(cxxvii) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 34; or
(cxxviii) a V$_H$ comprising a sequence set forth in SEQ ID NO: 37 and a V$_L$ comprising a sequence set forth in SEQ ID NO: 34.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises:
(i) a V$_H$ comprising CDRs 1, 2 and 3 of a sequence set forth in SEQ ID NO: 49 (optionally, also comprising the amino acid N-terminal to CDR1) and a V$_L$ comprising CDRs 1, 2 and 3 of a sequence set forth in SEQ ID NO: 5;
(ii) a V$_H$ comprising a sequence set forth in SEQ ID NO: 49 and a V$_L$ comprising a sequence set forth in SEQ ID NO: 5;
(iii) a V$_H$ comprising CDRs 1, 2 and 3 of a sequence set forth in SEQ ID NO: 53 (optionally, also comprising the amino acid N-terminal to CDR1) and a V$_L$ comprising CDRs 1, 2 and 3 of a sequence set forth in SEQ ID NO: 5;
(iv) a V$_H$ comprising a sequence set forth in SEQ ID NO: 53 and a V$_L$ comprising a sequence set forth in SEQ ID NO: 5;
(v) a V$_H$ comprising CDRs 1, 2 and 3 of a sequence set forth in SEQ ID NO: 57 (optionally, also comprising the amino acid N-terminal to CDR1) and a V$_L$ comprising CDRs 1, 2 and 3 of a sequence set forth in SEQ ID NO: 5;
(vi) a V$_H$ comprising a sequence set forth in SEQ ID NO: 57 and a V$_L$ comprising a sequence set forth in SEQ ID NO: 5;
(vii) a V$_H$ comprising CDRs 1, 2 and 3 of a sequence set forth in SEQ ID NO: 58 (optionally, also comprising the amino acid N-terminal to CDR1) and a V$_L$ comprising CDRs 1, 2 and 3 of a sequence set forth in SEQ ID NO: 5;
(viii) a V$_H$ comprising a sequence set forth in SEQ ID NO: 58 and a V$_L$ comprising a sequence set forth in SEQ ID NO: 5;
(ix) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 8;
(x) a V$_H$ comprising a sequence set forth in SEQ ID NO: 37 and a V$_L$ comprising a sequence set forth in SEQ ID NO: 8;
(xi) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 15;
(xii) a V$_H$ comprising a sequence set forth in SEQ ID NO: 37 and a V$_L$ comprising a sequence set forth in SEQ ID NO: 15;
(xiii) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 16;
(xiv) a V$_H$ comprising a sequence set forth in SEQ ID NO: 37 and a V$_L$ comprising a sequence set forth in SEQ ID NO: 16;
(xv) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 18;
(xvi) a V$_H$ comprising a sequence set forth in SEQ ID NO: 37 and a V$_L$ comprising a sequence set forth in SEQ ID NO: 18;
(xvii) a V$_H$ comprising CDRs 1, 2 and 3 of a sequence set forth in SEQ ID NO: 37 (optionally, also comprising the amino acid N-terminal to CDR1) and a V$_L$ comprising CDRs 1, 2 and 3 of a sequence set forth in SEQ ID NO: 29; or
(xviii) a V$_H$ comprising a sequence set forth in SEQ ID NO: 37 and a V$_L$ comprising a sequence set forth in SEQ ID NO: 29.

In one example, the CDRs are as follows:
(i) Heavy chain CDR1: amino acids 31-35 of the recited sequence;
(ii) Heavy chain CDR2: amino acids 50-66 of the recited sequence (optionally, wherein any one or more of the five C-terminal amino acids are substituted with another naturally-occurring amino acid);
(iii) Heavy chain CDR3: amino acids 99-107 of the recited sequence;
(iv) Light chain CDR1: amino acids 24-34 of the recited sequence;
(v) Light chain CDR2: amino acids 50-56 of the recited sequence; and
(vi) Light chain CDR3: amino acids 89-97 of the recited sequence.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a V$_H$ comprising CDRs 1, 2 and 3 of a sequence set forth in SEQ ID NO: 49 and a V$_L$ comprising CDRs 1, 2 and 3 of a sequence set forth in SEQ ID NO: 5.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a V$_H$ comprising a sequence set forth in SEQ ID NO: 49 and a V$_L$ comprising a sequence set forth in SEQ ID NO: 5.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a V$_H$ comprising CDRs 1, 2 and 3 of a sequence set forth in SEQ ID NO: 53 (optionally, also comprising the amino acid N-terminal to CDR1) and a V$_L$ comprising CDRs 1, 2 and 3 of a sequence set forth in SEQ ID NO: 5.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising a sequence set forth in SEQ ID NO: 53 and a $V_L$ comprising a sequence set forth in SEQ ID NO: 5.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising CDRs 1, 2 and 3 of a sequence set forth in SEQ ID NO: 57 (optionally, also comprising the amino acid N-terminal to CDR1) and a $V_L$ comprising CDRs 1, 2 and 3 of a sequence set forth in SEQ ID NO: 5.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising a sequence set forth in SEQ ID NO: 57 and a $V_L$ comprising a sequence set forth in SEQ ID NO: 5.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising CDRs 1, 2 and 3 of a sequence set forth in SEQ ID NO: 58 (optionally, also comprising the amino acid N-terminal to CDR1) and a $V_L$ comprising CDRs 1, 2 and 3 of a sequence set forth in SEQ ID NO: 5.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising a sequence set forth in SEQ ID NO: 58 and a $V_L$ comprising a sequence set forth in SEQ ID NO: 5.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 8.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising a sequence set forth in SEQ ID NO: 37 and a $V_L$ comprising a sequence set forth in SEQ ID NO: 8.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 15.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising a sequence set forth in SEQ ID NO: 37 and a $V_L$ comprising a sequence set forth in SEQ ID NO: 15.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 16.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising a sequence set forth in SEQ ID NO: 37 and a $V_L$ comprising a sequence set forth in SEQ ID NO: 16.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 18.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising a sequence set forth in SEQ ID NO: 37 and a $V_L$ comprising a sequence set forth in SEQ ID NO: 18.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 29.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_H$ comprising a sequence set forth in SEQ ID NO: 37 and a $V_L$ comprising a sequence set forth in SEQ ID NO: 29.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises $V_H$ comprising a sequence set forth in SEQ ID NO: 37. In one example, the $V_L$ comprises CDRs 1, 2 and 3 of a sequence set forth in SEQ ID NO: 18.

The present disclosure also provides an IL-11Rα-binding protein comprising an antigen binding domain of an antibody, wherein the antigen binding domain binds to or specifically binds to IL-11Rα and neutralizes IL-11 signaling and wherein the antigen binding domain comprises a $V_L$ comprising a sequence set forth in SEQ ID NO: 18. In one example, the VH comprises CDRs 1, 2 and 3 of a sequence set forth in SEQ ID NO: 37.

In one example, the CDRs are as follows:
(i) Heavy chain CDR1: amino acids 31-35 of the recited sequence;
(ii) Heavy chain CDR2: amino acids 50-66 of the recited sequence (optionally, wherein any one or more of the five C-terminal amino acids are substituted with another naturally-occurring amino acid);
(iii) Heavy chain CDR3: amino acids 99-107 of the recited sequence;
(iv) Light chain CDR1: amino acids 24-34 of the recited sequence;
(v) Light chain CDR2: amino acids 50-56 of the recited sequence; and
(vi) Light chain CDR3: amino acids 89-97 of the recited sequence.

In one example, an IL-11Rα-binding protein described herein comprises at least a $V_H$ and a $V_L$, wherein the $V_H$ and $V_L$ bind to form a Fv comprising an antigen binding domain. The skilled artisan will understand that the antigen binding domain comprises the binding site of the antibody.

In one example, the $V_H$ and the $V_L$ are in a single polypeptide chain. For example, the protein is:
(i) a single chain Fv fragment (scFv);
(ii) a dimeric scFv (di-scFv);
(iii) one of (i) or (ii) linked to a constant region of an antibody, Fc or a heavy chain constant domain ($C_H$) 2 and/or $C_H3$; or
(iv) one of (i) or (ii) linked to a protein that binds to an immune effector cell.

In one example, the $V_L$ and $V_H$ are in separate polypeptide chains.

For example, the protein is:
(i) a diabody;
(ii) a triabody;
(iii) a tetrabody;
(iv) a Fab;
(v) a F(ab')$_2$;
(vi) a Fv;
(vii) one of (i) to (vi) linked to a constant region of an antibody, Fc or a heavy chain constant domain ($C_H$) 2 and/or $C_H3$;
(viii) one of (i) to (vi) linked to a protein that binds to an immune effector cell.

The foregoing proteins (described in the previous two lists) can also be referred to as antigen binding domains of antibodies.

In one example, the protein is an antibody, for example, a monoclonal antibody. In one example, the antibody is a naked antibody.

In one example, a protein (or antibody) is chimeric, de-immunized, humanized, human or primatized.

In one example, the protein or antibody is human.

The present disclosure additionally or alternatively provides an antibody that binds to IL-11Rα and neutralizes IL-11 signaling, the antibody comprising:
(i) a $V_H$ comprising CDRs 1, 2 and 3 of a sequence set forth in SEQ ID NO: 49 (optionally, also comprising the amino acid N-terminal to CDR1) and a $V_L$ comprising CDRs 1, 2 and 3 of a sequence set forth in SEQ ID NO: 5;
(ii) a $V_H$ comprising a sequence set forth in SEQ ID NO: 49 and a $V_L$ comprising a sequence set forth in SEQ ID NO: 5;
(iii) a $V_H$ comprising CDRs 1, 2 and 3 of a sequence set forth in SEQ ID NO: 53 (optionally, also comprising the amino acid N-terminal to CDR1) and a $V_L$ comprising CDRs 1, 2 and 3 of a sequence set forth in SEQ ID NO: 5;
(iv) a $V_H$ comprising a sequence set forth in SEQ ID NO: 53 and a $V_L$ comprising a sequence set forth in SEQ ID NO: 5;
(v) a $V_H$ comprising CDRs 1, 2 and 3 of a sequence set forth in SEQ ID NO: 57 (optionally, also comprising the amino acid N-terminal to CDR1) and a $V_L$ comprising CDRs 1, 2 and 3 of a sequence set forth in SEQ ID NO: 5;
(vi) a $V_H$ comprising a sequence set forth in SEQ ID NO: 57 and a $V_L$ comprising a sequence set forth in SEQ ID NO: 5;
(vii) a $V_H$ comprising CDRs 1, 2 and 3 of a sequence set forth in SEQ ID NO: 58 (optionally, also comprising the amino acid N-terminal to CDR1) and a $V_L$ comprising CDRs 1, 2 and 3 of a sequence set forth in SEQ ID NO: 5;
(viii) a $V_H$ comprising a sequence set forth in SEQ ID NO: 58 and a $V_L$ comprising a sequence set forth in SEQ ID NO: 5;
(ix) a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 8;
(x) a $V_H$ comprising a sequence set forth in SEQ ID NO: 37 and a $V_L$ comprising a sequence set forth in SEQ ID NO: 8;
(xi) a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 15;
(xii) a $V_H$ comprising a sequence set forth in SEQ ID NO: 37 and a $V_L$ comprising a sequence set forth in SEQ ID NO: 15;
(xiii) a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 16;
(xiv) a $V_H$ comprising a sequence set forth in SEQ ID NO: 37 and a $V_L$ comprising a sequence set forth in SEQ ID NO: 16;
(xv) a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 18;
(xvi) a $V_H$ comprising a sequence set forth in SEQ ID NO: 37 and a $V_L$ comprising a sequence set forth in SEQ ID NO: 18;
(xvii) a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 29; or
(xviii) a $V_H$ comprising a sequence set forth in SEQ ID NO: 37 and a $V_L$ comprising a sequence set forth in SEQ ID NO: 29.

The present disclosure also provides an antibody that binds to IL-11Rα and neutralizes IL-11 signaling, the antibody comprising $V_H$ comprising a sequence set forth in SEQ ID NO: 37. In one example, the $V_L$ comprises CDRs 1, 2 and 3 of a sequence set forth in SEQ ID NO: 18.

(xix) The present disclosure also provides an antibody that binds to IL-11Rα and neutralizes IL-11 signaling, the antibody comprising a $V_L$ comprising a sequence set forth in SEQ ID NO: 18. In one example, the VH comprises CDRs 1, 2 and 3 of a sequence set forth in SEQ ID NO: 37.

In one example, the CDRs are as follows:
(i) Heavy chain CDR1: amino acids 31-35 of the recited sequence;
(ii) Heavy chain CDR2: amino acids 50-66 of the recited sequence (optionally, wherein any one or more of the five C-terminal amino acids are substituted with another naturally-occurring amino acid);
(iii) Heavy chain CDR3: amino acids 99-107 of the recited sequence;

(iv) Light chain CDR1: amino acids 24-34 of the recited sequence;
(v) Light chain CDR2: amino acids 50-56 of the recited sequence; and
(vi) Light chain CDR3: amino acids 89-97 of the recited sequence.

Sequences of exemplary $V_H$ and $V_L$ are described in Table 1.

The present disclosure also provides an antibody that binds to IL-11Rα and neutralizes IL-11 signaling, the antibody comprising a $V_H$ comprising CDRs 1, 2 and 3 of a sequence set forth in SEQ ID NO: 49 (optionally, also comprising the amino acid N-terminal to CDR1) and a $V_L$ comprising CDRs 1, 2 and 3 of a sequence set forth in SEQ ID NO: 5.

The present disclosure also provides an antibody that binds to IL-11Rα and neutralizes IL-11 signaling, the antibody comprising a $V_H$ comprising a sequence set forth in SEQ ID NO: 49 and a $V_L$ comprising a sequence set forth in SEQ ID NO: 5.

The present disclosure also provides an antibody that binds to IL-11Rα and neutralizes IL-11 signaling, the antibody comprising a $V_H$ comprising CDRs 1, 2 and 3 of a sequence set forth in SEQ ID NO: 53 (optionally, also comprising the amino acid N-terminal to CDR1) and a $V_L$ comprising CDRs 1, 2 and 3 of a sequence set forth in SEQ ID NO: 5.

The present disclosure also provides an antibody that binds to IL-11Rα and neutralizes IL-11 signaling, the antibody comprising a $V_H$ comprising a sequence set forth in SEQ ID NO: 53 and a $V_L$ comprising a sequence set forth in SEQ ID NO: 5.

The present disclosure also provides an antibody that binds to IL-11Rα and neutralizes IL-11 signaling, the antibody comprising a $V_H$ comprising CDRs 1, 2 and 3 of a sequence set forth in SEQ ID NO: 57 (optionally, also comprising the amino acid N-terminal to CDR1) and a $V_L$ comprising CDRs 1, 2 and 3 of a sequence set forth in SEQ ID NO: 5.

The present disclosure also provides an antibody that binds to IL-11Rα and neutralizes IL-11 signaling, the antibody comprising a $V_H$ comprising a sequence set forth in SEQ ID NO: 57 and a $V_L$ comprising a sequence set forth in SEQ ID NO: 5.

The present disclosure also provides an antibody that binds to IL-11Rα and neutralizes IL-11 signaling, the antibody comprising a $V_H$ comprising CDRs 1, 2 and 3 of a sequence set forth in SEQ ID NO: 58 (optionally, also comprising the amino acid N-terminal to CDR1) and a $V_L$ comprising CDRs 1, 2 and 3 of a sequence set forth in SEQ ID NO: 5.

The present disclosure also provides an antibody that binds to IL-11Rα and neutralizes IL-11 signaling, the antibody comprising a $V_H$ comprising a sequence set forth in SEQ ID NO: 58 and a $V_L$ comprising a sequence set forth in SEQ ID NO: 5.

The present disclosure also provides an antibody that binds to IL-11Rα and neutralizes IL-11 signaling, the antibody comprising a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 8.

The present disclosure also provides an antibody that binds to IL-11Rα and neutralizes IL-11 signaling, the antibody comprising a $V_H$ comprising a sequence set forth in SEQ ID NO: 37 and a $V_L$ comprising a sequence set forth in SEQ ID NO: 8.

The present disclosure also provides an antibody that binds to IL-11Rα and neutralizes IL-11 signaling, the antibody comprising a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 15.

The present disclosure also provides an antibody that binds to IL-11Rα and neutralizes IL-11 signaling, the antibody comprising a $V_H$ comprising a sequence set forth in SEQ ID NO: 37 and a $V_L$ comprising a sequence set forth in SEQ ID NO: 15.

The present disclosure also provides an antibody that binds to IL-11Rα and neutralizes IL-11 signaling, the antibody comprising a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 16.

The present disclosure also provides an antibody that binds to IL-11Rα and neutralizes IL-11 signaling, the antibody comprising a $V_H$ comprising a sequence set forth in SEQ ID NO: 37 and a $V_L$ comprising a sequence set forth in SEQ ID NO: 16.

The present disclosure also provides an antibody that binds to IL-11Rα and neutralizes IL-11 signaling, the antibody comprising a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 18.

The present disclosure also provides an antibody that binds to IL-11Rα and neutralizes IL-11 signaling, the antibody comprising a $V_H$ comprising a sequence set forth in SEQ ID NO: 37 and a $V_L$ comprising a sequence set forth in SEQ ID NO: 18.

The present disclosure also provides an antibody that binds to IL-11Rα and neutralizes IL-11 signaling, the antibody comprising a $V_H$ comprising CDRs 1, 2 and 3 of a sequence set forth in SEQ ID NO: 37 (optionally, also comprising the amino acid N-terminal to CDR1) and a $V_L$ comprising CDRs 1, 2 and 3 of a sequence set forth in SEQ ID NO: 29.

The present disclosure also provides an antibody that binds to IL-11Rα and neutralizes IL-11 signaling, the antibody comprising a $V_H$ comprising a sequence set forth in SEQ ID NO: 37 and a $V_L$ comprising a sequence set forth in SEQ ID NO: 29.

In one example, the CDRs are as follows:
(i) Heavy chain CDR1: amino acids 31-35 of the recited sequence;
(ii) Heavy chain CDR2: amino acids 50-66 of the recited sequence (optionally, wherein any one or more of the five C-terminal amino acids are substituted with another naturally-occurring amino acid);
(iii) Heavy chain CDR3: amino acids 99-107 of the recited sequence;
(iv) Light chain CDR1: amino acids 24-34 of the recited sequence;
(v) Light chain CDR2: amino acids 50-56 of the recited sequence; and
(vi) Light chain CDR3: amino acids 89-97 of the recited sequence.

Reference herein to a protein or antibody that "binds to" IL-11Rα provides literal support for a protein or antibody that "binds specifically to" or "specifically binds to" IL-11R.

The present disclosure also provides antigen binding domains or antigen binding fragments of the foregoing antibodies.

In one example, a protein or antibody as described herein comprises a human constant region, e.g., an IgG constant region, such as an IgG1, IgG2, IgG3 or IgG4 constant region or mixtures thereof. In the case of an antibody or protein comprising a $V_H$ and a $V_L$, the $V_H$ can be linked to a heavy chain constant region and the $V_L$ can be linked to a light chain constant region.

The C-terminal lysine of the heavy chain constant region of a whole antibody (or am IL-11Rα-binding protein comprising a constant region or a $C_H3$) of the disclosure may be removed, for example, during production or purification of the antibody or protein, or by recombinantly engineering the nucleic acid encoding a heavy chain of the antibody. Accordingly, whole antibodies (or IL-11R-binding proteins) may comprise populations with all C-terminal lysine residues removed, populations with no C-terminal lysine residues removed, and/or populations having a mixture of protein with and without the C-terminal lysine residue. In some examples, the populations may additionally comprise protein in which the C-terminal lysine residue is removed in one of the heavy chain constant regions. Similarly, a composition of whole antibodies may comprise the same or a similar mix of antibody populations with or without the C-terminal lysine residue.

In one example, a protein or antibody as described herein comprises a constant region of an IgG4 antibody or a stabilized constant region of an IgG4 antibody. In one example, the protein or antibody comprises an IgG4 constant region with a proline at position 241 (according to the numbering system of Kabat (Kabat et al., Sequences of Proteins of Immunological Interest Washington D.C. United States Department of Health and Human Services, 1987 and/or 1991)).

In one example, the heavy chain constant region comprises a sequence from position 119 to position 445 of SEQ ID NO: 83. In one example a protein or antibody as described herein or a composition of a protein or antibody as described herein, comprises a heavy chain constant region, including a stabilized heavy chain constant region, comprising a mixture of sequences fully or partially with or without the C-terminal lysine residue.

In one example, an antibody of the disclosure comprises a $V_H$ disclosed herein linked or fused to an IgG4 constant region or stabilized IgG4 constant region (e.g., as discussed above) and the $V_L$ is linked to or fused to a kappa light chain constant region.

The functional characteristics of an IL-11Rα-binding protein of the disclosure will be taken to apply mutatis mutandis to an antibody of the disclosure.

In one example, an IL-11Rα-binding protein or antibody as described herein is isolated and/or recombinant.

In one example, an IL-11Rα-binding protein or antibody of the disclosure is conjugated to another compound, for example, a detectable label or a compound that extends the half-life of the protein or antibody, such as polyethylene glycol or an albumin binding protein. Other suitable compounds are described herein.

The present disclosure also provides a nucleic acid encoding the IL-11Rα-binding protein or antibody of the present disclosure or a polypeptide thereof.

In one example, such a nucleic acid is included in an expression construct in which the nucleic acid is operably linked to a promoter. Such an expression construct can be in a vector, e.g., a plasmid.

In examples of the disclosure directed to single polypeptide chain IL-11Rα-binding proteins, the expression construct may comprise a promoter linked to a nucleic acid encoding that polypeptide chain.

In examples directed to multiple polypeptide chains that form an IL-11Rα-binding protein, an expression construct comprises a nucleic acid encoding a polypeptide comprising, e.g., a $V_H$ operably linked to a promoter and a nucleic acid encoding a polypeptide comprising, e.g., a $V_L$ operably linked to a promoter.

In another example, the expression construct is a bicistronic expression construct, e.g., comprising the following operably linked components in 5' to 3' order:
(i) a promoter
(ii) a nucleic acid encoding a first polypeptide;
(iii) an internal ribosome entry site; and
(iv) a nucleic acid encoding a second polypeptide,
wherein the first polypeptide comprises a $V_H$ and the second polypeptide comprises a $V_L$, or vice versa.

The present disclosure also contemplates separate expression constructs one of which encodes a first polypeptide comprising a $V_H$ and another of which encodes a second polypeptide comprising a $V_L$. For example, the present disclosure also provides a composition comprising:
(i) a first expression construct comprising a nucleic acid encoding a polypeptide comprising a $V_H$ operably linked to a promoter; and
(ii) a second expression construct comprising a nucleic acid encoding a polypeptide comprising a $V_L$ operably linked to a promoter.

The present disclosure also provides an isolated or recombinant cell expressing an IL-11Rα-binding protein of the disclosure.

In one example, the cell comprises the expression construct of the disclosure or:
(i) a first expression construct comprising a nucleic acid encoding a polypeptide comprising a $V_H$ operably linked to a promoter; and
(ii) a second expression construct comprising a nucleic acid encoding a polypeptide comprising a $V_L$ operably linked to a promoter,
wherein the first and second polypeptides associate to form an IL-11Rα-binding protein of the present disclosure.

Examples of cells of the present disclosure include bacterial cells, yeast cells, insect cells or mammalian cells.

The present disclosure additionally provides methods for producing an IL-11Rα-binding protein or antibody of the disclosure. For example, such a method involves maintaining the expression construct(s) of the disclosure under conditions sufficient for the IL-11Rα-binding protein or antibody to be produced.

In one example, a method for producing an IL-11Rα-binding protein or antibody of the disclosure comprises culturing the cell of the disclosure under conditions sufficient for the IL-11Rα-binding protein or antibody to be produced and, optionally, secreted.

In one example, the method for producing an IL-11Rα-binding protein or antibody of the disclosure additionally comprises isolating the protein or antibody and, optionally, formulating the IL-11Rα-binding protein or antibody into a pharmaceutical composition.

The present disclosure additionally provides a composition comprising an IL-11Rα-binding protein or antibody of the disclosure and a pharmaceutically acceptable carrier.

In some examples, the composition comprises:
(i) an antibody of the disclosure comprising a C-terminal lysine residue from the heavy chain;
(ii) an antibody of the disclosure lacking a C-terminal lysine residue from the heavy chain; and/or
(iii) an antibody of the disclosure comprising a C-terminal lysine residue on one heavy chain and lacking a C-terminal lysine residue on another (or the other) heavy chain, and, optionally, a pharmaceutically acceptable carrier.

The present disclosure also provides a method for treating or preventing an IL-11-mediated condition in a subject, the method comprising administering the IL-11Rα-binding protein, antibody or composition of the disclosure. In this regard, an IL-11Rα-binding protein, antibody or composition can be used to prevent a relapse of a condition, and this is considered preventing the condition.

In one example, the IL-11-mediated condition is an autoimmune condition, an inflammatory condition, a wasting condition, bone conditions or cancer.

Exemplary autoimmune conditions include arthritis, inflammatory bowel disease and psoriasis.

Exemplary inflammatory conditions include infection-induced inflammation (e.g., inflammation induced by *M. tuberculosis*), gastric inflammation (e.g., associated with gastric cancer), inflammatory airway conditions (e.g., asthma, chronic obstructive pulmonary disease (COPD), rhinitis or allergy) or inflammatory dermatitis (e.g., atopic dermatitis).

Exemplary wasting conditions include cachexia (e.g., cancer cachexia or cachexia caused by renal failure) or sarcopenia.

Exemplary bone conditions include osteoporosis (including post-menopausal osteoporosis), bone fracture, bone resorption/damage caused by cancer (e.g., metastatic bone cancer, myeloma or Paget's disease of bone) and bone resorption/damage caused by treatment of cancer (e.g., chemotherapy, hormone ablation or hormone inhibition).

Exemplary cancers include hematologic cancers, cancers of epithelial origin, liver cancer, pancreatic cancer, gastric cancer, osteosarcoma, endometrial cancer and ovarian cancer.

In one example, the cancer or the bone condition is metastasis of a cancer to bone.

The present disclosure also provides a method for inhibiting or neutralizing IL-11 in a subject, the method comprising administering the IL-11Rα-binding protein, antibody or composition of the disclosure. In one example, the subject suffers from an IL-11-mediated condition.

The present disclosure also provides a method for preventing pregnancy in a subject, the method comprising administering the IL-11Rα-binding protein, antibody or composition of the disclosure.

In one example, a method described herein comprises administering between about 0.05 mg/kg and 30 mg/kg of the IL-11Rα-binding protein or antibody. For example, the method comprising administering between 0.1 mg/kg and 10 mg/kg or between 0.2 mg/kg and 5 mg/kg of the IL-11Rα-binding protein or antibody. In one example, the method comprises administering about 0.5-2.0 mg/kg of the IL-11Rα-binding protein or antibody.

The present disclosure also provides for use of an IL-11Rα-binding protein or antibody as described herein in any example in medicine.

The present disclosure also provides for use of an IL-11Rα-binding protein or antibody as described herein according to any example in the manufacture of a medicament to treat an IL-11-mediated condition. Exemplary conditions are described herein.

The present disclosure also provides a method for localizing and/or detecting and/or diagnosing and/or prognosing an IL-11-mediated condition associated with a cell expressing IL-11Rα, the method comprising detecting in vivo an IL-11Rα-binding protein or antibody as described herein bound to the IL-11Rα expressing cell, if present, wherein the IL-11Rα-binding protein or antibody is conjugated to a detectable tag.

In one example, the method additionally comprises administering the IL-11Rα-binding protein to the subject.

The present disclosure also provides a method for detecting IL-11Rα or a cell expressing same in a sample, the method comprising contacting the sample with a protein or antibody as described herein according to any example such that a complex forms and detecting the complex, wherein detection of the complex is indicative of IL-11Rα or a cell expressing same in the sample. In one example, the method is performed ex vivo or in vitro.

The present disclosure also provides a method for diagnosing or prognosing a IL-11-mediated condition, the method comprising performing a method as described herein according to any example to detect IL-11Rα or a cell expressing same, wherein detection of the IL-11Rα or cell expressing same is diagnostic or prognostic of the condition. In one example, the method is performed ex vivo or in vitro. Exemplary IL-11Rα-mediated conditions are described herein.

The present disclosure also provides a kit (e.g., a package or article of manufacture) comprising an IL-11Rα-binding protein or antibody as described herein according to any example, optionally, packaged with instructions for use in a method as described herein.

KEY TO SEQUENCE LISTING

SEQ ID NO 1: amino acid sequence of *Homo sapiens* pre-IL-11Rα

SEQ ID NO 2: amino acid sequence of *Macaca fascicularis* pre-IL-11 Rα

SEQ ID NO 3: amino acid sequence of polypeptide comprising amino acids 23 to 363 of SEQ ID NO: 1, a 8×HIS tag and a serine at a position corresponding to position 248 of SEQ ID NO: 1 (also referred to as "WT F/L")

SEQ ID NO 4: amino acid sequence of *Homo sapiens* gp130

SEQ ID NO 5: amino acid sequence of $V_L$ chain of antibody 8E2

SEQ ID NO 6: amino acid sequence of $V_L$ chain of antibody TS-303

SEQ ID NO 7: amino acid sequence of $V_L$ chain of antibody TS-305

SEQ ID NO 8: amino acid sequence of $V_L$ chain of antibody TS-306

SEQ ID NO 9: amino acid sequence of $V_L$ chain of antibody TS-307

SEQ ID NO 10: amino acid sequence of $V_L$ chain of antibody TS-310

SEQ ID NO 11: amino acid sequence of $V_L$ chain of antibody TS-311

SEQ ID NO 12: amino acid sequence of $V_L$ chain of antibody TS-312

SEQ ID NO 13: amino acid sequence of $V_L$ chain of antibody TS-313

SEQ ID NO 14: amino acid sequence of $V_L$ chain of antibody TS-322

SEQ ID NO 15: amino acid sequence of $V_L$ chain of antibody TS-2

SEQ ID NO 16: amino acid sequence of $V_L$ chain of antibody TS-4

SEQ ID NO 17: amino acid sequence of $V_L$ chain of antibody TS-6

SEQ ID NO 18: amino acid sequence of $V_L$ chain of antibody TS-7

SEQ ID NO 19: amino acid sequence of $V_L$ chain of antibody TS-9

SEQ ID NO 20: amino acid sequence of $V_L$ chain of antibody TS-13

SEQ ID NO 21: amino acid sequence of $V_L$ chain of antibody TS-14

SEQ ID NO 22: amino acid sequence of $V_L$ chain of antibody TS-17
SEQ ID NO 23: amino acid sequence of $V_L$ chain of antibody TS-20
SEQ ID NO 24: amino acid sequence of $V_L$ chain of antibody TS-21
SEQ ID NO 25: amino acid sequence of $V_L$ chain of antibody TS-22
SEQ ID NO 26: amino acid sequence of $V_L$ chain of antibody TS-29
SEQ ID NO 27: amino acid sequence of $V_L$ chain of antibody TS-32
SEQ ID NO 28: amino acid sequence of $V_L$ chain of antibody TS-49
SEQ ID NO 29: amino acid sequence of $V_L$ chain of antibody TS-51
SEQ ID NO 30: amino acid sequence of $V_L$ chain of antibody TS-55
SEQ ID NO 31: amino acid sequence of $V_L$ chain of antibody TS-57
SEQ ID NO 32: amino acid sequence of $V_L$ chain of antibody TS-58
SEQ ID NO 33: amino acid sequence of $V_L$ chain of antibody TS-63
SEQ ID NO 34: amino acid sequence of $V_L$ chain of antibody TS-64
SEQ ID NO 35: amino acid sequence of consensus of $V_L$ chain of 8E2 antibody and derivatives
SEQ ID NO 36: amino acid sequence of consensus of $V_L$ chain of 8E2 antibody and select derivatives
SEQ ID NO 37: amino acid sequence of $V_H$ chain of antibody 8E2
SEQ ID NO 38: amino acid sequence of $V_H$ chain of antibody TS-66
SEQ ID NO 39: amino acid sequence of $V_H$ chain of antibody TS-69
SEQ ID NO 40: amino acid sequence of $V_H$ chain of antibody TS-71
SEQ ID NO 41: amino acid sequence of $V_H$ chain of antibody TS-76
SEQ ID NO 42: amino acid sequence of $V_H$ chain of antibody TS-79
SEQ ID NO 43: amino acid sequence of $V_H$ chain of antibody TS-82
SEQ ID NO 44: amino acid sequence of $V_H$ chain of antibody TS-88
SEQ ID NO 45: amino acid sequence of $V_H$ chain of antibody TS-89
SEQ ID NO 46: amino acid sequence of $V_H$ chain of antibody TS-91
SEQ ID NO 47: amino acid sequence of $V_H$ chain of antibody TS-92
SEQ ID NO 48: amino acid sequence of $V_H$ chain of antibody TS-97
SEQ ID NO 49: amino acid sequence of $V_H$ chain of antibody TS-101
SEQ ID NO 50: amino acid sequence of $V_H$ chain of antibody TS-103
SEQ ID NO 51: amino acid sequence of $V_H$ chain of antibody TS-104
SEQ ID NO 52: amino acid sequence of $V_H$ chain of antibody TS-107
SEQ ID NO 53: amino acid sequence of $V_H$ chain of antibody TS-108
SEQ ID NO 54: amino acid sequence of $V_H$ chain of antibody TS-115
SEQ ID NO 55: amino acid sequence of $V_H$ chain of antibody TS-129
SEQ ID NO 56: amino acid sequence of $V_H$ chain of antibody TS-133
SEQ ID NO 57: amino acid sequence of $V_H$ chain of antibody TS-134
SEQ ID NO 58: amino acid sequence of $V_H$ chain of antibody TS-135
SEQ ID NO 59: amino acid sequence of $V_H$ chain of antibody TS-136
SEQ ID NO 60: amino acid sequence of $V_H$ chain of antibody TS-140
SEQ ID NO 61: amino acid sequence of $V_H$ chain of antibody TS-143
SEQ ID NO 62: amino acid sequence of $V_H$ chain of antibody TS-151
SEQ ID NO 63: amino acid sequence of $V_H$ chain of antibody TS-156
SEQ ID NO 64: amino acid sequence of $V_H$ chain of antibody TS-213
SEQ ID NO 65: amino acid sequence of $V_H$ chain of antibody TS-214
SEQ ID NO 66: amino acid sequence of $V_H$ chain of antibody TS-215
SEQ ID NO 67: amino acid sequence of $V_H$ chain of antibody TS-218
SEQ ID NO 68: amino acid sequence of $V_H$ chain of antibody TS-221
SEQ ID NO 69: amino acid sequence of $V_H$ chain of antibody TS-222
SEQ ID NO 70: amino acid sequence of $V_H$ chain of antibody TS-224
SEQ ID NO 71: amino acid sequence of consensus of $V_H$ chain of 8E2 antibody and derivatives
SEQ ID NO 72: amino acid sequence of consensus of $V_H$ chain of 8E2 antibody and select derivatives
SEQ ID NO 73: amino acid sequence of $V_L$ chain of antibody 8E4
SEQ ID NO 74: amino acid sequence of $V_H$ chain of antibody 8E4
SEQ ID NO 75: amino acid sequence of $V_L$ chain of antibody 8D10
SEQ ID NO 76: amino acid sequence of $V_H$ chain of antibody 8D10
SEQ ID NO 77: amino acid sequence of consensus of CDR1 of $V_L$ chain of 8E2 antibody and derivatives
SEQ ID NO 78: amino acid sequence of consensus of CDR3 of $V_L$ chain of 8E2 antibody and derivatives
SEQ ID NO 79: amino acid sequence of consensus of CDR1 of $V_H$ chain of 8E2 antibody and derivatives
SEQ ID NO 80: amino acid sequence of consensus of CDR2 of $V_H$ chain of 8E2 antibody and derivatives
SEQ ID NO 81: amino acid sequence of consensus of CDR3 of $V_H$ chain of 8E2 antibody and derivatives
SEQ ID NO 82: amino acid sequence of *Mus musculus* pre-IL-11Rα
SEQ ID NO 83: amino acid sequence of heavy chain of antibody 8E2
SEQ ID NO 84: amino acid sequence of light chain of antibody 8E2
SEQ ID NO 85: amino acid sequence of a polypeptide comprising amino acids 23 to 318 of *Homo sapiens* IL-11Rα (SEQ ID NO: 1), a 8×HIS tag and a serine at a position corresponding to position 248 of SEQ ID NO:1 (also referred to as "WT D½")
SEQ ID NO: 86: amino acid sequence of a polypeptide comprising amino acids 23-110 of *Homo sapiens* IL-11Rα

(SEQ ID NO: 1) and amino acids 111-367 of *Mus musculus* IL-11Rα (SEQ ID NO: 82) (in which there is a serine at a position corresponding to position 206 of SEQ ID NO: 82) and a 8×HIS tag SEQ ID NO: 87: amino acid sequence of a polypeptide comprising amino acids 23-215 of *Homo sapiens* IL-11Rα (SEQ ID NO: 1) and amino acids 216-367 of *Mus musculus* IL-11Rα (SEQ ID NO: 82) and a 8×HIS tag SEQ ID NO: 88: amino acid sequence of a polypeptide comprising amino acids 23-318 of *Homo sapiens* IL-11Rα (SEQ ID NO: 1) (in which there is a serine at a position corresponding to position 248 of SEQ ID NO: 1) and amino acids 319-367 of *Mus musculus* IL-11Rα (SEQ ID NO: 82) and a 8×HIS tag SEQ ID NO: 89: amino acid sequence of a polypeptide comprising amino acids 24-215 of *Mus musculus* IL-11Rα (SEQ ID NO: 82) (in which there is a serine at a position corresponding to position 206 of SEQ ID NO: 82) and amino acids 216-363 of *Homo sapiens* IL-11Rα (SEQ ID NO: 1) and a 8×HIS tag SEQ ID NO: 90: amino acid sequence of a polypeptide comprising amino acids 24 to 367 of *Mus musculus* sIL-11Rα (SEQ ID NO: 82), a 8×HIS tag and a serine at a position corresponding to position 206 of SEQ ID NO:82

SEQ ID NO 91: amino acid sequence of light chain of antibody 8E4

SEQ ID NO 92: amino acid sequence of heavy chain of antibody 8E4

SEQ ID NO 93: amino acid sequence of light chain of antibody 8D10

SEQ ID NO 94: amino acid sequence of heavy chain of antibody 8D10

SEQ ID NO: 95: amino acid sequence of SEQ ID NO: 85 comprising a glutamic acid at a position corresponding to position 117 of SEQ ID NO: 1.

SEQ ID NO: 96: amino acid sequence of SEQ ID NO: 85 comprising an arginine at a position corresponding to position 66 of SEQ ID NO: 1.

SEQ ID NO: 97: amino acid sequence of SEQ ID NO: 85 comprising a serine at a position corresponding to position 65 of SEQ ID NO: 1.

SEQ ID NO: 98: amino acid sequence of SEQ ID NO: 85 comprising a serine at a position corresponding to position 101 of SEQ ID NO: 1.

SEQ ID NO: 99: amino acid sequence of SEQ ID NO: 85 comprising an alanine at a position corresponding to position 178 of SEQ ID NO: 1.

SEQ ID NO: 100: amino acid sequence of mature *Homo sapiens* IL-11Rα

SEQ ID NO: 101: amino acid sequence of mature *Macaca fascicularis* IL-11 Rα

SEQ ID NO: 102: amino acid sequence of mature *Mus musculus* sIL-11Rα

SEQ ID NO: 103: amino acid sequence of consensus of 8E2L1 as depicted in FIG. 1

SEQ ID NO: 104: amino acid sequence of consensus of 8E2L3.1 as depicted in FIG. 1

SEQ ID NO: 105: amino acid sequence of consensus of 8E2L3.2 as depicted in FIG. 1

SEQ ID NO: 106: amino acid sequence of consensus of 8E2H1 as depicted in FIG. 2

SEQ ID NO: 107: amino acid sequence of consensus of 8E2H2 as depicted in FIG. 2

SEQ ID NO: 108: amino acid sequence of consensus of 8E2H3.1 as depicted in FIG. 2

SEQ ID NO: 109: amino acid sequence of consensus of 8E2H3.2 as depicted in FIG. 2

BRIEF DESCRIPTION OF THE DRAWINGS

FIG. 1 is a diagrammatic representation showing an alignment of CDRs of the $V_L$ of antibody 8E2 and affinity matured forms thereof. The consensus sequences listed (SEQ ID NOs: 103-105) represents the most commonly occurring amino acid at each position and was determined using the MegAlign software. Other than the consensus sequences, the sequences are derived from the antibodies set out in Table 1.

FIG. 2 is a diagrammatic representation showing an alignment of CDRs of the $V_H$ of antibody 8E2 and affinity matured forms thereof. The consensus sequences listed (SEQ ID NOs: 106-109) represents the most commonly occurring amino acid at each position and was determined using the MegAlign software. Other than the consensus sequences, the sequences are derived from the antibodies set out in Table 1.

FIGS. 3A, B, C and D are diagrammatic representations showing sequences of variable regions of the 8E2 antibody and derivatives. FIG. 3A shows sequences of $V_L$ regions of 8E2 and its antibody derivatives and the consensus sequence of $V_L$ regions of 8E2 and its antibody derivatives. FIG. 3B shows sequences of $V_L$ regions of 8E2 and select antibody derivatives and the consensus sequence of $V_L$ regions of 8E2 and select antibody derivatives. FIG. 3C shows sequences of $V_H$ regions of 8E2 and its antibody derivatives and the consensus sequence of $V_H$ regions of 8E2 and its antibody derivatives. FIG. 3D shows sequences of $V_H$ regions of 8E2 and select antibody derivatives and the consensus sequence of $V_H$ regions of 8E2 and select antibody derivatives. Boxed regions contain CDRs (as indicated) as defined by the Kabat numbering system.

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat *Sequences of Proteins of Immunological Interest*, National Institutes of Health, Bethesda, Md., 1987 and 1991, Bork et al., *J. Mol. Biol.* 242, 309-320, 1994, Chothia and Lesk *J. Mol. Biol.* 196:901-917, 1987, Chothia et al. *Nature* 342, 877-883, 1989 and/or Al-Lazikani et al., *J Mol Biol* 273, 927-948, 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Reference herein to a range of, e.g., residues, will be understood to be inclusive. For example, reference to "a region comprising amino acids 56 to 65" will be understood in an inclusive manner, i.e., the region comprises a sequence of amino acids as numbered 56, 57, 58, 59, 60, 61, 62, 63, 64 and 65 in a specified sequence.

Selected Definitions

For the purposes of nomenclature only and not limitation an exemplary sequence of a human precursor IL-11Rα (pre-IL-11Rα) is set out in NCBI Reference Sequence: NP_001136256.1 (and set out in SEQ ID NO: 1). A sequence of a mature human IL-11Rα is set forth in SEQ ID NO: 100. In the case of the sequence set forth in NP_001136256.1, a mature protein lacks amino acids 1 to 22. Positions of amino acids are often referred to herein by reference to pre-IL-11Rα. The positions in mature IL-11Rα is readily determined by accounting for the signal sequence (amino acids 1-22 in the case of SEQ ID NO: 1). An exemplary sequence of a cynomolgus monkey pre-IL-11Rα is set out in SEQ ID NO: 2 and a mature IL-11Rα in SEQ ID NO: 101. An exemplary sequence of a mouse pre-IL-11Rα is set out in SEQ ID NO: 82 and a mature IL-11Rα in SEQ ID NO: 102. The sequence of IL-11Rα from other species can be determined using sequences provided herein and/or in publicly available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989)) Reference to human IL-11Rα may be abbreviated to hIL-11Rα, reference to cynomolgus monkey IL-11Rα may be abbreviated to cynoIL-11Rα, and reference to mouse IL-11Rα may be abbreviated to mIL-11Rα. Reference to soluble IL-11Rα refers to polypeptides comprising the extracellular region of IL-11Rα, e.g., amino acids 23-363 or 23-318 of SEQ ID NO: 1. In the present studies soluble forms of the receptor comprising amino acids 23-363 or 23-318 of SEQ ID NO: 1 with a serine substitution at position 248 were used (e.g. SEQ ID NO: 3 or 85) and the corresponding segment of mIL-11Rα with the serine substitution at a position corresponding to position 206 of SEQ ID NO: 82 (e.g., SEQ ID NO 90) for studies on the mouse receptor. These serine mutations were introduced into the soluble polypeptides to improve expression and prevent aggregation of the polypeptides. Various point mutations of the soluble receptor of SEQ ID NO: 3 and SEQ ID NO: 85 have also been utilized (e.g., see SEQ ID NOs: 95-99). These soluble polypeptides are representative of hIL-11Rα or mIL-11Rα as demonstrated by the ability of the IL-11Rα-binding proteins of the disclosure to bind to the relevant receptor when expressed on the surface of a cell. Accordingly, studies using the mutant polypeptides are a model of studies using hIL-11Rα and/or mIL-11Rα.

Reference herein to IL-11 includes native forms of IL-11 and mutant forms thereof retaining an ability to bind to IL-11Rα (e.g., hIL-11Rα) and induce signaling.

Reference herein to a particular domain of hIL-11Rα will be understood to mean the following:

Immunoglobulin-like (IG-like) domain: amino acids 23-110 of SEQ ID NO: 1;

First fibronectin III domain: amino acids 111-215 of SEQ ID NO: 1;

Second fibronectin III domain: amino acids 216-370 of SEQ ID NO: 1;

Transmembrane domain: amino acids 371-391 of SEQ ID NO: 1; and

Cytoplasmic domain: amino acids 392-422 of SEQ ID NO: 1.

The term "isolated protein" or "isolated polypeptide" is a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

As used herein, the term "antigen binding domain" shall be taken to mean a region of an antibody that is capable of specifically binding to an antigen, i.e., a $V_H$ or a $V_L$ or an Fv comprising both a $V_H$ and a $V_L$. The antigen binding domain need not be in the context of an entire antibody, e.g., it can be in isolation (e.g., a domain antibody) or in another form, e.g., as described herein, such as a scFv.

For the purposes for the present disclosure, the term "antibody" includes a protein capable of specifically binding to one or a few closely related antigens (e.g., IL-11Rα) by virtue of an antigen binding domain contained within a Fv. This term includes four chain antibodies (e.g., two light chains and two heavy chains), recombinant or modified antibodies (e.g., chimeric antibodies, humanized antibodies, human antibodies, CDR-grafted antibodies, primatized antibodies, de-immunized antibodies, synhumanized antibodies, half-antibodies, bispecific antibodies). An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50 to 70 kD) covalently linked and two light chains (~23 kDa each). A light chain generally comprises a variable region (if present) and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is aligned with and disulfide bonded to the first constant domain of the heavy chain ($C_H1$ which is 330 to 440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region between the $C_H1$ and $C_H2$ constant domains. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. In one example, the antibody is a murine (mouse or rat) antibody or a primate (such as, human) antibody. In one example the antibody heavy chain is missing a C-terminal lysine residue. In one example, the antibody is humanized, synhumanized, chimeric, CDR-grafted or deimmunized.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and, includes amino acid sequences of complementarity determining regions (CDRs); i.e., CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region domain ($V_H$ or $V_L$) typically has three CDRs identified as CDR1, CDR2 and CDR3. In one example, the amino acid positions assigned to CDRs and FRs are defined according to Kabat *Sequences of Proteins of Immunological Interest*, National Institutes of Health, Bethesda, Md., 1987 and 1991 (also referred to herein as "the Kabat numbering system"). In another example, the amino acid positions assigned to CDRs and FRs are defined according to the Enhanced Chothia Numbering Scheme (http://www.bioinfo.org.uk/mdex.html). According to the numbering system of Kabat, $V_H$ FRs and CDRs are positioned as follows: residues 1 to 30 (FR1), 31 to 35 (CDR1), 36 to 49 (FR2), 50 to 65 (CDR2), 66 to 94 (FR3), 95 to 102 (CDR3) and 103 to 113 (FR4). According to the numbering system of Kabat, $V_L$ FRs and CDRs are positioned as follows: residues 1 to 23 (FR1), 24 to 34 (CDR1), 35 to 49 (FR2), 50 to 56 (CDR2), 57 to 88 (FR3), 89 to 97 (CDR3) and 98 to 107 (FR4). The present disclosure is not limited to FRs and CDRs as defined by the Kabat numbering system, but includes all numbering systems, including the canonical numbering system or of Chothia and Lesk *J. Mol. Biol.* 196: 901-917, 1987; Chothia et al., *Nature* 342: 877-883, 1989; and/or Al-Lazikani et al., *J. Mol. Biol.* 273: 927-948, 1997; the numbering system of Honneghr and Plükthun *J. Mol. Biol.* 309: 657-670, 2001; or the IMGT system discussed in Giudicelli et al., *Nucleic Acids Res.* 25: 206-211 1997. In one example, the CDRs are defined according to the Kabat numbering system. Optionally, heavy chain CDR2 according to the Kabat numbering system does not comprise the five C-terminal amino acids listed herein or any one or more of those amino acids are substituted with another naturally-occurring amino acid. In this regard, Padlan et al., *FASEB J.*, 9: 133-139, 1995 established that the five C-terminal amino acids of heavy chain CDR2 are not generally involved in antigen binding.

"Framework regions" (FRs) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding domain, i.e., capable of specifically binding to an antigen. The $V_H$ and the $V_L$ which form the antigen binding domain can be in a single polypeptide chain or in different polypeptide chains. Furthermore, an Fv of the disclosure (as well as any protein of the disclosure) may have multiple antigen binding domains which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "Fab$_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of an IL-11Rα-binding protein or an antigen binding domain thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that an IL-11Rα-binding protein of the disclosure reacts or associates more frequently, more rapidly, with greater duration and/or with greater affinity with a particular antigen or cell expressing same than it does with alternative antigens or cells. For example, an IL-11Rα-binding protein binds to IL-11Rα (e.g., hIL-11Rα or a polypeptide comprising a region thereof, e.g., a polypeptide of SEQ ID NO: 3 or 85) with materially greater affinity (e.g., 1.5 fold or 2 fold or 5 fold or 10 fold or 20 fold or 40 fold or 60 fold or 80 fold to 100 fold or 150 fold or 200 fold) than it does to other interleukin receptors or to antigens commonly recognized by polyreactive natural antibodies (i.e., by naturally occurring antibodies known to bind a variety of antigens naturally found in humans). In an example of the present disclosure, an IL-11Rα-binding protein that "specifically binds" to one form of hIL-11Rα or a polypeptide comprising a region thereof (e.g., the extracellular region of hIL-11Rα) or a polypeptide a sequence set forth in SEQ ID NO: 3 or 85 with an affinity at least 1.5 fold or 2 fold or greater (e.g., 5 fold or 10 fold or 20 fold r 50 fold or 100 fold or 200 fold) than it does to a mutant form of SEQ ID NO: 3 comprising a sequence set forth in SEQ ID NO: 95. Generally, but not necessarily, reference to binding means specific binding, and each term shall be understood to provide explicit support for the other term.

As used herein, the term "does not detectably bind" shall be understood to mean that an IL-11Rα-binding protein, e.g., an antibody, binds to a candidate antigen at a level less than 10%, or 8% or 6% or 5% above background. The background can be the level of binding signal detected in the absence of the protein and/or in the presence of a negative control protein (e.g., an isotype control antibody) and/or the level of binding detected in the presence of a negative control antigen. The level of binding is detected using biosensor analysis (e.g. Biacore) in which the IL-11Rα-binding protein is immobilized and contacted with an antigen.

As used herein, the term "does not significantly bind" shall be understood to mean that the level of binding of an IL-11Rα-binding protein of the disclosure to a polypeptide is not statistically significantly higher than background, e.g., the level of binding signal detected in the absence of the IL-11Rα-binding protein and/or in the presence of a negative control protein (e.g., an isotype control antibody) and/or the level of binding detected in the presence of a negative control polypeptide. The level of binding is detected using biosensor analysis (e.g. Biacore) in which the IL-11Rα-binding protein is immobilized and contacted with an antigen.

As used herein, phrases referring to "reduced binding" or "binding being at a lower level" in relation to an antigen will be understood to mean that an IL-11Rα-binding protein, e.g., antibody, binds to an antigen (e.g., a mutant of SEQ ID NO: 3 as described herein, such as a mutant comprising the sequence set forth in SEQ ID NO: 95) with an affinity at least about 1.5 fold or 2 fold or 5 fold or 10 fold or 20 fold or 50 fold or 100 fold or 200 fold less than a control epitope or antigen (e.g. SEQ ID NO: 3).

An IL-11Rα-binding protein or antibody may be considered to "preferentially bind" to a polypeptide if it binds that polypeptide with a dissociation constant ($K_D$) that is less than the protein's or antibody's $K_D$ for another polypeptide. In one example, an IL-11Rα-binding protein or antibody is considered to preferentially bind to a polypeptide if it binds the polypeptide with an affinity (i.e., $K_D$) that is at least about 1.5 fold or 2 fold or 5 fold or 10 fold or 20 fold or 50 fold or 100 fold or 200 fold more than the protein's or antibody's $K_D$ for another polypeptide.

As used herein, the term "capable of binding to hIL-11Rα and cynoIL-11Rα" will be understood to mean that an IL-11Rα-binding protein cross-reacts with hIL-11Rα and cynoIL-11Rα, i.e., binding to either protein.

For the purposes of clarification and as will be apparent to the skilled artisan based on the exemplified subject matter herein, reference to "affinity" in this specification is a reference to $K_D$ of a protein or antibody.

For the purposes of clarification and as will be apparent to the skilled artisan based on the description herein, reference to an "affinity of at least about" will be understood to mean that the affinity (or $K_D$) is equal to the recited value or higher (i.e., the value recited as the affinity is lower), i.e., an affinity of 2 nM is greater than an affinity of 3 nM. Stated another way, this term could be "an affinity of X or less", wherein X is a value recited herein.

An "IC$_{50}$ of at least about" will be understood to mean that the IC$_{50}$ is equal to the recited value or lower (i.e., the value recited as the IC$_{50}$ is lower), i.e., an IC$_{50}$ of 2 µg/ml is greater than an IC$_{50}$ of 1 µg/ml. Stated another way, this term could be "an IC$_{50}$ of X or less", wherein X is a value recited herein.

As used herein, the term "epitope" (syn. "antigenic determinant") shall be understood to mean a region of IL-11Rα to which an IL-11Rα-binding protein comprising an antigen binding domain of an antibody binds. This term is not necessarily limited to the specific residues or structure to which the IL-11Rα-binding protein makes contact. For example, this term includes the region spanning amino acids contacted by the IL-11Rα-binding protein and 5-10 (or more) or 2-5 or 1-3 amino acids outside of this region. In some examples, the epitope comprises a series of discontinuous amino acids that are positioned close to one another when IL-11Rα-binding protein is folded, i.e., a "conformational epitope". The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain examples, may have specific three dimensional structural characteristics, and/or specific charge characteristics.

The term "competitively inhibits" shall be understood to mean that an IL-11Rα-binding protein of the disclosure (or an antigen binding domain thereof) reduces or prevents binding of a recited antibody or IL-11Rα-binding protein to IL-11Rα, e.g., to hIL-11Rα. This may be due to the IL-11Rα-binding protein (or antigen binding domain) and antibody binding to the same or an overlapping epitope. It will be apparent from the foregoing that the IL-11Rα-binding protein need not completely inhibit binding of the antibody, rather it need only reduce binding by a statistically significant amount, for example, by at least about 10% or 20% or 30% or 40% or 50% or 60% or 70% or 80% or 90% or 95%. Preferably, the IL-11Rα-binding protein reduces binding of the antibody by at least about 30%, more preferably by at least about 50%, more preferably, by at least about 70%, still more preferably by at least about 75%, even more preferably, by at least about 80% or 85% and even more preferably, by at least about 90%. Methods for determining competitive inhibition of binding are known in the art and/or described herein. For example, the antibody is exposed to IL-11Rα either in the presence or absence of the IL-11Rα-binding protein. If less antibody binds in the presence of the IL-11Rα-binding protein than in the absence of the IL-11Rα-binding protein, the protein is considered to competitively inhibit binding of the antibody. In one example, the competitive inhibition is not due to steric hindrance.

"Overlapping" in the context of two epitopes shall be taken to mean that two epitopes share a sufficient number of amino acid residues to permit an IL-11Rα-binding protein (or antigen binding domain thereof) that binds to one epitope to competitively inhibit the binding of an IL-11Rα-binding protein (or antigen binding domain) that binds to the other epitope. For example, the "overlapping" epitopes share at least 1 or 2 or 3 or 4 or 5 or 6 or 7 or 8 or 9 or 20 amino acids.

As used herein, the term "neutralize" shall be taken to mean that a protein is capable of blocking, reducing or preventing IL-11-mediated signaling in a cell through the IL-11Rα. Methods for determining neutralization are known in the art and/or described herein.

As used herein, the term "condition" refers to a disruption of or interference with normal function, and is not to be limited to any specific condition, and will include diseases or disorders.

As used herein, an "IL-11-associated condition" refers to any condition that is caused by or associated with an excess of IL-11 or cells expressing IL-11 or with administration of IL-11. The skilled artisan will be readily able to determine such conditions. Exemplary conditions are described herein.

As used herein, the terms "preventing", "prevent" or "prevention" include administering an IL-11Rα-binding protein of the disclosure to thereby stop or hinder the development of at least one symptom of a condition. This term also encompasses treatment of a subject in remission to prevent or hinder relapse.

As used herein, the terms "treating", "treat" or "treatment" include administering an IL-11Rα-binding protein described herein to thereby reduce or eliminate at least one symptom of a specified disease or condition.

As used herein, the term "subject" shall be taken to mean any animal including humans, for example a mammal. Exemplary subjects include but are not limited to humans and non-human primates. For example, the subject is a human.

Antibodies

In one example, an IL-11Rα-binding protein as described herein according to any example is an antibody.

Methods for generating antibodies are known in the art and/or described in Harlow and Lane (editors) Antibodies: A Laboratory Manual, Cold Spring Harbor Laboratory, (1988). Generally, in such methods IL-11Rα (e.g., hIL-11Rα) or a region thereof (e.g., an extracellular region) or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are one exemplary form of antibody contemplated by the present disclosure. The term "monoclonal antibody" or "mAb" refers to a homogeneous antibody population capable of binding to the same antigen(s), for example, to the same epitope within the antigen. This term is not intended to be limited with regard to the source of the antibody or the manner in which it is made.

For the production of mAbs any one of a number of known techniques may be used, such as, for example, the procedure exemplified in U.S. Pat. No. 4,196,265 or Harlow and Lane (1988), supra.

For example, a suitable animal is immunized with an immunogen under conditions sufficient to stimulate antibody producing cells. Rodents such as rabbits, mice and rats are exemplary animals. Mice genetically-engineered to express human antibodies and, for example, do not express murine antibodies, can also be used to generate an antibody of the present disclosure (e.g., as described in WO2002/066630).

Following immunization, somatic cells with the potential for producing antibodies, specifically B lymphocytes (B cells), are selected for use in the mAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like).

Alternatively, ABL-MYC technology (NeoClone, Madison Wis. 53713, USA) is used to produce cell lines secreting MAbs (e.g., as described in Largaespada et al, *J. Immunol. Methods.* 197: 85-95, 1996).

Antibodies can also be produced or isolated by screening a display library, e.g., a phage display library, e.g., as described in U.S. Pat. No. 6,300,064 and/or U.S. Pat. No. 5,885,793. For example, the present inventors have isolated fully human antibodies from a phage display library.

As described herein, some IL-11Rα-binding proteins of the present disclosure that bind hIL-11Rα cross-react with cynoIL-11Rα and/or bind to some mutant forms of hIL-11Rα or polypeptides comprising regions of hIL-11Rα that have been mutated and/or not others. These characteristics can be used in the generation of an antibody or an IL-11Rα-binding protein.

For example, a phage display library is screened with a polypeptide comprising SEQ ID NO: 3 to identify proteins that bind thereto. Mutant forms of the polypeptide (e.g., wherein valine at a position corresponding to position 117 of SEQ ID NO: 1 is substituted with glutamic acid (e.g., comprising a sequence of SEQ ID NO: 95)) to which the IL-11Rα-binding protein is not to detectably bind are then used to remove cross-reactive proteins and/or mutant forms of the polypeptide (e.g., comprising a sequence of SEQ ID NO: 97, 98 or 99) to which the IL-11Rα-binding protein is to bind are used to isolate proteins that are correctly cross-reactive. A screening process for immunization of a non-human mammal can also be devised based on the foregoing.

In another example, a phage display library is screened or an animal is immunized with a polypeptide comprising the extracellular domain (or a region corresponding to amino acids 23-215 or 110-215 of SEQ ID NO: 1) of cynoIL-11Rα and identified IL-11Rα-binding protein and/or antibodies are screened to identify those that are cross-reactive with hIL-11Rα and/or a polypeptide of SEQ ID NO: 3 and/or 85.

In a further example, an IL-11Rα or an extracellular region thereof (optionally a mutant form to which 8E2 or 8D10 or 8E4 binds) is contacted with one of the foregoing antibodies. A phage display library is then brought into contact with the IL-11Rα or region and phage expressing proteins that can compete with the antibody for binding selected.

In a still further example, a chimeric protein comprising, e.g., a mouse IL-11Rα in which an epitope of interest from a hIL-11Rα is substituted for the corresponding mouse sequence. This chimeric protein is then used to immunize mice (which are less likely to induce an immune response against the mouse protein) and/or to screen a phage display library. The resulting antibodies/proteins are then screened to identify those that bind to hIL-11Rα (particularly at the epitope of interest) and not mouse IL-11Rα.

The antibody of the present disclosure may be a synthetic antibody. For example, the antibody is a chimeric antibody, a humanized antibody, a human antibody synhumanized antibody, primatized antibody or a de-immunized antibody.

Deimmunized, Chimeric, CDR Grafted, Humanized, Synhumanized, Primatized, Human and Composite IL-11Rα-Binding Proteins The IL-11Rα-binding proteins of the present disclosure may be CDR grafted proteins which include CDRs from an antibody from a non-human species (e.g., mouse or rat or non-human primate) grafted onto or inserted into FRs from a human antibody or which include CDRs from an antibody from one type of antibody (e.g., one type of human antibody) grafted onto or inserted into FRs from another type of antibody (e.g., another type of human antibody). This term also encompasses a composite IL-11Rα-binding protein comprising, for example, one or more CDR grafted variable regions and one or more, e.g., human variable regions, chimeric variable regions, synhumanized variable regions or primatized variable regions.

The IL-11Rα-binding proteins of the present disclosure may be a humanized protein.

The term "humanized protein" shall be understood to refer to a protein comprising a human-like variable region, which includes CDRs from an antibody from a non-human species (e.g., mouse or rat or non-human primate) grafted onto or inserted into FRs from a human antibody (this type of antibody is falls within the class of "CDR-grafted antibody"). Humanized IL-11Rα-binding proteins also include proteins in which one or more residues of the human protein are modified by one or more amino acid substitutions and/or one or more FR residues of the human protein are replaced by corresponding non-human residues. Humanized proteins may also comprise residues which are found in neither the human antibody or in the non-human antibody. Any additional regions of the protein (e.g., Fc region) are generally human. Humanization can be performed using a method known in the art, e.g., U.S. Pat. No. 5,225,539, U.S. Pat. No. 6,054,297, U.S. Pat. No. 7,566,771 or U.S. Pat. No. 5,585,089. The term "humanized protein" also encompasses a super-humanized protein, e.g., as described in U.S. Pat. No. 7,732,578. This term also encompasses a composite protein comprising, for example, one or more humanized variable regions and one or more, e.g., human variable regions, chimeric variable regions, synhumanized variable regions or primatized variable regions.

The IL-11Rα-binding proteins of the present disclosure may be human IL-11Rα-binding proteins. The term "human protein" as used herein refers to proteins having variable and, optionally, constant antibody regions found in humans, e.g. in the human germline or somatic cells or from libraries produced using such regions. The "human" proteins can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein). These "human proteins" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in U.S. Pat. No. 5,565,332). This term also encompasses affinity matured forms of such antibodies. For the purposes of the present disclosure, a human protein will also be considered to include a protein comprising FRs from a human antibody or FRs comprising sequences from a consensus sequence of human FRs and in which one or more of the CDRs are random or semi-random, e.g., as described in U.S. Pat. No. 6,300,064 and/or U.S. Pat. No. 6,248,516.

Exemplary human IL-11Rα-binding proteins are antibodies comprising the following pairs of variable regions:

(i) a $V_H$ comprising a sequence set forth in SEQ ID NO: 37 and a $V_L$ comprising a sequence set forth in SEQ ID NO: 5;
(ii) a $V_H$ comprising a sequence set forth in SEQ ID NO: 38 and a $V_L$ comprising a sequence set forth in SEQ ID NO: 5;
(iii) a $V_H$ comprising a sequence set forth in SEQ ID NO: 39 and a $V_L$ comprising a sequence set forth in SEQ ID NO: 5;
(iv) a $V_H$ comprising a sequence set forth in SEQ ID NO: 40 and a $V_L$ comprising a sequence set forth in SEQ ID NO: 5;
(v) a $V_H$ comprising a sequence set forth in SEQ ID NO: 41 and a $V_L$ comprising a sequence set forth in SEQ ID NO: 5;
(vi) a $V_H$ comprising a sequence set forth in SEQ ID NO: 42 and a $V_L$ comprising a sequence set forth in SEQ ID NO: 5;
(vii) a $V_H$ comprising a sequence set forth in SEQ ID NO: 43 and a $V_L$ comprising a sequence set forth in SEQ ID NO: 5;
(viii) a $V_H$ comprising a sequence set forth in SEQ ID NO: 44 and a $V_L$ comprising a sequence set forth in SEQ ID NO: 5;
(ix) a $V_H$ comprising a sequence set forth in SEQ ID NO: 45 and a $V_L$ comprising a sequence set forth in SEQ ID NO: 5;
(x) a $V_H$ comprising a sequence set forth in SEQ ID NO: 46 and a $V_L$ comprising a sequence set forth in SEQ ID NO: 5;
(xi) a $V_H$ comprising a sequence set forth in SEQ ID NO: 47 and a $V_L$ comprising a sequence set forth in SEQ ID NO: 5;
(xii) a $V_H$ comprising a sequence set forth in SEQ ID NO: 48 and a $V_L$ comprising a sequence set forth in SEQ ID NO: 5;
(xiii) a $V_H$ comprising a sequence set forth in SEQ ID NO: 49 and a $V_L$ comprising a sequence set forth in SEQ ID NO: 5;
(xiv) a $V_H$ comprising a sequence set forth in SEQ ID NO: 50 and a $V_L$ comprising a sequence set forth in SEQ ID NO: 5;
(xv) a $V_H$ comprising a sequence set forth in SEQ ID NO: 51 and a $V_L$ comprising a sequence set forth in SEQ ID NO: 5;
(xvi) a $V_H$ comprising a sequence set forth in SEQ ID NO: 52 and a $V_L$ comprising a sequence set forth in SEQ ID NO: 5;
(xvii) a $V_H$ comprising a sequence set forth in SEQ ID NO: 53 and a $V_L$ comprising a sequence set forth in SEQ ID NO: 5;
(xviii) a $V_H$ comprising a sequence set forth in SEQ ID NO: 54 and a $V_L$ comprising a sequence set forth in SEQ ID NO: 5;
(xix) a $V_H$ comprising a sequence set forth in SEQ ID NO: 55 and a $V_L$ comprising a sequence set forth in SEQ ID NO: 5;
(xx) a $V_H$ comprising a sequence set forth in SEQ ID NO: 56 and a $V_L$ comprising a sequence set forth in SEQ ID NO: 5;
(xxi) a $V_H$ comprising a sequence set forth in SEQ ID NO: 57 and a $V_L$ comprising a sequence set forth in SEQ ID NO: 5;
(xxii) a $V_H$ comprising a sequence set forth in SEQ ID NO: 58 and a $V_L$ comprising a sequence set forth in SEQ ID NO: 5;
(xxiii) a $V_H$ comprising a sequence set forth in SEQ ID NO: 59 and a $V_L$ comprising a sequence set forth in SEQ ID NO: 5;
(xxiv) a $V_H$ comprising a sequence set forth in SEQ ID NO: 60 and a $V_L$ comprising a sequence set forth in SEQ ID NO: 5;
(xxv) a $V_H$ comprising a sequence set forth in SEQ ID NO: 61 and a $V_L$ comprising a sequence set forth in SEQ ID NO: 5;
(xxvi) a $V_H$ comprising a sequence set forth in SEQ ID NO: 62 and a $V_L$ comprising a sequence set forth in SEQ ID NO: 5;
(xxvii) a $V_H$ comprising a sequence set forth in SEQ ID NO: 63 and a $V_L$ comprising a sequence set forth in SEQ ID NO: 5;
(xxviii) a $V_H$ comprising a sequence set forth in SEQ ID NO: 64 and a $V_L$ comprising a sequence set forth in SEQ ID NO: 5;
(xxix) a $V_H$ comprising a sequence set forth in SEQ ID NO: 65 and a $V_L$ comprising a sequence set forth in SEQ ID NO: 5;
(xxx) a $V_H$ comprising a sequence set forth in SEQ ID NO: 66 and a $V_L$ comprising a sequence set forth in SEQ ID NO: 5;
(xxxi) a $V_H$ comprising a sequence set forth in SEQ ID NO: 67 and a $V_L$ comprising a sequence set forth in SEQ ID NO: 5;
(xxxii) a $V_H$ comprising a sequence set forth in SEQ ID NO: 68 and a $V_L$ comprising a sequence set forth in SEQ ID NO: 5;
(xxxiii) a $V_H$ comprising a sequence set forth in SEQ ID NO: 69 and a $V_L$ comprising a sequence set forth in SEQ ID NO: 5;
(xxxiv) a $V_H$ comprising a sequence set forth in SEQ ID NO: 37 and a $V_L$ comprising a sequence set forth in SEQ ID NO: 5;
(xxxv) a $V_H$ comprising a sequence set forth in SEQ ID NO: 70 and a $V_L$ comprising a sequence set forth in SEQ ID NO: 5;
(xxxvi) a $V_H$ comprising a sequence set forth in SEQ ID NO: 37 and a $V_L$ comprising a sequence set forth in SEQ ID NO: 6;
(xxxvii) a $V_H$ comprising a sequence set forth in SEQ ID NO: 37 and a $V_L$ comprising a sequence set forth in SEQ ID NO: 7;
(xxxviii) a $V_H$ comprising a sequence set forth in SEQ ID NO: 37 and a $V_L$ comprising a sequence set forth in SEQ ID NO: 8;
(xxxix) a $V_H$ comprising a sequence set forth in SEQ ID NO: 37 and a $V_L$ comprising a sequence set forth in SEQ ID NO: 9;
(xl) a $V_H$ comprising a sequence set forth in SEQ ID NO: 37 and a $V_L$ comprising a sequence set forth in SEQ ID NO: 10;
(xli) a $V_H$ comprising a sequence set forth in SEQ ID NO: 37 and a $V_L$ comprising a sequence set forth in SEQ ID NO: 11;
(ilii) a $V_H$ comprising a sequence set forth in SEQ ID NO: 37 and a $V_L$ comprising a sequence set forth in SEQ ID NO: 12;
(xliii) a $V_H$ comprising a sequence set forth in SEQ ID NO: 37 and a $V_L$ comprising a sequence set forth in SEQ ID NO: 13;
(xliv) a $V_H$ comprising a sequence set forth in SEQ ID NO: 37 and a $V_L$ comprising a sequence set forth in SEQ ID NO: 14;
(xlv) a $V_H$ comprising a sequence set forth in SEQ ID NO: 37 and a $V_L$ comprising a sequence set forth in SEQ ID NO: 15;
(xlvi) a $V_H$ comprising a sequence set forth in SEQ ID NO: 37 and a $V_L$ comprising a sequence set forth in SEQ ID NO: 16;
(xlvii) a $V_H$ comprising a sequence set forth in SEQ ID NO: 37 and a $V_L$ comprising a sequence set forth in SEQ ID NO: 17;
(xlviii) a $V_H$ comprising a sequence set forth in SEQ ID NO: 37 and a $V_L$ comprising a sequence set forth in SEQ ID NO: 18;
(xlix) a $V_H$ comprising a sequence set forth in SEQ ID NO: 37 and a $V_L$ comprising a sequence set forth in SEQ ID NO: 19;
(l) a $V_H$ comprising a sequence set forth in SEQ ID NO: 37 and a $V_L$ comprising a sequence set forth in SEQ ID NO: 20;
(li) a $V_H$ comprising a sequence set forth in SEQ ID NO: 37 and a $V_L$ comprising a sequence set forth in SEQ ID NO: 21;
(lii) a $V_H$ comprising a sequence set forth in SEQ ID NO: 37 and a $V_L$ comprising a sequence set forth in SEQ ID NO: 22;

(liii) a $V_H$ comprising a sequence set forth in SEQ ID NO: 37 and a $V_L$ comprising a sequence set forth in SEQ ID NO: 23;
(liv) a $V_H$ comprising a sequence set forth in SEQ ID NO: 37 and a $V_L$ comprising a sequence set forth in SEQ ID NO: 24;
(lv) a $V_H$ comprising a sequence set forth in SEQ ID NO: 37 and a $V_L$ comprising a sequence set forth in SEQ ID NO: 25;
(lvi) a $V_H$ comprising a sequence set forth in SEQ ID NO: 37 and a $V_L$ comprising a sequence set forth in SEQ ID NO: 26;
(lvii) a $V_H$ comprising a sequence set forth in SEQ ID NO: 37 and a $V_L$ comprising a sequence set forth in SEQ ID NO: 27;
(lviii) a $V_H$ comprising a sequence set forth in SEQ ID NO: 37 and a $V_L$ comprising a sequence set forth in SEQ ID NO: 28;
(lix) a $V_H$ comprising a sequence set forth in SEQ ID NO: 37 and a $V_L$ comprising a sequence set forth in SEQ ID NO: 29;
(lx) a $V_H$ comprising a sequence set forth in SEQ ID NO: 37 and a $V_L$ comprising a sequence set forth in SEQ ID NO: 30;
(lxi) a $V_H$ comprising a sequence set forth in SEQ ID NO: 37 and a $V_L$ comprising a sequence set forth in SEQ ID NO: 31;
(lxii) a $V_H$ comprising a sequence set forth in SEQ ID NO: 37 and a $V_L$ comprising a sequence set forth in SEQ ID NO: 32;
(lxiii) a $V_H$ comprising a sequence set forth in SEQ ID NO: 37 and a $V_L$ comprising a sequence set forth in SEQ ID NO: 33; or
(lxiv) a $V_H$ comprising a sequence set forth in SEQ ID NO: 37 and a $V_L$ comprising a sequence set forth in SEQ ID NO: 34.

Optionally, the $V_H$ is linked to a heavy chain constant region, e.g., an IgG4 heavy chain constant region. In one example, the heavy chain constant region lacks the C-terminal lysine residue.

Optionally, the $V_L$ is linked to a light chain constant region.

The IL-11Rα-binding proteins of the present disclosure may be synhumanized proteins. The term "synhumanized protein" refers to a protein prepared by a method described in WO2007/019620. A synhumanized IL-11Rα-binding protein includes a variable region of an antibody, wherein the variable region comprises FRs from a New World primate antibody variable region and CDRs from a non-New World primate antibody variable region. For example, a synhumanized IL-11Rα-binding protein includes a variable region of an antibody, wherein the variable region comprises FRs from a New World primate antibody variable region and CDRs from a mouse or rat antibody. In one example, the synhumanized IL-11Rα-binding protein is a IL-11Rα-binding antibody in which one or both of the variable regions are synhumanized. This term also encompasses a composite protein comprising, for example, one or more synhumanized variable regions and one or more, e.g., human variable regions or humanized variable regions or chimeric variable regions.

The IL-11Rα-binding proteins of the present disclosure may be primatized proteins. A "primatized protein" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898. This term also encompasses a composite protein comprising, for example, one or more primatized variable regions and one or more, e.g., human variable regions or humanized variable regions or chimeric variable regions.

In one example an IL-11Rα-binding protein of the disclosure is a chimeric protein. The term "chimeric proteins" refers to proteins in which an antigen binding domain is from a particular species (e.g., murine, such as mouse or rat) or belonging to a particular antibody class or subclass, while the remainder of the protein is from a protein derived from another species (such as, for example, human or non-human primate) or belonging to another antibody class or subclass. In one example, a chimeric protein is a chimeric antibody comprising a $V_H$ and/or a $V_L$ from a non-human antibody (e.g., a murine antibody) and the remaining regions of the antibody are from a human antibody. The production of such chimeric proteins is known in the art, and may be achieved by standard means (as described, e.g., in U.S. Pat. No. 6,331,415; U.S. Pat. No. 5,807,715; U.S. Pat. No. 4,816,567 and U.S. Pat. No. 4,816,397). This term also encompasses a composite protein comprising, for example, one or more chimeric variable regions and one or more, e.g., human variable regions or humanized variable regions or chimeric variable regions.

The present disclosure also contemplates a deimmunized IL-11Rα-binding protein, e.g., as described in WO2000/34317 and WO2004/108158. De-immunized antibodies and proteins have one or more epitopes, e.g., B cell epitopes or T cell epitopes removed (i.e., mutated) to thereby reduce the likelihood that a subject will raise an immune response against the antibody or protein. For example, an IL-11Rα-binding protein of the disclosure is analyzed to identify one or more B or T cell epitopes and one or more amino acid residues within the epitope is mutated to thereby reduce the immunogenicity of the IL-11Rα-binding protein.

It will be apparent to the skilled artisan from the foregoing disclosure that a "composite" protein comprises one form of $V_H$ (e.g., human) and another form of $V_L$ (e.g., humanized). The present disclosure explicitly encompasses all combinations of forms of $V_H$ and $V_L$.

Antibody Binding Domain Containing Proteins
Single-Domain Antibodies

In some examples, a protein of the disclosure is or comprises a single-domain antibody (which is used interchangeably with the term "domain antibody" or "dAb"). A single-domain antibody is a single polypeptide chain comprising all or a portion of the heavy chain variable region of an antibody. In certain examples, a single-domain antibody is a human single-domain antibody (Domantis, Inc., Waltham, Mass.; see, e.g., U.S. Pat. No. 6,248,516).

Diabodies, Triabodies, Tetrabodies

In some examples, a protein of the disclosure is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ or $V_H$-X-$V_L$, wherein $V_L$ is an antibody light chain variable region, $V_H$ is an antibody heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding domain, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

Single Chain Fv (scFv)

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

Alternatively, or in addition, the present disclosure encompasses a dimeric scFv, i.e., a protein comprising two scFv molecules linked by a non-covalent or covalent linkage, e.g., by a leucine zipper domain (e.g., derived from Fos or Jun). Alternatively, two scFvs are linked by a peptide linker of sufficient length to permit both scFvs to form and to bind to an antigen, e.g., as described in US20060263367.

Heavy Chain Antibodies

Heavy chain antibodies differ structurally from many other forms of antibodies, in so far as they comprise a heavy chain, but do not comprise a light chain. Accordingly, these antibodies are also referred to as "heavy chain only antibodies". Heavy chain antibodies are found in, for example, camelids and cartilaginous fish (also called IgNAR).

The variable regions present in naturally occurring heavy chain antibodies are generally referred to as "$V_{HH}$ domains" in camelid antibodies and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

A general description of heavy chain antibodies from camelids and the variable regions thereof and methods for their production and/or isolation and/or use is found inter alia in the following references WO94/04678, WO97/49805 and WO 97/49805.

A general description of heavy chain antibodies from cartilaginous fish and the variable regions thereof and methods for their production and/or isolation and/or use is found inter alia in WO2005/118629.

Other Antibodies and Proteins Comprising Antigen Binding Domains Thereof

The present disclosure also contemplates other antibodies and proteins comprising antigen-binding domains thereof, such as:

(i) "key and hole" bispecific proteins as described in U.S. Pat. No. 5,731,168;
(ii) heteroconjugate proteins, e.g., as described in U.S. Pat. No. 4,676,980;
(iii) heteroconjugate proteins produced using a chemical cross-linker, e.g., as described in U.S. Pat. No. 4,676,980; and
(iv) $Fab_3$ (e.g., as described in EP19930302894).

Mutations to Proteins

The present disclosure also provides a IL-11Rα-binding protein or a nucleic acid encoding same having at least 80% identity to a sequence disclosed herein. In one example, a IL-11Rα-binding protein or nucleic acid of the disclosure comprises sequence at least about 85% or 90% or 95% or 97% or 98% or 99% identical to a sequence disclosed herein, wherein the protein specifically binds to IL-11Rα as described herein according to any example.

Alternatively, or additionally, the IL-11Rα-binding protein comprises a CDR (e.g., three CDRs) at least about 80% or 85% or 90% or 95% or 97% or 98% or 99% identical to CDR(s) of a $V_H$ or $V_L$ as described herein according to any example, wherein the protein is capable of specifically binding to IL-11Rα as described herein according to any example. In this regard, the inventors have produced numerous antibodies having diverse sequences within their CDRs. Methods for determining binding of a protein to IL-11Rα are described herein.

For example, the inventors have identified a group of IL-11Rα-binding proteins sharing at least 40% identity in their HCDR1 (and optionally, the amino acid N-terminal to the HCDR1) according to the Kabat numbering system and another subgroup of proteins sharing 80% identity in their HCDR1.

The inventors have also identified a class of IL-11Rα-binding protein sharing 77% identity in their HCDR2 according to the Kabat numbering system and a subclass of IL-11Rα-binding proteins sharing at least about 82% identity in their HCDR2 according to the Kabat numbering system.

As discussed herein, it is also known in the art that the five C-terminal residues of heavy chain CDR2 can be mutated to conservative or non-conservative amino acid substitutions (31% of residues) (Padlan et al., FASEB J. 9: 133-139, 1995). Thus, a protein can comprise a CDR2 having at least about 47% identity to a heavy chain CDR2 sequence disclosed herein.

For example, the inventors have identified a group of IL-11Rα-binding proteins sharing at least about 44% identity in their HCDR3 according to the Kabat numbering system.

For example, the inventors have identified several residues in a $V_H$ comprising a sequence set forth in SEQ ID NO: 37 that can be substituted without loss of function or that result in improved function. In one example, the IL-11Rα-binding protein comprises between 1 and 11 amino acid substitutions compared to SEQ ID NO: 37. For example, the IL-11Rα-binding protein comprises 1 or 2 or 3 or 4 or 5 or 6 or 7 or 8 or 9 or 10 or 11 amino acid substitutions compared to SEQ ID NO: 37. For example, the IL-11Rα-binding protein comprises 3 amino acid substitutions compared to SEQ ID NO: 37. For example, the IL-11Rα-binding protein comprises 4 amino acid substitutions compared to SEQ ID NO: 37.

In one example, the IL-11Rα-binding protein comprises between 1 and 4 amino acid substitutions in CDR3 compared to SEQ ID NO: 37. For example, the IL-11Rα-binding protein comprises 1 or 2 or 3 or 4 amino acid substitutions in the CDR3 compared to SEQ ID NO: 37.

In one example, the IL-11Rα-binding protein comprises between 1 and 3 amino acid substitutions in CDR2 compared to SEQ ID NO: 37. For example, the IL-11Rα-binding protein comprises 1 or 2 or 3 amino acid substitutions in the CDR3 compared to SEQ ID NO: 37.

In one example, a IL-11Rα-binding protein of the disclosure comprises a mutant of a sequence set forth in SEQ ID NO: 37, wherein the mutant sequence at least comprises a tryptophan at position 54 of SEQ ID NO: 37.

In one example, an IL-11Rα-binding protein of the disclosure comprises a mutant of a sequence set forth in SEQ ID NO: 37, wherein the mutant sequence at least comprises a threonine at position 56 of SEQ ID NO: 37.

In one example, an IL-11Rα-binding protein of the disclosure comprises a mutant of a sequence set forth in SEQ ID NO: 37, wherein the mutant sequence at least comprises an aspartic acid at position 57 of SEQ ID NO: 37.

In one example, an IL-11Rα-binding protein of the disclosure comprises a mutant of a sequence set forth in SEQ ID NO: 37, wherein the mutant sequence at least comprises a tryptophan at position 57 of SEQ ID NO: 37.

In one example, an IL-11Rα-binding protein of the disclosure comprises a mutant of a sequence set forth in SEQ ID NO: 37, wherein the mutant sequence at least comprises a leucine at position 57 of SEQ ID NO: 37.

In one example, an IL-11Rα-binding protein of the disclosure comprises a mutant of a sequence set forth in SEQ ID NO: 37, wherein the mutant sequence at least comprises a proline at position 99 of SEQ ID NO: 37.

In one example, an IL-11Rα-binding protein of the disclosure comprises a mutant of a sequence set forth in SEQ ID NO: 37, wherein the mutant sequence at least comprises a glutamic acid at position 100 of SEQ ID NO: 37.

In one example, an IL-11Rα-binding protein of the disclosure comprises a mutant of a sequence set forth in SEQ ID NO: 37, wherein the mutant sequence at least comprises a leucine at position 100 of SEQ ID NO: 37.

In one example, an IL-11Rα-binding protein of the disclosure comprises a mutant of a sequence set forth in SEQ ID NO: 37, wherein the mutant sequence at least comprises an aspartic acid at position 101 of SEQ ID NO: 37.

In one example, an IL-11Rα-binding protein of the disclosure comprises a mutant of a sequence set forth in SEQ ID NO: 37, wherein the mutant sequence at least comprises a leucine at position 104 of SEQ ID NO: 37.

In one example, an IL-11Rα-binding protein of the disclosure comprises a mutant of a sequence set forth in SEQ ID NO: 37, wherein the mutant sequence at least comprises an arginine at position 104 of SEQ ID NO: 37.

In one example, an IL-11Rα-binding protein of the disclosure comprises a mutant of a sequence set forth in SEQ ID NO: 37, wherein the mutant sequence at least comprises a tryptophan at position 54, an aspartic acid at position 56 and a leucine at position 57 each in relation to SEQ ID NO: 37.

In one example, an IL-11Rα-binding protein of the disclosure comprises a mutant of a sequence set forth in SEQ ID NO: 37, wherein the mutant sequence at least comprises a tryptophan at position 54, an aspartic acid at position 56 and a leucine at position 57 each in relation to SEQ ID NO: 37.

In one example, an IL-11Rα-binding protein of the disclosure comprises a mutant of a sequence set forth in SEQ ID NO: 37, wherein the mutant sequence at least comprises a tryptophan at position 54, a threonine at position 56 and a leucine at position 57 each in relation to SEQ ID NO: 37.

In one example, an IL-11Rα-binding protein of the disclosure comprises a mutant of a sequence set forth in SEQ ID NO: 37, wherein the mutant sequence at least comprises a proline at position 99, a glutamic acid at position 100, an aspartic acid at position 101 and a leucine at position 104 each in relation to SEQ ID NO: 37.

In one example, an IL-11Rα-binding protein of the disclosure comprises a mutant of a sequence set forth in SEQ ID NO: 37, wherein the mutant sequence at least comprises a proline at position 99, a leucine at position 100, an aspartic acid at position 101 and an arginine at position 104 each in relation to SEQ ID NO: 37.

For example, the inventors have identified a group of IL-11Rα-binding proteins sharing at least 45% identity in their LCDR1 according to the Kabat numbering system and another subgroup of proteins sharing about 54% identity in their LCDR1.

The inventors have also identified a class of IL-11Rα-binding protein sharing at least about 55% or 56% identity in their LCDR3 according to the Kabat numbering system.

For example, the inventors have identified several residues in a $V_L$ comprising a sequence set forth in SEQ ID NO: 5 that can be substituted without loss of function or that result in improved function. In one example, the IL-11Rα-binding protein comprises between 1 and 11 amino acid substitutions compared to SEQ ID NO: 5. For example, the IL-11Rα-binding protein comprises 1 or 2 or 3 or 4 or 5 or 6 or 7 or 8 or 9 or 10 or 11 amino acid substitutions compared to SEQ ID NO: 5. For example, the IL-11Rα-binding protein comprises 3 amino acid substitutions compared to SEQ ID NO: 5. For example, the IL-11Rα-binding protein comprises 4 amino acid substitutions compared to SEQ ID NO: 5. For example, the IL-11Rα-binding protein comprises 5 amino acid substitutions compared to SEQ ID NO: 5.

In one example, the IL-11Rα-binding protein comprises between 1 and 4 amino acid substitutions in CDR3 compared to SEQ ID NO: 5. For example, the IL-11Rα-binding protein comprises 1 or 2 or 3 or 4 amino acid substitutions in the CDR3 compared to SEQ ID NO: 5.

In one example, the IL-11Rα-binding protein comprises between 1 and 5 amino acid substitutions in CDR1 compared to SEQ ID NO: 5. For example, the IL-11Rα-binding protein comprises 1 or 2 or 3 or 4 or 5 amino acid substitutions in the CDR3 compared to SEQ ID NO: 5.

In one example, a IL-11Rα-binding protein of the disclosure comprises a mutant of a sequence set forth in SEQ ID NO: 5, wherein the mutant sequence at least comprises a valine at position 29 of SEQ ID NO: 5.

In one example, a IL-11Rα-binding protein of the disclosure comprises a mutant of a sequence set forth in SEQ ID NO: 5, wherein the mutant sequence at least comprises an aspartic acid at position 30 of SEQ ID NO: 5.

In one example, a IL-11Rα-binding protein of the disclosure comprises a mutant of a sequence set forth in SEQ ID NO: 5, wherein the mutant sequence at least comprises a lysine at position 31 of SEQ ID NO: 5.

In one example, a IL-11Rα-binding protein of the disclosure comprises a mutant of a sequence set forth in SEQ ID NO: 5, wherein the mutant sequence at least comprises a valine at position 33 of SEQ ID NO: 5.

In one example, a IL-11Rα-binding protein of the disclosure comprises a mutant of a sequence set forth in SEQ ID NO: 5, wherein the mutant sequence at least comprises a glutamic acid at position 34 of SEQ ID NO: 5.

In one example, a IL-11Rα-binding protein of the disclosure comprises a mutant of a sequence set forth in SEQ ID NO: 5, wherein the mutant sequence at least comprises an alanine at position 91 of SEQ ID NO: 5.

In one example, a IL-11Rα-binding protein of the disclosure comprises a mutant of a sequence set forth in SEQ ID NO: 5, wherein the mutant sequence at least comprises a histidine at position 91 of SEQ ID NO: 5.

In one example, a IL-11Rα-binding protein of the disclosure comprises a mutant of a sequence set forth in SEQ ID NO: 5, wherein the mutant sequence at least comprises a glutamic acid at position 91 of SEQ ID NO: 5.

In one example, a IL-11Rα-binding protein of the disclosure comprises a mutant of a sequence set forth in SEQ ID NO: 5, wherein the mutant sequence at least comprises an aspartic acid at position 93 of SEQ ID NO: 5.

In one example, a IL-11Rα-binding protein of the disclosure comprises a mutant of a sequence set forth in SEQ ID NO: 5, wherein the mutant sequence at least comprises a phenylalanine at position 93 of SEQ ID NO: 5.

In one example, a IL-11Rα-binding protein of the disclosure comprises a mutant of a sequence set forth in SEQ ID NO: 5, wherein the mutant sequence at least comprises a serine at position 93 of SEQ ID NO: 5.

In one example, a IL-11Rα-binding protein of the disclosure comprises a mutant of a sequence set forth in SEQ ID NO: 5, wherein the mutant sequence at least comprises a glutamine at position 94 of SEQ ID NO: 5.

In one example, an IL-11Rα-binding protein of the disclosure comprises a mutant of a sequence set forth in SEQ ID NO: 5, wherein the mutant sequence at least comprises a valine at position 29, an aspartic acid at position 30 a lysine at position 31 a valine at position 33 and a glutamic acid at position 34 each in relation to SEQ ID NO: 5.

In one example, an IL-11Rα-binding protein of the disclosure comprises a mutant of a sequence set forth in SEQ ID NO: 5, wherein the mutant sequence at least comprises an alanine at position 91, a glutamic acid at position 92, an aspartic acid at position 93 and a glutamine at position 94 each in relation to SEQ ID NO: 5.

In one example, an IL-11Rα-binding protein of the disclosure comprises a mutant of a sequence set forth in SEQ ID NO: 5, wherein the mutant sequence at least comprises a histidine at position 91, a glutamic acid in position 92, a phenylalanine at position 93 and a glutamine at position 94 each in relation to SEQ ID NO: 5.

In one example, an IL-11Rα-binding protein of the disclosure comprises a mutant of a sequence set forth in SEQ ID NO: 5, wherein the mutant sequence at least comprises a histidine at position 91, a glutamic acid at position 92 and a glutamine at position 94 each in relation to SEQ ID NO: 5.

In one example, an IL-11Rα-binding protein of the disclosure comprises a mutant of a sequence set forth in SEQ ID NO: 5, wherein the mutant sequence at least comprises a histidine at position 91, a glutamic acid at position 92 and a glutamine at position 94 each in relation to SEQ ID NO: 5.

In one example, an IL-11Rα-binding protein of the disclosure comprises a mutant of a sequence set forth in SEQ ID NO: 5, wherein the mutant sequence at least comprises a glutamic acid at position 92, a serine at position 93 and a glutamine at position 94 each in relation to SEQ ID NO: 5.

In another example, a nucleic acid of the disclosure comprises a sequence at least about 80% or 85% or 90% or 95% or 97% or 98% or 99% identical to a sequence set forth herein and encoding an IL-11Rα-binding protein having a function as described herein according to any example. The present disclosure also encompasses nucleic acids encoding an IL-11Rα-binding protein of the disclosure, which differs from a sequence exemplified herein as a result of degeneracy of the genetic code.

The % identity of a nucleic acid or polypeptide is determined by GAP (Needleman and Wunsch. Mol. Biol. 48, 443-453, 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. For example, the two sequences are aligned over their entire length.

The present disclosure also contemplates a nucleic acid that hybridizes under stringent hybridization conditions to a nucleic acid encoding an IL-11Rα-binding protein described herein. A "moderate stringency" is defined herein as being a hybridization and/or washing carried out in 2×SSC buffer, 0.1% (w/v) SDS at a temperature in the range 45° C. to 65° C., or equivalent conditions. A "high stringency" is defined herein as being a hybridization and/or wash carried out in 0.1×SSC buffer, 0.1% (w/v) SDS, or lower salt concentration, and at a temperature of at least 65° C., or equivalent conditions. Reference herein to a particular level of stringency encompasses equivalent conditions using wash/hybridization solutions other than SSC known to those skilled in the art. For example, methods for calculating the temperature at which the strands of a double stranded nucleic acid will dissociate (also known as melting temperature, or Tm) are known in the art. A temperature that is similar to (e.g., within 5° C. or within 10° C.) or equal to the Tm of a nucleic acid is considered to be high stringency. Medium stringency is to be considered to be within 10° C. to 20° C. or 10° C. to 15° C. of the calculated Tm of the nucleic acid.

The present disclosure also contemplates mutant forms of an IL-11Rα-binding protein of the disclosure comprising one or more conservative amino acid substitutions compared to a sequence set forth herein. In some examples, the IL-11Rα-binding protein comprises 10 or fewer, e.g., 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Hydropathic indices are described, for example in Kyte and Doolittle J. Mol. Biol., 157: 105-132, 1982 and hydrophylic indices are described in, e.g., U.S. Pat. No. 4,554,101.

The present disclosure also contemplates non-conservative amino acid changes. For example, of particular interest are substitutions of charged amino acids with another charged amino acid and with neutral or positively charged amino acids. In some examples, the IL-11Rα-binding protein comprises 10 or fewer, e.g., 9 or 8 or 7 or 6 or 5 or 4 or 3 or 2 or 1 non-conservative amino acid substitutions.

In one example, the mutation(s) occur within a FR of an antigen binding domain of an IL-11Rα-binding protein of the disclosure. In another example, the mutation(s) occur within a CDR of an IL-11Rα-binding protein of the disclosure.

Exemplary methods for producing mutant forms of an IL-11Rα-binding protein include:

mutagenesis of DNA (Thie et al., Methods Mol. Biol. 525: 309-322, 2009) or RNA (Kopsidas et al., Immunol. Lett.* 107:163-168, 2006; Kopsidas et al. *BMC Biotechnology,* 7: 18, 2007; and WO1999/058661);
- introducing a nucleic acid encoding the polypeptide into a mutator cell, e.g., XL-1Red, XL-mutS and XL-mutS-Kanr bacterial cells (Stratagene);
- DNA shuffling, e.g., as disclosed in Stemmer, *Nature* 370: 389-91, 1994; and
- site directed mutagenesis, e.g., as described in Dieffenbach (ed) and Dveksler (ed) (In: PCR Primer: A Laboratory Manual, Cold Spring Harbor Laboratories, NY, 1995).

Exemplary methods for determining biological activity of the mutant IL-11Rα-binding proteins of the disclosure will be apparent to the skilled artisan and/or described herein, e.g., antigen binding. For example, methods for determining antigen binding, competitive inhibition of binding, affinity, association, dissociation and therapeutic efficacy are described herein.

Constant Regions The present disclosure encompasses IL-11Rα-binding proteins and/or antibodies described herein comprising a constant region of an antibody. This includes antigen binding fragments of an antibody fused to a Fc.

Sequences of constant regions useful for producing the proteins of the present disclosure may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In one example, the effector function is antibody-dependent cell-mediated cytotoxicity (ADCC) and/or antibody-dependent cell-mediated phagocytosis (ADCP) and/or complement-dependent cytotoxicity (CDC). Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington D.C. United States Department of Health and Human Services, 1987 and/or 1991). This position corresponds to position 228 of the hinge region according to the EU numbering system (Kabat et al., Sequences of Proteins of Immunological Interest Washington D.C. United States Department of Health and Human Services, 2001 and Edelman et al., *Proc. Natl. Acad. USA*, 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., *Eur J Immunol.* 29:2613-2624, 1999; Shields et al., *J Biol. Chem.* 276(9):6591-604, 2001). Additional examples of non-immunostimulatory Fc regions are described, for example, in Dall'Acqua et al., *J Immunol.* 177: 1129-1138 2006; and/or Hezareh *J Virol;* 75: 12161-12168, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Enhancing Effector Function

In one example, an IL-11Rα-binding protein of the present disclosure may induce effector function or enhanced effector function.

In the context of the present disclosure, "effector functions" refer to those biological activities mediated by cells or proteins that bind to the Fc region (a native sequence Fc region or amino acid sequence variant Fc region) of an antibody that result in killing of a cell. Examples of effector functions induced by antibodies include: complement dependent cytotoxicity; antibody-dependent-cell-mediated cytotoxicity (ADCC); antibody-dependent-cell-phagocytosis (ADCP); and B-cell activation.

In one example, an IL-11Rα-binding protein of the present disclosure binds to IL-11Rα on the surface of a cell in such a manner that it is capable of inducing an effector function, such as, ADCC or CDC.

For example, the IL-11Rα-binding protein remains bound to the IL-11Rα on the surface of the cell for a time sufficient to induce an effector function, such as ADCC and/or CDC.

In one example, an IL-11Rα-binding protein of the present disclosure is capable of inducing enhanced effector function, e.g., by virtue of a modified Fc region or by virtue of comprising a region capable of binding to an immune effector cell. For example, the level of effector function is increased compared to the level induced by a human IgG1 or IgG3 Fc region. Enhancing effector function induced by a IL-11Rα-binding protein of the disclosure may result in enhanced therapeutic or prophylactic effects, e.g., by not only blocking the action of IL-11Rα but also by killing or depleting cells causing a condition, e.g., by killing auto-reactive T cells.

In one example, the Fc region of an IL-11Rα-binding protein of the disclosure is modified to increase the level of effector function it is capable of inducing compared to the Fc region without the modification. Such modifications can be at the amino acid level and/or the secondary structural level and/or the tertiary structural level and/or to the glycosylation of the Fc region.

The skilled addressee will appreciate that greater effector function may be manifested in any of a number of ways, for example as a greater level of effect, a more sustained effect or a faster rate of effect.

In one example, the Fc region comprises one or more amino acid modifications that increase its ability to induce enhanced effector function. In one example, the Fc region binds with greater affinity to one or more FcγRs, such as FcγRIII. In one example, the Fc region comprise at least one amino acid substitution at a position selected from the group consisting of: 230, 233, 234, 235, 239, 240, 243, 264, 266, 272, 274, 275, 276, 278, 302, 318, 324, 325, 326, 328, 330, 332, and 335, numbered according to the EU index of Kabat. In one example, the Fc region comprises the following amino acid substitutions S239D/I332E, numbered according to the EU index of Kabat. This Fc region has about 14 fold increase in affinity for FcγRIIIa compared to a wild-type Fc region and about 3.3 increased ability to induce ADCC compared to a wild-type Fc region. In one example, the Fc region comprises the following amino acid substitutions S239D/A330L/I332E, numbered according to the EU index of Kabat. This Fc region has about 138 fold increase in affinity for FcγRIIIa compared to a wild-type Fc region and about 323 fold increased ability to induce ADCC compared to a wild-type Fc region.

Additional amino acid substitutions that increase ability of a Fc region to induce effector function are known in the art and/or described, for example, in U.S. Pat. No. 6,737,056 or U.S. Pat. No. 7,317,091.

In one example, the glycosylation of the Fc region is altered to increase its ability to induce enhanced effector function. In this regard, native antibodies produced by mammalian cells typically comprise a branched, biantennary oligosaccharide that is generally attached by an N-linkage to Asn297 of the $C_H2$ domain of the Fc region. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some examples, Fc regions according to the present disclosure comprise a carbohydrate structure that lacks fucose attached (directly or indirectly) to an Fc region, i.e., the Fc region is "afucosylated". Such variants may have an improved ability to induce ADCC. Methods for producing afucosylated antibodies include, expressing the antibody or antigen binding fragment thereof in a cell line incapable of expressing α-1,6-fucosyltransferase (FUT8) (e.g., as described in Yumane-Ohnuki et al., *Biotechnol. Bioengineer.* 87: 614-622, 2004), expressing the antibody or antigen binding fragment thereof in cells expressing a small interfering RNA against FUT8 (e.g., as described in Mori et al., *Biotechnol. Bioengineer.*, 88: 901-908, 2004), expressing the antibody or antigen binding fragment thereof in cells incapable of expressing guanosine diphosphate (GDP)-mannose 4,6-dehydratase (GMD) (e.g., as described in Kanda et al., *J. Biotechnol.*, 130: 300-310, 2007). The present disclosure also contemplates the use of proteins having a reduced level of fucosylation, e.g., produced using a cell line modified to express β-(1,4)-N-acetylglucosaminyltransferase III (GnT-III) (e.g., as described in Umãna et al., *Nat. Biotechnol.* 17: 176-180, 1999).

Other methods include the use of cell lines which inherently produce antibodies capable of inducing enhanced Fc-mediated effector function (e.g. duck embryonic derived stem cells for the production of viral vaccines, WO2008/129058; Recombinant protein production in avian EBX® cells, WO 2008/142124).

IL-11Rα-binding proteins of the present disclosure also include those with bisected oligosaccharides, e.g., in which a biantennary oligosaccharide attached to the Fc region is bisected by GlcNAc. Such proteins may have reduced fucosylation and/or improved ADCC function. Examples of such proteins are described, e.g., in U.S. Pat. No. 6,602,684 and US20050123546.

IL-11Rα-binding proteins with at least one galactose residue in the oligosaccharide attached to the Fc region are also contemplated. Such proteins may have improved CDC function. Such proteins are described, e.g., in WO1997/30087 and WO1999/22764.

IL-11Rα-binding proteins can also comprise a Fc region capable of inducing enhanced levels of CDC. For example, hybrids of IgG1 and IgG3 produce antibodies having enhanced CDC activity (Natsume et al., *Cancer Res.* 68: 3863-3872, 2008).

IL-11Rα-binding proteins can also or alternatively be fused to or conjugated to proteins (e.g., antibody variable regions) that bind to immune effector cells, e.g., by virtue of binding to CD3 or CD16.

Methods for determining effector function are known in the art. In one example, the level of ADCC activity is assessed using a $^{51}Cr$ release assay, an europium release assay or a $^{35}S$ release assay. In each of these assays, cells expressing IL-11Rα are cultured with one or more of the recited compounds for a time and under conditions sufficient for the compound to be taken up by the cell. In the case of a $^{35}S$ release assay, the cells can be cultured with $^{35}S$-labeled methionine and/or cysteine for a time sufficient for the labeled amino acids to be incorporated into newly synthesized proteins. Cells are then cultured in the presence or absence of the IL-11Rα-binding protein and in the presence of immune effector cells, e.g., PBMCs and/or NK cells. The amount of $^{51}Cr$, europium and/or $^{35}S$ in cell culture medium is then detected, and an increase in the presence of the protein compared to in the absence of protein indicates that the binding molecule/agent has effector function. Exemplary publications disclosing assays for assessing the level of ADCC induced by a protein include Hellstrom et al. *Proc. Natl Acad. Sci. USA* 83: 7059-7063, 1986 and Bruggemann et al., *J. Exp. Med.* 166: 1351-1361, 1987.

Other assays for assessing the level of ADCC induced by a protein include ACTI™ nonradioactive cytotoxicity assay for flow cytometry (CellTechnology, Inc. CA, USA) or CytoTox 96® non-radioactive cytotoxicity assay (Promega, WI, USA).

Alternatively, or additionally, effector function of an IL-11Rα-binding protein is assessed by determining its affinity for one or more FcγRs, e.g., as described in U.S. Pat. No. 7,317,091.

C1q binding assays may also be carried out to confirm that the IL-11Rα-binding protein is able to bind C1q and may induce CDC. To assess complement activation, a CDC assay may be performed (see, for example, Gazzano-Santoro et al., *J. Immunol. Methods* 202: 163, 1996).

Additional Modifications

The present disclosure also contemplates additional modifications to an antibody or IL-11Rα-binding protein comprising an Fc region or constant region.

For example, the antibody comprises one or more amino acid substitutions that increase the half-life of the protein. For example, the antibody comprises a Fc region comprising one or more amino acid substitutions that increase the affinity of the Fc region for the neonatal Fc region (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc into blood following cellular recycling. These amino acid substitutions are useful for extending the half life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

Exemplary IL-11Rα-Binding Proteins

Exemplary variable region containing IL-11Rα-binding proteins produced by the inventors are described in Table 1.

TABLE 1

Sequences of exemplary IL-11Rα-binding proteins

| | Antibody Name | $V_L$ amino acid SEQ ID NO | $V_H$ amino acid SEQ ID NO |
|---|---|---|---|
| 1 | 8E2 | 5 | 37 |
| 2 | TS-303 | 6 | 37 |
| 3 | TS-305 | 7 | 37 |
| 4 | TS-306 | 8 | 37 |
| 5 | TS-307 | 9 | 37 |
| 6 | TS-310 | 10 | 37 |
| 7 | TS-311 | 11 | 37 |
| 8 | TS-312 | 12 | 37 |
| 9 | TS-313 | 13 | 37 |
| 10 | TS-322 | 14 | 37 |
| 11 | TS-2 | 15 | 37 |
| 12 | TS-4 | 16 | 37 |
| 13 | TS-6 | 17 | 37 |
| 14 | TS-7 | 18 | 37 |
| 15 | TS-9 | 19 | 37 |
| 16 | TS-13 | 20 | 37 |
| 17 | TS-14 | 21 | 37 |
| 18 | TS-17 | 22 | 37 |
| 19 | TS-20 | 23 | 37 |
| 20 | TS-21 | 24 | 37 |
| 21 | TS-22 | 25 | 37 |
| 22 | TS-29 | 26 | 37 |
| 23 | TS-32 | 27 | 37 |
| 24 | TS-49 | 28 | 37 |
| 25 | TS-51 | 29 | 37 |
| 26 | TS-55 | 30 | 37 |
| 27 | TS-57 | 31 | 37 |
| 28 | TS-58 | 32 | 37 |
| 29 | TS-63 | 33 | 37 |
| 30 | TS-64 | 34 | 37 |
| 31 | TS-66 | 5 | 38 |
| 32 | TS-69 | 5 | 39 |
| 33 | TS-71 | 5 | 40 |
| 34 | TS-76 | 5 | 41 |
| 35 | TS-79 | 5 | 42 |
| 36 | TS-82 | 5 | 43 |
| 37 | TS-88 | 5 | 44 |
| 38 | TS-89 | 5 | 45 |
| 39 | TS-91 | 5 | 46 |
| 40 | TS-92 | 5 | 47 |
| 41 | TS-97 | 5 | 48 |
| 42 | TS-101 | 5 | 49 |
| 43 | TS-103 | 5 | 50 |
| 44 | TS-104 | 5 | 51 |
| 45 | TS-107 | 5 | 52 |
| 46 | TS-108 | 5 | 53 |
| 47 | TS-115 | 5 | 54 |
| 48 | TS-129 | 5 | 55 |
| 49 | TS-133 | 5 | 56 |
| 50 | TS-134 | 5 | 57 |
| 51 | TS-135 | 5 | 58 |
| 52 | TS-136 | 5 | 59 |
| 53 | TS-140 | 5 | 60 |
| 54 | TS-143 | 5 | 61 |
| 55 | TS-151 | 5 | 62 |
| 56 | TS-156 | 5 | 63 |
| 57 | TS-213 | 5 | 64 |
| 58 | TS-214 | 5 | 65 |
| 59 | TS-215 | 5 | 66 |
| 60 | TS-218 | 5 | 67 |
| 61 | TS-221 | 5 | 68 |
| 62 | TS-222 | 5 | 69 |
| 63 | TS-224 | 5 | 70 |
| 64 | 8E4 | 73 | 74 |
| 65 | 8D10 | 75 | 76 |

Protein Production

In one example, an IL-11Rα-binding protein described herein according to any example is produced by culturing a hybridoma under conditions sufficient to produce the protein, e.g., as described herein and/or as is known in the art.

Recombinant Expression

In another example, an IL-11Rα-binding protein described herein according to any example is recombinant.

In the case of a recombinant protein, nucleic acid encoding same can be cloned into expression constructs or vectors, which are then transfected into host cells, such as E. coli cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary cells used for expressing a protein are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or U.S. Pat. No. 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, and a transcription termination sequence. The skilled artisan will be aware of suitable sequences for expression of a protein. Exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein may be cultured in a variety of media, depending on the cell type used. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for isolating a protein are known in the art and/or described herein.

Where an IL-11Rα-binding protein is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The IL-11Rα-binding protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

The skilled artisan will also be aware that a protein can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Conjugates

In one example, an IL-11Rα-binding protein of the present disclosure is conjugated to a compound. For example, the compound is selected from the group consisting of a radioisotope, a detectable label, a therapeutic compound, a colloid, a toxin, a nucleic acid, a peptide, a protein, a compound that increases the half life of the IL-11Rα-binding protein in a subject and mixtures thereof.

The other compound can be directly or indirectly bound to the IL-11Rα-binding protein (e.g., can comprise a linker in the case of indirect binding). Examples of compounds include, a radioisotope (e.g., iodine-131, yttrium-90 or indium-111), a detectable label (e.g., a fluorophore or a fluorescent nanocrystal or quantum dot), a therapeutic compound (e.g., a chemotherapeutic or an anti-inflammatory), a colloid (e.g., gold), a toxin (e.g., ricin or tetanus toxoid), a nucleic acid, a peptide (e.g., a serum albumin binding peptide), a protein (e.g., a protein comprising an antigen binding domain of an antibody or serum albumin), a compound that increases the half life of the IL-11Rα-binding protein in a subject (e.g., polyethylene glycol or other water soluble polymer having this activity) and mixtures thereof. Exemplary compounds that can be conjugated to a IL-11Rα-binding protein of the disclosure and methods for such conjugation are known in the art and described, for example, in WO2010/059821.

The IL-11Rα-binding protein may be conjugated to nanoparticles (for example as reviewed in Kogan et al., *Nanomedicine* (Lond). 2: 287-306, 2007). The nanoparticles may be metallic nanoparticles.

The IL-11Rα-binding protein may be comprised in antibody-targeted bacterial minicells (for example as described in PCT/IB2005/000204).

Some exemplary compounds that can be conjugated to a IL-11Rα-binding protein of the present disclosure are listed in Table 2.

TABLE 2

Compounds useful in conjugation.

| Group | Detail |
|---|---|
| Radioisotopes (either directly or indirectly) | $^{123}$I, $^{125}$I, $^{130}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Gu, $^{68}$Gu, $^{67}$Cu, $^{75}$Br, $^{76}$Br, $^{77}$Br, $^{99m}$Tc, $^{11}$C, $^{13}$N, $^{15}$O, $^{18}$I, $^{188}$Rc, $^{203}$Pb, $^{64}$Cu, $^{105}$Rh, $^{198}$Au, $^{199}$Ag or $^{177}$Lu |
| Half life extenders | Polyethylene glycol Glycerol Glucose |
| Fluorescent probes | Phycoerythrin (PE) Allophycocyanin (APC) Alexa Fluor 488 Cy5.5 |
| Biologics | fluorescent proteins such as *Renilla* luciferase, GFP immune modulators or proteins, such as cytokines, e.g., an interferon toxins an immunoglobulin or antibody or antibody variable region half life extenders such as albumin or antibody variable regions or peptides that bind to albumin |
| Chemo-therapeutics | Taxol 5-FU Doxorubicin Idarubicin |

Assaying Activity of an IL-11Rα-Binding Protein Binding to IL-11Rα and Mutants Thereof It will be apparent to the skilled artisan from the disclosure herein that some IL-11Rα-binding proteins of the present disclosure bind to the extracellular region (e.g., a region as described herein) of hIL-11Rα and to specific mutant forms of extracellular region of hIL-11Rα (e.g., SEQ ID NO: 3 or SEQ ID NO: 85 without or with certain point mutations) and/or bind to both human and cynomolgus monkey IL-11Rα. Methods for assessing binding to a protein are known in the art, e.g., as described in Scopes (In: Protein purification: principles and practice, Third Edition, Springer Verlag, 1994). Such a method generally involves immobilizing the IL-11Rα-binding protein and contacting it with labeled antigen. Following washing to remove non-specific bound protein, the amount of label and, as a consequence, bound antigen is detected. Of course, the IL-11Rα-binding protein can be labeled and the antigen immobilized. Panning-type assays can also be used. Alternatively, or additionally, surface plasmon resonance assays can be used.

The assays described above can also be used to detect the level of binding of a protein to hIL-11Rα or an extracellular region thereof (e.g., as contained within SEQ ID NO: 3) or to a polypeptide of SEQ ID NO: 3 or SEQ ID NO: 85 or mutant form thereof.

In one example, an IL-11Rα-binding protein of the present disclosure binds to a polypeptide of SEQ ID NO: 95 at a level at least about 1.5 fold or 2 fold or 5 fold or 10 fold or 50 fold or 100 fold or 150 fold or 160 fold or 200 fold lower than it binds to a polypeptide of SEQ ID NO: 85.

In one example, a protein of the present disclosure binds to a polypeptide of SEQ ID NO: 96 at a level at least about 1.5 fold or 2 fold or 5 fold or 10 fold or 50 fold or 100 fold or 150 fold or 160 fold or 200 fold lower than it binds to a polypeptide of SEQ ID NO: 85.

In one example, a protein of the present disclosure binds to a polypeptide of SEQ ID NO: 86 at a level at least about 1.5 fold or 2 fold or 5 fold or 10 fold or 50 fold or 100 fold or 150 fold or 160 fold or 200 fold lower than it binds to a polypeptide of SEQ ID NO: 85.

In one example, a protein of the present disclosure binds to a polypeptide of SEQ ID NO: 89 at a level at least about 1.5 fold or 2 fold or 5 fold or 10 fold or 50 fold or 100 fold or 150 fold or 160 fold or 200 fold lower than it binds to a polypeptide of SEQ ID NO: 85.

The level of binding is conveniently determined using a biosensor.

The present disclosure contemplates any combination of the foregoing characteristics. In one example, a protein described herein has all of the binding characteristics set forth in the preceding five paragraphs.

Epitope Mapping

In another example, the epitope bound by a protein described herein is mapped. Epitope mapping methods will be apparent to the skilled artisan. For example, a series of overlapping peptides spanning the IL-11Rα sequence or a region thereof comprising an epitope of interest, e.g., peptides comprising 10-15 amino acids are produced. The IL-11Rα-binding protein is then contacted to each peptide and the peptide(s) to which it binds determined. This permits determination of peptide(s) comprising the epitope to which the protein binds. If multiple non-contiguous peptides are bound by the protein, the protein may bind a conformational epitope.

Alternatively, or in addition, amino acid residues within IL-11Rα are mutated, e.g., by alanine scanning mutagenesis or substitution of evolutionarily conserved amino acids, and mutations that reduce or prevent binding of the IL-11Rα-binding protein are determined Any mutation that reduces or prevents binding of the IL-11Rα-binding protein is likely to be within the epitope bound by the IL-11Rα-binding protein.

Another method for determining a region comprising an epitope bound by an IL-11Rα-binding protein involved substituting a region of hIL-11Rα with the corresponding region of a form of IL-11Rα to which the IL-11Rα-binding protein does not bind (e.g., mIL-11Rα). If the IL-11Rα-binding protein does not bind to the mutant form of IL-11Rα, then residues forming a part of the epitope of the protein may be within the substituted region.

A further method for determining a region comprising an epitope involves binding IL-11Rα or a region thereof to an immobilized IL-11Rα-binding protein of the present disclosure and digesting the resulting complex with proteases. Peptide that remains bound to the immobilized IL-11Rα-binding protein are then isolated and analyzed, e.g., using mass spectrometry, to determine their sequence.

A further method involves converting hydrogens in IL-11Rα or a region thereof to deutrons and binding the resulting protein to an immobilized IL-11Rα-binding protein of the present disclosure. The deutrons are then converted back to hydrogen, the IL-11Rα or region thereof isolated, digested with enzymes and analyzed, e.g., using mass spectrometry to identify those regions comprising deutrons, which would have been protected from conversion to hydrogen by the binding of an IL-11Rα-binding protein described herein.

Optionally, the dissociation constant (Kd), association constant (Ka) and/or affinity constant ($K_D$) of an immobilized IL-11Rα-binding protein for IL-11Rα or an epitope thereof is determined. The "Kd" or "Ka" or "$K_D$" for an IL-11Rα-binding protein is in one example measured by a radiolabeled or fluorescently-labeled IL-11Rα binding assay. In the case of a "Kd", this assay equilibrates the IL-11Rα-binding protein with a minimal concentration of labeled IL-11Rα in the presence of a titration series of unlabeled IL-11Rα. Following washing to remove unbound IL-11Rα, the amount of label is determined, which is indicative of the Kd of the protein.

According to another example the Kd, Ka or $K_D$ is measured by using surface plasmon resonance assays, e.g., using BIAcore surface plasmon resonance (BIAcore, Inc., Piscataway, N.J.) with immobilized IL-11Rα or a region thereof or immobilized IL-11Rα-binding protein.

In some examples, the IL-11Rα-binding protein has a similar $K_D$ or an improved $K_D$ (i.e., a $K_D$ value lower than) than antibody 8E2, because they are likely to compete for binding to IL-11Rα.

Determining Competitive Binding

Assays for determining a protein that competitively inhibits binding of antibody 8E2 and/or 8D10 and/or 8E4 will be apparent to the skilled artisan. One such method is exemplified herein.

For example, the antibody is conjugated to a detectable label, e.g., a fluorescent label or a radioactive label. The labeled antibody and the test IL-11Rα-binding protein are then mixed and contacted with IL-11Rα or a region thereof (e.g., as contained within a polypeptide comprising SEQ ID NO: 3) or a cell expressing same. The level of labeled antibody is then determined and compared to the level determined when the labeled antibody is contacted with the IL-11Rα, region or cells in the absence of the IL-11Rα-binding protein. If the level of labeled antibody is reduced in the presence of the test IL-11Rα-binding protein compared to the absence of the IL-11Rα-binding protein, the IL-11Rα-binding protein is considered to competitively inhibit binding of the antibody to IL-11Rα.

Optionally, the test IL-11Rα-binding protein is conjugated to different label to the antibody. This alternate labeling permits detection of the level of binding of the test IL-11Rα-binding protein to IL-11Rα or the region thereof or the cell.

In another example, the IL-11Rα-binding protein is permitted to bind to IL-11Rα or a region thereof (e.g., as contained within a polypeptide comprising SEQ ID NO: 3) or a cell expressing same prior to contacting the IL-11Rα, region or cell with the antibody. A reduction in the amount of bound antibody in the presence of the IL-11Rα-binding protein compared to in the absence of the IL-11Rα-binding protein indicates that the protein competitively inhibits binding of the antibody to IL-11Rα. A reciprocal assay can also be performed using labeled IL-11Rα-binding protein and first allowing the antibody to bind to IL-11Rα. In this case, a reduced amount of labeled IL-11Rα-binding protein bound to IL-11Rα in the presence of the antibody compared to in the absence of the antibody indicates that the IL-11Rα-binding protein competitively inhibits binding of the antibody to IL-11Rα.

Any of the foregoing assays can be performed with a mutant form of IL-11Rα and/or SEQ ID NO: 3 and/or SEQ ID NO: 85 and/or an extracellular region of IL-11Rα to which 8E2 and/or 8D10 and/or 8E4 binds, e.g., as described herein.

Determining Neutralization

In some examples of the present disclosure, a protein is capable of neutralizing IL-11 signaling.

Various assays are known in the art for assessing the ability of a protein to neutralize signaling of a ligand through a receptor.

In one example, the protein reduces or prevents IL-11 binding to IL-11Rα. These assays can be performed as a competitive binding assay as described herein using labeled IL-11 and/or labeled IL-11Rα-binding protein.

In a further example, the IL-11Rα-binding protein reduces proliferation of cells (e.g., BaF3 cells) expressing IL-11Rα and gp130 (e.g., cells modified to express the both proteins) which are cultured in the presence of IL-11. Cells (e.g., about $1 \times 10^4$ cell) are cultured in the presence of IL-11 (e.g., between about 0.5 ng/mL to about 5 ng/mL (such as 0.5 ng/mL or 5 ng/mL) for hIL-11 or cynoIL-11 or between about ing/mL to about 5 ng/mL (such as 1 ng/mL or 3 ng/mL or 5 ng/mL) for mIL-11) and the presence or absence of a test IL-11Rα-binding protein. Methods for assessing cell proliferation are known in the art and include, for example, MTT reduction and/or thymidine incorporation. An IL-11Rα-binding protein that reduces the level of proliferation compared to the level observed in the absence of the IL-11Rα-binding protein is considered to neutralize IL-11R signaling. By testing multiple concentrations of the IL-11Rα-binding protein an $IC_{50}$ is determined, i.e., a concentration at which 50% of the maximum inhibition of cell proliferation occurs. $IC_{50}$ of 10 μg/ml or less. In one example, the $IC_{50}$ is 9 μg/ml or less. For example, the $IC_{50}$ is 8 μg/ml or less. For example, the $IC_{50}$ is 7 μg/ml or less. For example, the $IC_{50}$ is 6 μg/ml or less. For example, the $IC_{50}$ is 5 μg/ml or less. For example, the $IC_{50}$ is 4 μg/ml or less. For example, the $IC_{50}$ is 3 μg/ml or less. In one example, relating to each of the foregoing examples, the $IC_{50}$ can be 10 pg/ml or more or 10 ng/ml or more.

A similar assay to that described in the foregoing paragraph can be performed with B9 cells or T10 cells (Dams-Kozlowska et al., *BMC Biotechnol*, 12: 8, 2012; and Yokote et al., *J AOAC*, 83: 1053-1057, 2000). In the case of an assay making use of T10 cells, proliferation can be measured by colorimetrically detecting reduction of the tetrazolium compound, 4-[3-(4-iodophenyl)-2-(4-nitrophenyl)-2H-5-tetrazolio]-1,3-benzene disulfonate (WST-1).

In a further example, the ability of the IL-11Rα-binding protein to suppress IL-11-mediated erythropoiesis is assessed. For example, Lin⁻CD34⁺ cells (e.g., from cord blood) are contacted with IL-11 in the presence or absence of the IL-11Rα-binding protein. The amount of erythropoiesis is determined by detecting the number of CD235a expressing cells, e.g., using FACS. An IL-11Rα-binding protein that reduces the number of CD235a expressing cells compared to the number in the absence of the IL-11Rα-binding protein is considered to neutralize IL-11 signaling.

In a still further example, the ability of the IL-11Rα-binding protein to suppress IL-11-mediated STAT3 phosphorylation is assessed. For example, cells expressing IL-11Rα and gp130 are cultured in the presence of IL-11 in the presence or absence of the IL-11Rα-binding protein. The level of STAT3 phosphorylation is then assessed by Western blotting or FACS using an antibody specific for phosphorylated STAT3. An exemplary assay making use of FACS is described in Dams-Kozlowska et al., *BMC Biotechnol*, 12: 8, 2012.

In another example, the ability of the IL-11Rα-binding protein to suppress IL-11-mediated proliferation of cancer cells, e.g., gastric cancer cells or acute myelogenous leukemia (AML) cells is assessed. In these assays cancer cells (e.g., AGN or MKN45 gastric cancer cells) are cultured in the presence of IL-11 in the presence or absence of the IL-11Rα-binding protein. In the case of AML cells, the cells may also be cultured in the presence of G-CSF. Proliferation of the cells is then measured using standard techniques, e.g., as discussed above and/or by assessing formation of L-CFU in the case of AML cells. Exemplary assays adaptable to the present disclosure are included in Zhang et al., *Int J Biol Sci.*, 8: 383-393, 2012 and Kimura et al., *Leukemia*, 13: 1018-1027, 1999.

Other methods for assessing neutralization of IL-11 signaling are contemplated by the present disclosure.

Determining Effector Function

As discussed herein, some IL-11Rα-binding proteins of the present disclosure have reduced effector function or have effector function (or enhanced effector function). Methods for assessing ADCC activity are known in the art.

In one example, the level of ADCC activity is assessed using a $^{51}$Cr release assay, an europium release assay or a $^{35}$S release assay. In each of these assays, cells expressing IL-11R are cultured with one or more of the recited compounds for a time and under conditions sufficient for the compound to be taken up by the cell. In the case of a $^{35}$S release assay, cells expressing IL-11Rα can be cultured with $^{35}$S-labeled methionine and/or cysteine for a time sufficient for the labeled amino acids to be incorporated into newly synthesized proteins. Cells are then cultured in the presence or absence of the IL-11Rα-binding protein and in the presence of immune effector cells, e.g., peripheral blood mononuclear cells (PBMC) and/or NK cells. The amount of $^{51}$Cr, europium and/or $^{35}$S in cell culture medium is then detected, and little or no change in the presence of the IL-11Rα-binding protein compared to in the absence of IL-11Rα-binding protein indicates that the protein has reduced effector function and an increased amount compared to in the absence of the IL-11Rα-binding protein (or increased compared to in the presence of IL-11Rα-binding protein comprising an IgG1 Fc region) indicating effector function or enhanced effector function. Exemplary publications disclosing assays for assessing the level of ADCC induced by a protein include Hellstrom, et al. *Proc. Natl. Acad. Sci. USA* 83:7059-7063, 1986 and Bruggemann, et al., *J. Exp. Med.* 166:1351-1361, 1987.

Other assays for assessing the level of ADCC induced by a protein include ACTI™ nonradioactive cytotoxicity assay for flow cytometry (CellTechnology, Inc. CA, USA) or CytoTox 96® non-radioactive cytotoxicity assay (Promega, WI, USA).

C1q binding assays may also be carried out to confirm that the IL-11Rα-binding protein is able to bind C1q and may induce CDC. To assess complement activation, a CDC assay may be performed (see, for example, Gazzano-Santoro et al, *J. Immunol. Methods* 202: 163, 1996).

Determining Half Life

Some IL-11Rα-binding proteins encompassed by the present disclosure have an improved half-life, e.g., are modified to extend their half-life compared to IL-11Rα-binding proteins that are unmodified. Methods for determining an IL-11Rα-binding protein with an improved half-life will be apparent to the skilled person. For example, the ability of an IL-11Rα-binding protein to bind to a neonatal Fc receptor (FcRn) is assessed. In this regard, increased binding affinity for FcRn increases the serum half-life of the IL-11Rα-binding protein (see for example, Kim et al., *Eur J. Immunol.*, 24:2429, 1994).

The half-life of an IL-11Rα-binding protein of the disclosure can also be measured by pharmacokinetic studies, e.g., according to the method described by Kim et al, *Eur J of Immunol* 24:542, 1994. According to this method radiolabeled IL-11Rα-binding protein is injected intravenously into mice and its plasma concentration is periodically measured as a function of time, for example at 3 minutes to 72 hours after the injection. The clearance curve thus obtained should be biphasic, that is, an alpha phase and beta phase. For the determination of the in vivo half-life of the protein, the clearance rate in beta-phase is calculated and compared with that of the wild type or unmodified protein.

Assessing Therapeutic Efficacy

Assays for assessing therapeutic efficacy are described hereinabove in relation to determining neutralization by an IL-11Rα-binding protein.

In another example, the efficacy of a protein to treat a condition is assessed using an in vivo assay.

For example, the IL-11Rα-binding protein is tested in an animal model of arthritis. Exemplary models include a SKG strain of mouse (Sakaguchi et al., Nature, 426: 454-460), rat type II collagen arthritis model, mouse type II collagen arthritis model or antigen induced arthritis models in several species (Bendele *J Musculoskel Neuron Interact;* 1(4):377-385, 2001). In these assays, arthritis is induced and the ability of the IL-11Rα-binding protein to reduce one or more symptoms of arthritis, e.g., joint inflammation and/or markers of inflammation in synovial fluid is assessed. An IL-11Rα-binding protein that reduces a symptom of arthritis is considered useful for treating this condition or an IL-11-mediated condition (e.g., an IL-11-mediated inflammatory condition).

The IL-11Rα-binding protein can also or alternatively be tested in a model of COPD, e.g., in which a non-human mammal (e.g., a rodent, such as, a mouse) is exposed to cigarette smoke. Following exposure, the mammal is administered an IL-11Rα-binding protein and the level of lung inflammation and/or the number of neutrophils in the lung is assessed or estimated using standard techniques. An IL-11Rα-binding protein that reduces lung inflammation and/or the number of neutrophils is considered useful for treating lung inflammation or COPD or an IL-11-mediated condition (e.g., an IL-11-mediated inflammatory condition, such as an IL-11-mediated inflammatory lung condition).

The IL-11Rα-binding protein can also or alternatively be tested in a Th2-inflammatory condition, such as asthma or airway hyperreactivity. An exemplary model of allergic asthma is the mouse OVA-model, e.g., as described in Wang et al, *J. Immunol.* 165: 2222, 2000. Following induction of inflammation, an IL-11Rα-binding protein is administered to the mice and symptoms of asthma, such as numbers of eosinophils in bronchoalveolar lavage fluid (BAL), mucus secretion and/or goblet cell hyperplasia are assessed. Other models of asthma are known in the art and include an ovine model of inflammatory asthma as described in WO2002/098216, a mouse model of allergic asthma, e.g., induced by host dust mite protein (Fattouh et al., *Am J Respir Crit. Care Med* 172: 314-321, 2005), a mouse model of severe asthma in which IL-5 and eotaxin are overexpressed, or mice receiving intratracheal instillation of poly-1-lysine which are hypersensitive to methacholine when delivered as an aerosol (Homma et al., *Am J Physiol Lung Cell Mol Physiol* 289: L413-L418, 2005).

The IL-11Rα-binding protein can additionally or alternatively be tested in a model of cancer, e.g., gastric cancer. For example, mice homologous for the Y757F mutant of gp130 (gp130$^{Y757F/Y757F}$) develop gastric tumors Jenkins et al, *Blood* 109: 2380-2388, 2007). Mice (e.g., eight week old mice) are treated with an IL-11Rα-binding protein and the number and/or weight of gastric polyps assessed. An IL-11Rα-binding protein that reduces polyp size and/or weight is considered useful for treating cancer. A similar assay can be used to test for an effect on colon cancer, in which gp130$^{Y757F/Y757F}$ mice are treated with azoxymethane (AOM) followed by dextran sodium sulfate (DSS) essentially as described in Greten (et al, *Cell,* 118: 285-296, 2004) to induce colon cancer prior to treatment with the IL-11Rα-binding protein.

The IL-11Rα-binding protein can additionally or alternatively be tested in a model of cancer metastasis or cancer-related bone disease, e.g., as described in Li et al., *Oncol. Lett.* 3: 802-806, 2012.

Conditions to be Treated

The present disclosure contemplates treatment or prevention of any condition that is caused by or exacerbated by IL-11 in a subject.

In one example, the condition is an autoimmune or inflammatory condition.

In one example, the autoimmune condition is an autoimmune joint condition, such as, inflammatory arthritis, rheumatoid arthritis or idiopathic arthritis, e.g., juvenile idiopathic arthritis. In one example, the condition is rheumatoid arthritis.

In one example, the autoimmune condition is an autoimmune bowel condition, such as inflammatory bowel disease, such as ulcerative colitis or Crohn's disease.

In one example, the autoimmune condition is an autoimmune skin condition, such as psoriasis.

In one example, the inflammatory condition is an inflammatory lung condition, such as, a pulmonary disease associated with neutrophil infiltration. For example, the condition is asthma, chronic obstructive pulmonary disease (COPD), rhinitis or allergy. In one example, the condition is asthma.

Other exemplary inflammatory conditions include infection-induced inflammation (e.g., inflammation induced by *M. tuberculosis*), gastric inflammation (e.g., associated with gastric cancer), or inflammatory dermatis (e.g., atopic dermatitis).

In one example, the condition is a wasting condition, such as cachexia or sarcopenia. In one example, wasting condition is cachexia. For example, the cachexia is associated with or caused by a condition selected from rheumatoid arthritis, diabetes, cardiac disease, chronic kidney disease, chronic pulmonary inflammation, intestinal inflammation, inflammatory bowel disease, age, sepsis or AIDS. In one example, the cachexia is associated with or caused by cancer.

In one example, the condition is a bone condition, e.g., caused by insufficient bone formation and/or excessive bone catabolism. Exemplary bone conditions include osteoporosis (including post-menopausal osteoporosis), bone fracture, bone resorption/damage caused by cancer (e.g., metastastic bone cancer, myeloma or Paget's disease of bone) and bone resorption/damage caused by treatment of cancer (e.g., chemotherapy, hormone ablation or hormone inhibition).

In one example, the condition is cancer. Exemplary cancers include hematologic cancers, cancers of epithelial origin, gastric cancer, pancreatic cancer, liver cancer, osteosarcoma, endometrial cancer or ovarian cancer.

In one example, the subject is resistant to, does not adequately respond to, or is unsuitable for treatment with another compound used to treat the condition. For example, the subject suffering from an autoimmune or inflammatory condition is resistant to, does not adequately respond to, or is unsuitable for treatment with a corticosteroid and/or an immunosuppressant and/or cyclophosphamide and/or methotrexate and/or an anti-TNF antibody or soluble TNF receptor and/or an anti-CD20 antibody and/or an anti-IL6 antibody and/or an anti-CD22 antibody.

Compositions

In some examples, an IL-11Rα-binding protein as described herein can be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term "parenteral" as used herein includes subcutaneous, intravenous, intramuscular, intraperitoneal, intrathecal, intraventricular, intrasternal, and intracranial injection or infusion techniques.

Methods for preparing an IL-11Rα-binding protein into a suitable form for administration to a subject (e.g. a pharmaceutical composition) are known in the art and include, for example, methods as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

The pharmaceutical compositions of this disclosure are particularly useful for parenteral administration, such as intravenous administration or administration into a body cavity or lumen of an organ or joint. The compositions for administration will commonly comprise a solution of an IL-11Rα-binding protein dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of an IL-11Rα-binding proteins of the present disclosure in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

Upon formulation, an IL-11Rα-binding proteins of the present disclosure will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver an IL-11Rα-binding protein of the present disclosure.

WO2002/080967 describes compositions and methods for administering aerosolized compositions comprising antibodies for the treatment of, e.g., asthma, which are also suitable for administration of an IL-11Rα-binding protein of the present disclosure.

Combination Therapies

In one example, an IL-11Rα-binding protein of the present disclosure is administered in combination with another compound useful for treating a condition described herein, either as combined or additional treatment steps or as additional components of a therapeutic formulation.

For example, the other compound is an anti-inflammatory compound. Alternatively, or additionally, the other compound is an immunosuppressant. Alternatively, or additionally, the other compound is a corticosteroid, such as prednisone and/or prednisolone. Alternatively, or additionally, the other compound is methotrexate. Alternatively, or additionally, the other compound is cyclophosphamide. Alternatively, or additionally, the other compound is mycophenolate mofetil. Alternatively, or additionally, the other compound is an anti-CD20 antibody (e.g., rituximab or ofatumumab). Alternatively, or additionally, the other compound is an anti-CD22 antibody (e.g., epratuzumab). Alternatively, or additionally, the other compound is an anti-TNF antibody (e.g., infliximab or adalimumab or golimumab) or soluble TNF receptor (e.g., etanercept). Alternatively, or additionally, the other compound is a CTLA-4 antagonist (e.g., abatacept, CTLA4-Ig). Alternatively, or additionally, the other compound is an anti-IL-6 antibody. Alternatively, or additionally, the other compound is a BLys antagonist, such as an anti-BLys antibody (e.g., belimumab).

In another example, the other compound is a chemotherapy drug or other drug used for treating cancer.

In another example, the protein described herein is administered before or after radiotherapy for the treatment of cancer.

Dosages and Timing of Administration

Suitable dosages of an IL-11Rα-binding proteins of the present disclosure will vary depending on the specific an IL-11Rα-binding protein, the condition to be treated and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment/prophylaxis, data from the cell culture assays or animal studies are used, wherein a suitable dose is within a range of circulating concentrations that include the $ED_{50}$ of the active compound with little or no toxicity. The dosage may vary within this range depending upon the dosage form employed and the route of administration utilized. A therapeutically/prophylactically effective dose can be estimated initially from cell culture assays. A dose may be formulated in animal models to achieve a circulating plasma concentration range that includes the $IC_{50}$ (i.e., the concentration or amount of the compound which achieves a half-maximal inhibition of symptoms) as determined in cell culture. Such information can be used to more accurately determine useful doses in humans. Levels in plasma maybe measured, for example, by high performance liquid chromatography.

In some examples, a method of the present disclosure comprises administering a prophylactically or therapeutically effective amount of a protein described herein.

The term "therapeutically effective amount" is the quantity which, when administered to a subject in need of treatment, improves the prognosis and/or state of the subject and/or that reduces or inhibits one or more symptoms of a clinical condition described herein to a level that is below that observed and accepted as clinically diagnostic or clinically characteristic of that condition. The amount to be administered to a subject will depend on the particular characteristics of the condition to be treated, the type and stage of condition being treated, the mode of administration, and the characteristics of the subject, such as general health, other diseases, age, sex, genotype, and body weight. A person skilled in the art will be able to determine appropriate dosages depending on these and other factors. Accordingly, this term is not to be construed to limit the present disclosure to a specific quantity, e.g., weight or amount of protein(s), rather the present disclosure encompasses any amount of the IL-11Rα-binding protein(s) sufficient to achieve the stated result in a subject.

As used herein, the term "prophylactically effective amount" shall be taken to mean a sufficient quantity of a protein to prevent or inhibit or delay the onset of one or more detectable symptoms of a clinical condition. The skilled artisan will be aware that such an amount will vary depending on, for example, the specific IL-11Rα-binding protein(s) administered and/or the particular subject and/or the type or severity or level of condition and/or predisposition (genetic or otherwise) to the condition. Accordingly, this term is not to be construed to limit the present disclosure to a specific quantity, e.g., weight or amount of IL-11Rα-binding protein(s), rather the present disclosure encompasses any amount of the IL-11Rα-binding protein(s) sufficient to achieve the stated result in a subject.

For in vivo administration of the IL-11Rα-binding protein described herein, normal dosage amounts may vary from about 10 ng/kg up to about 100 mg/kg of an individual's body weight or more per day. For repeated administrations over several days or longer, depending on the severity of the disease or disorder to be treated, the treatment can be sustained until a desired suppression of symptoms is achieved.

In some examples, the IL-11Rα-binding protein is administered at an initial (or loading) dose of between about 1 mg/kg to about 30 mg/kg, such as from about 1 mg/kg to about 10 mg/kg, or about 1 mg/kg or about 2 mg/kg or 5 mg/kg. The IL-11Rα-binding protein can then be administered at a lower maintenance dose of between about 0.01 mg/kg to about 2 mg/kg, such as from about 0.05 mg/kg to about 1 mg/kg, for example, from about 0.1 mg/kg to about 1 mg/kg, such as about 0.1 mg/kg or 0.5 mg/kg or 1 mg/kg. The maintenance doses may be administered every 7-30 days, such as, every 10-15 days, for example, every 10 or 11 or 12 or 13 or 14 or 15 days.

In some examples, the IL-11Rα-binding protein is administered at a dose of between about 0.01 mg/kg to about 50 mg/kg, such as between about 0.05 mg/kg to about 30 mg/kg, for example, between about 0.1 mg/kg to about 20 mg/kg, for example, between about 0.1 mg/kg to about 10 mg/kg, such as between about 0.1 mg/kg to about 2 mg/kg. For example, the IL-11Rα-binding protein is administered at a dose of between about 0.01 mg/kg to about 5 mg/kg, such as from about 0.1 mg/kg to about 2 mg/kg, such as about 0.2 mg/kg or 0.3 mg/kg or 0.5 mg/kg or 1 mg/kg or 1.5 mg/kg (e.g., without a higher loading dose or a lower maintenance dose). In some examples, numerous doses are administered, e.g., every 7-30 days, such as, every 10-22 days, for example, every 10-15 days, for example, every 10 or 11 or 12 or 13 or 14 or 15 or 16 or 17 or 18 or 19 or 20 or 21 or 22 days. For example, the IL-11Rα-binding protein is administered every 7 days or every 14 days or every 21 days.

In some examples, at the time of commencing therapy, the mammal is administered the IL-11Rα-binding protein on no more than 7 consecutive days or 6 consecutive days or 5 consecutive days or 4 consecutive days.

In the case of a mammal that is not adequately responding to treatment, multiple doses in a week may be administered. Alternatively, or in addition, increasing doses may be administered.

In another example, for mammals experiencing an adverse reaction, the initial (or loading) dose may be split over numerous days in one week or over numerous consecutive days.

Administration of an IL-11Rα-binding protein according to the methods of the present disclosure can be continuous or intermittent, depending, for example, on the recipient's physiological condition, whether the purpose of the administration is therapeutic or prophylactic, and other factors known to skilled practitioners. The administration of an IL-11Rα-binding protein may be essentially continuous over a preselected period of time or may be in a series of spaced doses, e.g., either during or after development of a condition.

IL-11Rα Detection Assays

The following assays can be performed with an IL-11Rα-binding protein of the disclosure, e.g., an IL-11Rα-binding protein conjugated to a detectable label as discussed herein. Detection of IL-11Rα or cells expressing same with an assay described herein is useful for diagnosing or prognosing a condition.

An immunoassay is an exemplary assay format for diagnosing a condition in a subject or detecting IL-11Rα and cells expressing same in a sample. The present disclosure contemplates any form of immunoassay, including Western blotting, enzyme-linked immunosorbent assay (ELISA), fluorescence-linked immunosorbent assay (FLISA), competition assay, radioimmunoassay, lateral flow immunoassay, flow-through immunoassay, electrochemiluminescent assay, nephelometric-based assays, turbidometric-based assay, and fluorescence activated cell sorting (FACS)-based assays.

One form of a suitable immunoassay is, for example, an ELISA or FLISA.

In one form such an assay involves immobilizing an IL-11Rα-binding protein of the disclosure onto a solid matrix, such as, for example a polystyrene or polycarbonate microwell or dipstick, a membrane, or a glass support (e.g. a glass slide). A test sample is then brought into direct contact with the IL-11Rα-binding protein and IL-11Rα or cells expressing same in the sample is bound or captured. Following washing to remove any unbound protein in the sample, an IL-11Rα-binding protein that binds to IL-11Rα at a distinct epitope or binds to a different antigen on a cell is brought into direct contact with the captured IL-11Rα or cell. This detector protein is generally labeled with a detectable reporter molecule, such as for example, an enzyme (e.g. horseradish peroxidase (HRP), alkaline phosphatase (AP) or β-galactosidase) in the case of an ELISA or a fluorophore in the case of a FLISA. Alternatively, a second labeled protein can be used that binds to the detector protein. Following washing to remove any unbound protein the detectable reporter molecule is detected by the addition of a substrate in the case of an ELISA, such as for example hydrogen peroxide, TMB, or toluidine, or 5-bromo-4-chloro-3-indol-beta-D-galactopyranoside (x-gal). Of course, the immobilized (capture) protein and the detector protein may be used in the opposite manner.

The level of the antigen in the sample is then determined using a standard curve that has been produced using known quantities of the marker or by comparison to a control sample.

The assays described above are readily modified to use chemiluminescence or electrochemiluminescence as the basis for detection.

As will be apparent to the skilled artisan, other detection methods based on an immunosorbent assay are useful in the performance of the present disclosure. For example, an immunosorbent method based on the description supra using a radiolabel for detection, or a gold label (e.g. colloidal gold) for detection, or a liposome, for example, encapsulating NAD+ for detection or an acridinium linked immunosorbent assay.

In some examples of the disclosure, the level of IL-11Rα or cell expressing same is determined using a surface plasmon resonance detector (e.g., BIAcore™, GE Healthcare, Piscataway, N.J.), a flow through device, for example, as described in U.S. Pat. No. 7,205,159; a micro- or nano-immunoassay device (e.g., as described in US20030124619); a lateral flow devices (e.g., as described in US20040228761 or US20040265926); a fluorescence polarization immunoassay (FPIA e.g., as described in U.S. Pat. No. 4,593,089 or U.S. Pat. No. 4,751,190); or an immunoturbidimetric assay (e.g., as described in U.S. Pat. No. 5,571,728 or U.S. Pat. No. 6,248,597).

Samples and Control Samples

As will be apparent to the skilled artisan, some of the examples described herein require some degree of quantification to determine the level of IL-11Rα or cell expressing same. Such quantification may be determined by the inclusion of a suitable control sample in an assay of the disclosure.

In one example, a suitable control sample is a sample that is derived from a healthy subject or a normal subject.

In the present context, the term "healthy subject" shall be taken to mean an individual who is known not to suffer from a condition associated with IL-11Rα, e.g., an inflammatory condition.

The term "normal subject" shall be taken to mean an individual having a normal level of IL-11Rα or cell expressing same in a sample compared to a population of individuals.

The present disclosure also contemplates the control sample as being a data set obtained from a normal and/or healthy subject or a population of normal and/or healthy subjects.

In one example, a method of the disclosure additionally comprises determining the level of IL-11Rα in a control sample, e.g., using a method described herein.

In one example, a sample from the subject and a control sample are assayed at approximately or substantially the same time.

In one example, the sample from the subject and the control sample are assayed using the same method of the disclosure as described herein in any one or more examples to allow for comparison of results.

Kits

The present disclosure additionally comprises a kit comprising one or more of the following:

(i) an IL-11Rα-binding protein of the disclosure or expression construct(s) encoding same;
(ii) a cell of the disclosure; or
(iii) a pharmaceutical composition of the disclosure.

In the case of a kit for detecting IL-11Rα, the kit can additionally comprise a detection means, e.g., linked to a IL-11Rα-binding protein of the disclosure.

In the case of a kit for therapeutic/prophylactic use, the kit can additionally comprise a pharmaceutically acceptable carrier.

Optionally a kit of the disclosure is packaged with instructions for use in a method described herein according to any example.

The present disclosure includes the following non-limiting Examples.

NON-LIMITING EXAMPLES

Materials and Methods

Phage Display

Human IL-11Rα specific antibodies were isolated from a human Fab-phagemid antibody library. Phage that bound to immobilized hIL-11Rα-Fc (R&D Systems Cat. No. 1977-MR) were eluted in the presence of either wildtype hIL-11 or a hIL-11 mutein. A number of positive clones (as confirmed by phagemid ELISA) were reformatted to human IgG4 antibodies.

IL-11 Responsive Cell Proliferation Assay hIL-11, cynoIL-11 and mIL-11 responsive BaF3 cell lines were used to test the ability of antibodies to block IL-11 bioactivity. The mIL-11 responsive BaF3 cell line is described in WO2009/052588.

hIL-11 and cynoIL-11 responsive BaF3 cell lines were stably transfected with constructs encoding wild-type human and cynoIL-11Rα, respectively, and human gp130 and cynomolgus monkey gp130, respectively. Cells were selected by growth in media containing hIL-11 or cynoIL-11 and clonal cell lines were derived by limit dilution cloning. A number of stably transfected clones were analyzed for their dose-responsive proliferation (using a thymidine incorporation assay) when cultured in the presence of hIL-11 or cyno IL-11. One hIL-11 responsive clone and one cynoIL-11 responsive clone were each selected for analysis of antibodies.

IL-11 responsive BaF3 cells were seeded at about $1 \times 10^4$ cells/well in 96 well plates in RPMI/10% FCS in the presence of a submaximal concentration of IL-11 (hIL-11: 0.5 ng/mL or 5 ng/mL; mIL-11: 1 ng/mL, 3 ng/mL or 5 ng/mL; cyno IL-11: 0.5 ng/mL or 5 ng/mL) and increasing concentrations of purified monoclonal antibodies in a total volume of 100 μL/well. Cells were cultured for 48 hours at 37° C. and pulsed with $^3$H-thymidine for the last 6 hours of culture. Cells were harvested onto glass fibre filters and the level of radioactive thymidine incorporated into DNA determined by liquid scintillation counting. Assays were performed in duplicate and mean values for each assay point were then plotted.

Affinity Maturation of Antibody 8E2

Antibody 8E2 was affinity matured using the following method. The sequences encoding the $V_H$ and $V_L$ of 8E2 were inserted into a phagemid construct to encode a germlined Fab and germline stop templates were created by replacing 18 codons (6 amino acid residues) in all CDRs, except CDR-L2, with TAA stop codons. Libraries were constructed using methods essentially as described by Sidhu et al. (*Methods in Enzymology:* 238: 333-336, 2000). Each stop template was used as template for the Kunkel mutagenesis method (Kunkel et al., *Methods in Enzymology:* 154: 367-382, 1987) with mutagenic oligonucleotides designed to simultaneously repair the stop codons and introduce mutations at the designed sites. The mutagenesis reactions were introduced into *E. coli* by electroporation, and phage production was initiated with addition of helper phage. After overnight growth at 30° C., the phage were harvested by precipitation with PEG/NaCl.

Libraries were cycled through several rounds of selection with decreasing concentration of biotinylated polypeptide comprising SEQ ID NO: 3. The target concentration was reduced 10-fold with each round.

Antibody Binding to Domain-Swapped IL-11R Mutant Polypeptides

Various soluble forms of IL-11R comprising regions of hIL-11R and mIL-11R were produced and comprise sequences as set forth in SEQ ID NOs: 3 and 86-90 and the binding of antibodies 8E2, 8D10 and 8E4 to those polypeptides was determined using Western blotting or Biacore analysis.

For Biacore analysis, anti-human was IgG immobilized on the sensor surface at ~10,000-12,000 RU and each antibody was captured at between 0.2 μg/ml and 0.5 μg/ml every cycle for 120 seconds. IL-11 receptors were injected over captured antibodies at varying concentrations, ranging from 1 μM down to 2.5 nM, including injections of buffer blanks. Association was monitored for 3-5 minutes, dissociation was monitored for 3-10 minutes. Approximate affinities were determined by fitting binding curves of each interaction to a 1:1 Kinetic Model.

Antibody Binding to Point Mutants of Soluble hIL-11R

Various point mutants of soluble forms of IL-11R were produced in which amino acids from mIL-11 were introduced into a soluble form of hIL-11 (SEQ ID NO: 85) (see Table 5 for positions of mutations relative to SEQ ID NO: 1 and for reference to the SEQ ID NO: of each polypeptide) and the binding of antibodies to those polypeptides or to polypeptides of SEQ ID NO: 3 or SEQ ID NO: 85 was determined using Biacore analysis or FACS.

Anti human IgG Fc specific antibody was chemically immobilized on a CM5 chip to ~9000 RU. Antibodies were captured at about 0.3-1 ng/ml for 120 seconds on 2 spots in each flow cell. Adjacent spots consisting of only anti human IgG were used as a reference. IL-11 receptors were injected over the captured antibodies and reference spots at 40, 10, 5 and 2.5 nM in duplicate. Blank injections of buffer only were also performed in duplicate. Injection was performed for 3 minutes and dissociation monitored for a further 5 minutes.

Binding curves were reference subtracted and buffer blanked before fitting to a 1:1 kinetic model.

Example 1

Antibody Isolation and Characterization

Three antibodies, 8E2, 8D10 and 8E4, were isolated from a Fab-phagemid antibody library based on their ability to inhibit hIL-11 dependent transfected BaF3 cell proliferation. 8E4 also inhibited mouse IL-11 dependent BaF3 cell proliferation.

8E2, 8D10 and 8E4 bound to cells transfected with hIL-11Rα or cynoIL-11Rα. 8E4, but not 8E2 and 8D10, bound to cells transfected with mIL-11Rα.

Of the three antibodies, 8E2 had the best thermal stability as assessed by differential scanning calorimetry (with a Tm of between 69.8° C. and 76.6° C. compared to between 63.2° C. and 71.4° C. for 8D10 and 8E4).

8E2 was selected and affinity matured. Heavy and light chain libraries were used to generate clones with mutated CDRs (FIGS. 1, 2 and 3). Binding of 62 of these affinity variants to hIL-11R was assessed by Biacore and relative ability to inhibit hIL-11 induced proliferation of BaF3 cells was determined. Results are shown in Table 3.

TABLE 3

Characteristics of affinity matured antibodies

| mAb[1] | IC$_{50}$ (μg/ml)[2] | KD (M)[3] | Fold increase in potency relative to 8E2 |
|---|---|---|---|
| hu8E2-TS-82 | 0.26 | 2.05E−09 | 4.3 |
| hu8E2-TS-79 | 0.21 | 2.13E−09 | 5.3 |
| hu8E2-TS-88 | 0.36 | 2.25E−09 | 3.0 |
| hu8E2-TS-71 | 0.29 | 2.49E−09 | 3.8 |
| hu8E2-TS-76 | 0.32 | 2.73E−09 | 3.4 |
| hu8E2-TS-92 | 0.18 | 3.20E−09 | 2.3 |
| hu8E2-TS-69 | 1.46 | 3.56E−09 | 0.9 |
| hu8E2-TS-89 | 0.12 | 4.50E−09 | 1.4 |
| hu8E2-TS-91 | 0.34 | 4.73E−09 | 1.3 |
| hu8E2-TS-66 | 2.84 | 7.46E−09 | 0.5 |
| hu8E2-TS-115 | 0.26 | 7.35E−10 | 5.7 |
| hu8E2-TS-101 | 0.19 | 7.85E−10 | 2.1 |
| hu8E2-TS-104 | 0.28 | 9.95E−10 | 5.2 |
| hu8E2-TS-97 | 0.26 | 1.22E−09 | 1.6 |
| hu8E2-TS-107 | 0.20 | 1.29E−09 | 7.4 |
| hu8E2-TS-108 | 0.12 | 1.93E−09 | 12.7 |
| hu8E2-TS-151 | 0.26 | 2.42E−10 | 2.4 |
| hu8E2-TS-136 | 0.16 | 2.32E−10 | 6.0 |
| hu8E2-TS-143 | 0.39 | 4.16E−10 | 1.6 |
| hu8E2-TS-140 | 0.42 | 4.71E−10 | 1.5 |
| hu8E2-TS-133 | 0.23 | 5.13E−10 | 4.1 |
| hu8E2-TS-134 | 0.22 | 5.20E−10 | 4.3 |
| hu8E2-TS-135 | 0.20 | 5.25E−10 | 4.8 |
| hu8E2-TS-129 | 0.20 | 6.30E−10 | 4.7 |

TABLE 3-continued

Characteristics of affinity matured antibodies

| mAb[1] | IC$_{50}$ (μg/ml)[2] | KD (M)[3] | Fold increase in potency relative to 8E2 |
|---|---|---|---|
| hu8E2-TS-156 | 0.13 | 6.31E-10 | 4.9 |
| hu8E2-TS-221 | 0.20 | 6.34E-10 | 2.6 |
| hu8E2-TS-214 | 0.31 | 1.11E-09 | 1.6 |
| hu8E2-TS-218 | 0.19 | 1.39E-09 | 2.7 |
| hu8E2-TS-215 | 0.34 | 1.85E-09 | 1.5 |
| hu8E2-TS-224 | 0.39 | 1.91E-09 | 1.2 |
| hu8E2-TS-222 | 0.16 | 1.91E-09 | 3.3 |
| hu8E2-TS-213* | 0.51 | >0.00000000900 | 1.2 |
| hu8E2-TS-306 | 0.15 | 1.07E-09 | 3.3 |
| hu8E2-TS-307 | 0.25 | 1.32E-09 | 1.9 |
| hu8E2-TS-305 | 0.23 | 1.58E-09 | 2.1 |
| hu8E2-TS-311 | 0.60 | 1.69E-09 | 0.6 |
| hu8E2-TS-312 | 0.29 | 1.76E-09 | 1.2 |
| hu8E2-TS-310 | 0.84 | 2.09E-09 | 0.4 |
| hu8E2-TS-303 | 0.35 | 4.09E-09 | 1.4 |
| hu8E2-TS-313 | 0.51 | 5.56E-09 | 0.7 |
| hu8E2-TS-322 | 0.33 | 6.01E-09 | 1.1 |
| hu8E2-TS-7 | 0.63 | 1.08E-10 | 3.3 |
| hu8E2-TS-20 | 1.30 | 2.84E-10 | 0.6 |
| hu8E2-TS-6 | 0.41 | 2.89E-10 | 1.4 |
| hu8E2-TS-4 | 0.31 | 2.95E-10 | 6.6 |
| hu8E2-TS-14 | 0.52 | 3.42E-10 | 1.6 |
| hu8E2-TS-21 | 0.31 | 2.30E-10 | 2.7 |
| hu8E2-TS-17 | 0.35 | 3.90E-10 | 2.3 |
| hu8E2-TS-103 | 0.33 | 4.97E-10 | 4.5 |
| hu8E2-TS-22 | 0.40 | 8.38E-10 | 2.0 |
| hu8E2-TS-2 | 0.26 | 5.29E-10 | 7.9 |
| hu8E2-TS-29 | 0.33 | 1.06E-09 | 2.5 |
| hu8E2-TS-9 | 0.68 | 2.29E-09 | 3.1 |
| hu8E2-TS-32 | 0.41 | 9.56E-09 | 2.4 |
| hu8E2-TS-13 | NP | | NP |
| hu8E2-TS-51 | 0.28 | 4.55E-10 | 3.6 |
| hu8E2-TS-55 | 0.21 | 4.83E-10 | 4.8 |
| hu8E2-TS-64 | 0.26 | 6.36E-10 | 5.4 |
| hu8E2-TS-63 | 0.27 | 6.42E-10 | 5.1 |
| hu8E2-TS-57 | 0.25 | 6.58E-10 | 3.9 |
| hu8E2-TS-58 | 0.23 | 9.57E-10 | 6.0 |
| hu8E2-TS-49 | 0.19 | 1.50E-09 | 5.2 |
| hu8E2 WT | | 4.54E-09 | |
| hu8E2 WT 2 | | 5.03E-09 | |
| Mean hu8E2 WT (n = 2) | N/D | 4.78E-09 | |

[1]Sequence of antibody $V_H$ and $V_L$ as set out in Table 1
[2]Potency ((μg/ml) as determined in BaF Human IL-11R cell proliferation assay
[3]Biacore data generated at pH 8.5 and 37° C.
NP means no potency;
N/D means not determined
*some heterogeneity observed, an accurate $K_D$ difficult to determine Ten affinity matured antibodies, (TS-306, TS-2, TS-4, TS-7, TS-14, TS-51, TS-101, TS-108, TS-134 and TS-136,) were selected based on their improved ability to inhibit hIL-11 induced proliferation in BaF3 cells in comparison to 8E2, 8D10 and 8E4, and their improved affinity to human IL-11Rα compared to 8E2. CDR sequence was also considered in selecting these affinity matured antibodies. Some clones which had a CDR sequence close to or the same as the relevant consensus sequence were selected.

These antibodies were tested for inhibition of human, cyno and/or mouse IL-11-induced proliferation of BaF3 cells transfected with human, cyno or mouse IL-11R. Binding to human and cyno IL-11R transfected cells and measurement of mean fluorescence intensity by flow cytometry was also performed. Compared to the parental 8E2 clone, each of the selected clones more potently inhibited hIL-11 and cyno-IL-11-induced proliferation and bound with greater affinity to human and cyno IL-11R.

Example 2

Epitope Mapping

Competition ELISA and Biacore data indicate that 8E2, 8E4 and 8D10 compete with each other for binding to hIL-11Rα and may recognize the same region of hIL-11Rα.

Domain swapping (murine-human) Biacore data showed that at least amino acids 111-215 (Fn type 3 domain 1) of hIL-11Rα (SEQ ID NO: 1) was required for 8E2 and 8D10 binding and substituting mouse for human sequence in this region reduced the affinity of 8E4 binding (Table 4).

TABLE 4

Binding of IL-11 receptors to antibodies.

| Sequence | 8E4 | 8E2 | 8D10 | 4E5 |
|---|---|---|---|---|
| SEQ ID NO: 86 | weak binding | N/B | N/B | strong binding |
| SEQ ID NO: 87 | strong binding | strong binding | strong binding | strong binding |
| SEQ ID NO: 88 | strong binding | strong binding | strong binding | weak binding |
| SEQ ID NO: 89 | weak binding | N/B | N/B | weak binding |
| SEQ ID NO: 3 | N/A | strong binding | strong binding | weak binding |
| SEQ ID NO: 90 | N/A | N/B | N/B | strong binding |

N/A: not assessed
N/B: no or ablated binding
4E5 is a mouse monoclonal antibody with strong binding affinity to mouse IL-11Rα.

In the results presented in Table 4, reference to "strong binding" indicates affinities ($K_D$) of about 10 nM or lower. Reference to "weak binding" indicates affinities ($K_D$) of about 50 nM or higher.

Twenty eight constructs having a single amino acid substitution in the region covering both the Ig-like domain and the Fibronectin type 3 domain 1 of hIL-11Rα were made by replacing the native human amino acid with the corresponding mouse amino acid residue. Five mutants of a truncated hIL-11R (SEQ ID NO:85) (P65S, K66R, L101S, V117E, A178S) were expressed and purified (numbering relative to the amino acid position in SEQ ID NO:1). Corresponding constructs were used to transfect cells, which were subsequently stained with 8E2, 8E4 and 8D10. 8E2 and 8E10 binding was shown to be reduced in V117E transfected cells by flow cytometry.

Flow data were confirmed by Biacore. All Biacore sensorgrams fitted well to a 1:1 binding model and the derived $K_D$ values are given in Table 5.

The V117E mutant did not bind to 8E2 and 8D10 at the concentrations used in this assay, and a $K_D$ for this interaction could not be determined. This residue contributes to the binding interaction of these two antibodies.

The K66R mutation led to a decrease in $K_D$ of just over twofold when compared to WT D½(SEQ ID NO: 85) for antibodies 8E2 and 8D10, indicating some involvement of this residue in antibody binding.

The mutants V117E and K66R also bound to antibody 8E4 with a significantly lower affinity than WT D½(SEQ ID NO: 85). These residues may contribute to the binding interaction of antibody 8E4 with hIL-11Rα.

ANOVA and Tukey's Multiple Comparisons tests indicated that both V95E and K44R affinities were significantly different (p<0.05) to WT D½(SEQ ID NO: 85) for all antibodies tested.

TABLE 5

Affinities of antibodies for point mutants of soluble human IL-11Rα (SEQ ID NO: 85)

| Receptor/Mutant | K$_D$ (nM) | | |
|---|---|---|---|
| | 8E2 | 8E4 | 8D10 |
| K66R (SEQ ID NO: 96) | 2.4 ± 0.13 | 5.6 ± 0.1 | 1.3 ± 0.09 |
| L101S (SEQ ID NO: 98) | 1.17 ± 0.03 | 2.98 ± 0.06 | 0.7 ± 0.03 |
| P65S (SEQ ID NO: 97) | 1.08 ± 0.02 | 2.71 ± 0.1 | 0.67 ± 0.02 |
| A178S (SEQ ID NO: 99) | 1.1 ± 0.05 | 2.63 ± 0.1 | 0.6 ± 0.03 |
| V117E (SEQ ID NO: 95) | * | 5.54 ± 0.1 | * |
| SEQ ID NO: 85 | 1.0, 1.1 | 3.2, 3.7 | 0.57, 0.69 |
| SEQ ID NO: 85 | 1.0 ± 0.04 | 2.78 ± 0.08 | 0.58 ± 0.03 |
| SEQ ID NO: 3 | 1.8 ± 0.06 | 4.0 ± 0.1 | 1.0 ± 0.03 |

Affinities of antibodies for various receptor mutants. N = 2 for WT D1/2 (SEQ ID NO: 85), both values are shown. All other values are mean ± SE. N = 3 for WT F/L (SEQ ID NO: 3), N = 4 for all others. Values highlighted in bold have K$_D$ values significantly different to WT D1/2 (p < 0.05). Positions of mutations are relative to SEQ ID NO: 1.
* indicates undetectable binding.

Example 3

Comparative Data

A non-neutralizing anti-IL-11R antibody (4D12; commercially available antibody from Santa Cruz) was shown to bind to human IL-11Rα by ELISA. 4D12 was shown to bind to BaF3 cells transfected with human IL-11Rα and was shown to bind to 293 cells transfected with human or mouse IL-11Rα.

4D12 did not neutralize human or mouse IL-11 induced cellular proliferation in BaF3 cells incubated with 0.5 ng/mL hIL-11 or 3 ng/mL mIL-11R.

Competition ELISAs were used to show that 4D12 does not compete for binding to IL-11Rα with either 8D10 or 8E2.

The invention claimed is:

1. An isolated or recombinant IL-11Rα-binding protein comprising an antigen binding domain of an antibody, wherein the antigen binding domain specifically binds to IL-11Rα and neutralizes IL-11 signaling, and the antigen binding domain binds to an epitope comprising residues within the first fibronectin III domain of IL-11Rα, wherein the first fibronectin III domain comprises amino acids 111-215 of SEQ ID NO: 1, and wherein the antigen binding domain comprises a heavy chain variable region ($V_H$) and a light chain variable region ($V_L$), the $V_H$ comprising:
   (i) a complementarity determining region (CDR) 1 comprising a sequence set forth between amino acids 31-35 of SEQ ID NO: 37 optionally comprising three or fewer amino acid substitutions, a CDR2 comprising a sequence set forth between amino acids 50-66 of SEQ ID NO: 37 optionally comprising four or fewer amino acid substitutions and a CDR3 comprising a sequence set forth between amino acids 99-107 of SEQ ID NO: 37 optionally comprising four or fewer amino acid substitutions; or
   (ii) a sequence at least about 95% identical to the sequence set forth in SEQ ID NO: 37.

2. The IL-11Rα-binding protein of claim 1, wherein the amino acid substitution(s) in CDR2 of the $V_H$ are between amino acids 54 and 57 of SEQ ID NO: 37 and/or the amino acid substitution(s) of the $V_H$ are within the six N-terminal or the six C-terminal residues of the CDR3.

3. The IL-11Rα-binding protein of claim 1, wherein the antigen binding domain comprises a $V_H$ comprising the sequence set forth in SEQ ID NO: 71.

4. The IL-11Rα-binding protein of claim 1, wherein the antigen binding domain comprises a $V_H$ comprising the sequence set forth in SEQ ID NO: 72.

5. The IL-11Rα-binding protein of claim 1, wherein the antigen binding domain comprises:
   (i) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 5;
   (ii) a $V_H$ comprising the sequence set forth in SEQ ID NO: 37 and a $V_L$ comprising the sequence set forth in SEQ ID NO: 5;
   (iii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 6;
   (iv) a $V_H$ comprising the sequence set forth in SEQ ID NO: 37 and a $V_L$ comprising the sequence set forth in SEQ ID NO: 6;
   (v) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 7;
   (vi) a $V_H$ comprising the sequence set forth in SEQ ID NO: 37 and a $V_L$ comprising the sequence set forth in SEQ ID NO: 7;
   (vii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 8;
   (viii) a $V_H$ comprising the sequence set forth in SEQ ID NO: 37 and a $V_L$ comprising the sequence set forth in SEQ ID NO: 8;
   (ix) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 9;
   (x) a $V_H$ comprising the sequence set forth in SEQ ID NO: 37 and a $V_L$ comprising the sequence set forth in SEQ ID NO: 9;
   (xi) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 10;
   (xii) a $V_H$ comprising the sequence set forth in SEQ ID NO: 37 and a $V_L$ comprising the sequence set forth in SEQ ID NO: 10;
   (xiii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 11;
   (xiv) a $V_H$ comprising the sequence set forth in SEQ ID NO: 37 and a $V_L$ comprising the sequence set forth in SEQ ID NO: 11;

(xv) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 12;
(xvi) a $V_H$ comprising the sequence set forth in SEQ ID NO: 37 and a $V_L$ comprising the sequence set forth in SEQ ID NO: 12;
(xvii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 13;
(xviii) a $V_H$ comprising the sequence set forth in SEQ ID NO: 37 and a $V_L$ comprising the sequence set forth in SEQ ID NO: 13;
(xix) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 14;
(xx) a $V_H$ comprising the sequence set forth in SEQ ID NO: 37 and a $V_L$ comprising the sequence set forth in SEQ ID NO: 14;
(xxi) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 15;
(xxii) a $V_H$ comprising the sequence set forth in SEQ ID NO: 37 and a $V_L$ comprising the sequence set forth in SEQ ID NO: 15;
(xxiii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 16;
(xxiv) a $V_H$ comprising the sequence set forth in SEQ ID NO: 37 and a $V_L$ comprising the sequence set forth in SEQ ID NO: 16;
(xxv) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 17;
(xxvi) a $V_H$ comprising the sequence set forth in SEQ ID NO: 37 and a $V_L$ comprising the sequence set forth in SEQ ID NO: 17;
(xxvii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 18;
(xxviii) a $V_H$ comprising the sequence set forth in SEQ ID NO: 37 and a $V_L$ comprising the sequence set forth in SEQ ID NO: 18;
(xxix) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 19;
(xxx) a $V_H$ comprising the sequence set forth in SEQ ID NO: 37 and a $V_L$ comprising the sequence set forth in SEQ ID NO: 19;
(xxxi) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 20;
(xxxii) a $V_H$ comprising the sequence set forth in SEQ ID NO: 37 and a $V_L$ comprising the sequence set forth in SEQ ID NO: 20;
(xxxiii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 21;
(xxxiv) a $V_H$ comprising the sequence set forth in SEQ ID NO: 37 and a $V_L$ comprising the sequence set forth in SEQ ID NO: 21;
(xxxv) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 22;
(xxxvi) a $V_H$ comprising the sequence set forth in SEQ ID NO: 37 and a $V_L$ comprising the sequence set forth in SEQ ID NO: 22;
(xxxvii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 23;
(xxxviii) a $V_H$ comprising the sequence set forth in SEQ ID NO: 37 and a $V_L$ comprising the sequence set forth in SEQ ID NO: 23;
(xxxix) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 24;
(xl) a $V_H$ comprising the sequence set forth in SEQ ID NO: 37 and a $V_L$ comprising the sequence set forth in SEQ ID NO: 24;
(xli) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 25;
(xlii) a $V_H$ comprising the sequence set forth in SEQ ID NO: 37 and a $V_L$ comprising the sequence set forth in SEQ ID NO: 25;
(xliii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 26;
(xliv) a $V_H$ comprising the sequence set forth in SEQ ID NO: 37 and a $V_L$ comprising the sequence set forth in SEQ ID NO: 26;
(xlv) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 27;
(xlvi) a $V_H$ comprising the sequence set forth in SEQ ID NO: 37 and a $V_L$ comprising the sequence set forth in SEQ ID NO: 27;
(xlvii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 28;
(xlviii) a $V_H$ comprising the sequence set forth in SEQ ID NO: 37 and a $V_L$ comprising the sequence set forth in SEQ ID NO: 28;
(xlix) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 29;
(l) a $V_H$ comprising the sequence set forth in SEQ ID NO: 37 and a $V_L$ comprising the sequence set forth in SEQ ID NO: 29;
(li) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 30;
(lii) a $V_H$ comprising the sequence set forth in SEQ ID NO: 37 and a $V_L$ comprising the sequence set forth in SEQ ID NO: 30;
(liii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 31;
(liv) a $V_H$ comprising the sequence set forth in SEQ ID NO: 37 and a $V_L$ comprising the sequence set forth in SEQ ID NO: 31;
(lv) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 32;
(lvi) a $V_H$ comprising the sequence set forth in SEQ ID NO: 37 and a $V_L$ comprising the sequence set forth in SEQ ID NO: 32;
(lvii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 33;
(lviii) a $V_H$ comprising the sequence set forth in SEQ ID NO: 37 and a $V_L$ comprising the sequence set forth in SEQ ID NO: 33;

(lix) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 34; or (lx) a $V_H$ comprising the sequence set forth in SEQ ID NO: 37 and a $V_L$ comprising the sequence set forth in SEQ ID NO: 34.

6. The IL-11Rα-binding protein of claim 1, wherein the antigen binding domain comprises:

(i) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 8;

(ii) a $V_H$ comprising the sequence set forth in SEQ ID NO: 37 and a $V_L$ comprising the sequence set forth in SEQ ID NO: 8;

(iii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 15;

(iv) a $V_H$ comprising the sequence set forth in SEQ ID NO: 37 and a $V_L$ comprising the sequence set forth in SEQ ID NO: 15;

(v) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 16;

(vi) a $V_H$ comprising the sequence set forth in SEQ ID NO: 37 and a $V_L$ comprising the sequence set forth in SEQ ID NO: 16;

(vii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 18;

(viii) a $V_H$ comprising the sequence set forth in SEQ ID NO: 37 and a $V_L$ comprising the sequence set forth in SEQ ID NO: 18;

(ix) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 29; or (x) a $V_H$ comprising the sequence set forth in SEQ ID NO: 37 and a $V_L$ comprising the sequence set forth in SEQ ID NO: 29.

7. The IL-11Rα-binding protein of claim 1, wherein the $V_H$ and $V_L$ bind to form a Fv comprising an antigen binding domain, and wherein the $V_H$ and $V_L$ are in a single polypeptide chain or the $V_H$ and $V_L$ are in separate polypeptide chains.

8. The IL-11Rα-binding protein of claim 7, wherein if the $V_H$ and $V_L$ are in a single polypeptide chain, the protein is:
(i) a single chain Fv fragment (scFv);
(ii) a dimeric scFv (di-scFv);
(iii) one of (i) or (ii) linked to a constant region of an antibody, Fc or a heavy chain constant domain ($C_H$)2 and/or $C_H$3; or
(iv) one of (i) or (ii) linked to a protein that binds to an immune effector cell, or if the $V_H$ and $V_L$ are in separate polypeptide chains the protein is:
(a) a diabody;
(b) a triabody;
(c) a tetrabody;
(d) a Fab;
(e) a F(ab')2;
(f) a Fv;
(g) one of (a) to (f) linked to a constant region of an antibody, Fc or a heavy chain constant domain ($C_H$)2 and/or $C_H$3;
(h) one of (a) to (f) linked to a protein that binds to an immune effector cell; or
(i) an antibody.

9. The IL-11Rα-binding protein of claim 8, wherein the antigen binding domain comprises:

(i) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 8;

(ii) a $V_H$ comprising the sequence set forth in SEQ ID NO: 37 and a $V_L$ comprising the sequence set forth in SEQ ID NO: 8;

(iii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 15;

(iv) a $V_H$ comprising the sequence set forth in SEQ ID NO: 37 and a $V_L$ comprising the sequence set forth in SEQ ID NO: 15;

(v) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 16;

(vi) a $V_H$ comprising the sequence set forth in SEQ ID NO: 37 and a $V_L$ comprising the sequence set forth in SEQ ID NO: 16;

(vii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 18;

(viii) a $V_H$ comprising the sequence set forth in SEQ ID NO: 37 and a $V_L$ comprising the sequence set forth in SEQ ID NO: 18;

(ix) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 29; or (x) a $V_H$ comprising the sequence set forth in SEQ ID NO: 37 and a $V_L$ comprising the sequence set forth in SEQ ID NO: 29.

10. The IL-11Rα-binding protein of claim 1, which is conjugated to another compound.

11. A composition comprising the IL-11Rα-binding protein of claim 1 and a pharmaceutically acceptable carrier.

12. The IL-11Rα-binding protein of claim 1, further comprising a constant region of an IgG4 antibody or a stabilized constant region of an IgG4 antibody comprising a proline at position 241 according to the numbering system of Kabat, wherein the constant region optionally lacks a C-terminal lysine residue.

13. The IL-11Rα-binding protein of claim 9, further comprising a constant region of an IgG4 antibody or a stabilized constant region of an IgG4 antibody comprising a proline at position 241 according to the numbering system of Kabat, wherein the constant region optionally lacks a C-terminal lysine residue.

14. The IL-11Rα-binding protein of claim 1, comprising:
(i) a heavy chain which comprises a $V_H$ comprising the sequence set forth in SEQ ID NO: 37 and a stabilized constant region of an IgG4 antibody comprising a proline at position 241 according to the numbering system of Kabat, wherein the constant region optionally lacks a C terminal lysine residue and a light chain which comprises a $V_L$ comprising the sequence set forth in SEQ ID NO: 18 and a human light chain constant region; or
(ii) a heavy chain which comprises the sequence set forth in SEQ ID NO: 37 and a stabilized constant region of an IgG4 antibody comprising a proline at position 241 according to the numbering system of Kabat, wherein the constant region optionally lacks a C-terminal lysine residue and a light chain which comprises a $V_L$ comprising the sequence set forth in SEQ ID NO: 18 and a human light chain constant region.

15. An isolated or recombinant IL-11Rα binding protein comprising an antigen binding domain of an antibody, wherein the antigen binding domain specifically binds to IL-11Rα and neutralizes IL-11 signaling, and the antigen binding domain binds to an epitope comprising residues within the first fibronectin III domain of IL-11Rα, wherein the first fibronectin III domain comprises amino acids 111-215 of SEQ ID NO: 1, and wherein the antigen binding domain comprises a heavy chain variable region ($V_H$) comprising the sequence set forth in SEQ ID NO: 37 and a light chain variable region ($V_L$).

* * * * *